US012370248B2

(12) United States Patent
Curtiss et al.

(10) Patent No.: US 12,370,248 B2
(45) Date of Patent: Jul. 29, 2025

(54) ATTENUATED SALMONELLA SYNTHESIZING ANTIGENS FOR VACCINATING AGAINST HELICOBACTER PYLORI

(71) Applicant: UNIVERSITY OF FLORIDA RESEARCH FOUNDATION, INCORPORATED, Gainesville, FL (US)

(72) Inventors: Roy Curtiss, Gainesville, FL (US); Amir Ghasemi, Boca Raton, FL (US)

(73) Assignee: UNIVERSITY OF FLORIDA RESEARCH FOUNDATION, INCORPORATED, Gainesville, FL (US)

( * ) Notice: Subject to any disclaimer, the term of this patent is extended or adjusted under 35 U.S.C. 154(b) by 412 days.

(21) Appl. No.: 17/798,181

(22) PCT Filed: Feb. 8, 2021

(86) PCT No.: PCT/US2021/017083
§ 371 (c)(1),
(2) Date: Aug. 8, 2022

(87) PCT Pub. No.: WO2021/159075
PCT Pub. Date: Aug. 12, 2021

(65) Prior Publication Data
US 2023/0090746 A1    Mar. 23, 2023

Related U.S. Application Data

(60) Provisional application No. 62/971,365, filed on Feb. 7, 2020.

(51) Int. Cl.
| | |
|---|---|
| *A61K 39/38* | (2006.01) |
| *A61K 39/02* | (2006.01) |
| *A61P 31/04* | (2006.01) |
| *C12N 1/20* | (2006.01) |
| *C12N 1/36* | (2006.01) |
| *C12N 15/85* | (2006.01) |
| *A61K 39/00* | (2006.01) |

(52) U.S. Cl.
CPC ............ *A61K 39/105* (2013.01); *A61P 31/04* (2018.01); *C12N 1/20* (2013.01); *C12N 1/36* (2013.01); *C12N 15/85* (2013.01); *A61K 2039/522* (2013.01); *A61K 2039/523* (2013.01); *A61K 2039/55594* (2013.01); *C12N 2800/107* (2013.01)

(58) Field of Classification Search
CPC .................................................. A61K 39/105
See application file for complete search history.

(56) References Cited

U.S. PATENT DOCUMENTS

| | | |
|---|---|---|
| 6,585,975 B1 | 7/2003 | Kleanthous et al. |
| 2017/0224806 A1 | 8/2017 | Curtiss, III et al. |

OTHER PUBLICATIONS

Abadi, Amin Talebi Bezmin, "Vaccine against Helicobacter pylori: Inevitable approach", World J. Gastroenterology, 2016, Mar. 21, vol. 22, No. 11, pp. 3150-3157.
Adcox, Haley E. et al., "*Salmonella* Extracellular Matrix Components Influence Biofilm Formation and Gallbladder Colonization", Infection and Immunity, Nov. 2016, vol. 84, No. 11, pp. 3243-3251.
Ahman, Heidi et al., "Dose dependency of antibody response in infants and children to pneumoccal polysaccharides conjugated to tetanus toxoid", Vaccine, 1999, vol. 17, pp. 2726-2732.
Ameiss, Keith et al., "Delivery of Woodchuck Hepatitis Virus-like Particle Presented Influenza M2e by Recombinant Attenuated *Salmonella* Displaying a Delayed Lysis Phenotype", Vaccine, 2010, Sep. 24, vol. 28, No. 41, pp. 6704-6713.
Ashraf, Shamaila et al., "Protective cellular responses elicited by vaccination with influenza nucleoprotein delivered by a live recombinant attenuated *Salmonella* vaccine", Vaccine, May 2, 20113, vol. 29, No. 23, pp. 3990-4002.
Atkins, Helen S. et al., "Recombinant *Salmonella* vaccines for biodefence", Vaccine, 2006, vol. 24, pp. 2710-2717.

(Continued)

*Primary Examiner* — Albert M Navarro
(74) *Attorney, Agent, or Firm* — Timothy H. Van Dyke; Wolter Van Dyke Davis, PLLC

(57) ABSTRACT

*Helicobacter pylori* is a leading cause of gastric mucosal inflammation, peptic ulcers, and gastric adenocarcinoma. Emerging antimicrobial-resistant *H. pylori* has hampered the successful eradication of frequent chronic infections. Additionally, due to the absence of effective vaccines against *H. pylori*, a safe vaccine is highly demanded. Disclosed herein are innovative Protective Immunity Enhanced *Salmonella* Vaccine (PIESV) vector strains to deliver and express multiple *H. pylori* antigen genes. Immunization of mice with a vaccine delivering the HpaA, NapA (also termed Hp-NAP), UreA and UreB antigens, provided sterile protection against *H. pylori* SS1 infection in 7 out of 10 tested mice. Compared to the control groups that had received PBS or a PIESV with an empty vector, immunized mice exhibited specific and significant cellular recall responses and antigen-specific IgG2c, IgG1, total IgG and gastric IgA antibody titers. Importantly, the mice immunized with the vaccine candidate showed a significant reduction in a load of an unidentified Gram-positive rod-shaped bacteria in their stomach compared to the control groups. In conclusion, a *Salmonella* Typhimurium-based live vaccine delivering four antigens shows promise as a safe and effective vaccine against *H. pylori* infection.

18 Claims, 12 Drawing Sheets

Specification includes a Sequence Listing.

(56) References Cited

OTHER PUBLICATIONS

Beccerra-Artiles, Aniuska et al., "A simple proteomics-based approach to identification of immunodominant antigens from a complex pathogen: application to the CD4 T cell response against human Herpesvirus 6B", Plos One, Nov. 23, 2015, vol. 10, No. 1, 24 pages.

Benoun, Joseph M. et al., "Optimal protection against *Salmonella* infection requires noncirculating memory", PNAS, Oct. 9, 2018, vol. 115, No. 41, pp. 10416-10421.

Blanchard, Thomas et al., "Identification of Helicobacter pylori and the evolution of an efficacious childhood vaccine to protect against gastritis and peptic ulcer disease", Pediatric Research, Jan. 2017, vol. 81, No. 1, pp. 170-176.

Brandtzaeg, Per, "Role of secretory antibodies in the defence against infections", Int. J. Med Microbiol, 2003, vol. 293, pp. 3-15.

Brandtzaeg, Per et al., "Regional specialization in the mucosal immune system: primed cells do not always home along the same track", Front. Matter, 1999, vol. 20, No. 6, pp. 267-277.

Brandtzaeg, Per et al., "The B-cell of human mucosae and exocrine glands", Immunological Reviews, 1999, vol. 171, pp. 45-87.

Broz, Petr et al., "Innate immune response to *Salmonella typhimurium*, a model enteric pathogen", Gut Microbes, 2012, Mar./Apr. 2012, vol. 3, No. 2, pp. 62-70.

Cardenas, Lucia et al., "Oral immunization using live attenuated *Salmonella* spp. as carries of foreign antigens", Clinical Microbiology Reviews, Jul. 1992, vol. 5, No. 3, pp. 328-342.

Carlsohn, Elisabet et al., "HpaA is essential for Helicobacter pylori colonization in mice", Infection and Immunity, Feb. 2006, vol. 74, No. 2, pp. 920-926.

Chatfield, Steven N. et al., "Live *Salmonella* as vaccines and carriers of foreign antigenic derterminants", Vaccine, Dec. 1989, vol. 7, pp. 495-498.

Cheminay, Cedric et al., "Rational design of *Salmonella* recombinant vaccines", International Journal of Medical Microbiology, 2008, vol. 298, pp. 87-98.

Chen, Jinru et al., "Protective effect of exopolysaccharide colanic acid of *Escherichia coli* O157:H7 to osmotic and oxidative stress", International Journal of Food Microbiology, 2004, vol. 93, pp. 281-286.

Collins, L. Vincent et al., "Mutations at rfc or pmi Attenuate *Salmonella typhimurium* Virulence for Mice", Infection and Immunity, Mar. 1991, vol. 59, No. 3, pp. 1079-1085.

Correa, Pelayo et al., "Helicobacter pylori Infection and Gastric Adenocarcinoma", US Gastroenterol Hepatol Rev. Jun. 2011, vol. 7, No. 1, pp. 59-64.

Crawford, Robert W. et al., "Identification of a Bile-Induced Exopolysaccharide Required for *Salmonella* Biofilm Formation on Gallstone Surfaces", Infection and Immunity, Nov. 2008, p. 5341-5349 Vol. 76, No. 11.

Curtiss, Roy III, "Bacterial infectious disease control by vaccine development", J. Clin. Invest., 2002, vol. 110, pp. 1061-1066.

Curtiss, Roy III et al., "*Salmonella enterica* Serovar Typhimurium Strains with Regulated Delayed Attenuation In Vivo", Infection and Immunity, Mar. 2009, p. 1071-1082 vol. 77, No. 3.

Curtiss, Roy III et al., "New technologies in using recombinant Salmonella vaccine vectors", Crit Rev Immunol. 2010, vol. 30, No. 3, pp. 255-270.

De Boever, S. et al., "The influence of age and repeated lipopolysaccharide administration on body temperature and concentration of interleukin-6 and IgM antibodies against lipopolysaccharide in broiler chickens", Avian Pathology, Feb. 2008, vol. 37, No. 1, pp. 39-44.

Eaton, K.A. et al., "Vaccination of Gnotobiotic piglets against Helicobacter pylori", The Journal of Infectious Diseases 1998, vol. 178, pp. 1399-1405.

Ermak, Thomas H. et al., "Immunization of Mice with Urease Vaccine Affords Protection against Helicobacter pylori Infection in the Absence of Antibodies and Is Mediated by MHC Class II-restricted Responses", J. Exp. Med, Dec. 21, 1998, vol. 188, No. 12, pp. 2277-2287.

Everhart, James E. et al., "Burden of Digestive Diseases in the United States Part I: Overall and Upper Gastrointestinal Diseases", Gastroenterology, 2009, vol. 136, pp. 376-386.

Flahou, Bram et al., "The local immune response of mice after Helicobacter suis infection: strain differences and distinction with Helicobacter pylori", Veterinary Research, 2012, vol. 43, No. 75, 10 pages.

Gagnaire, Aurélie et al., "Collateral damage: insights into bacterial mechanisms that predispose host cells to cancer", Microbiology, 2017, 20 pages.

Galen, James E. et al., "The delicate balance in genetically engineering live vaccines", Vaccine, Jul. 31, 2014, vol. No. 35, pp. 4376-4385.

Germanier, R. et al., "Immunity in Experimental Salmonellosis", Infection and Immunity, Dec. 1971, p. 663-673, vol. 4, No. 6.

Ghasemia, Amir et al., "Identification of a new immunogenic candidate conferring protectionagainst Brucella melitensis Infection in Mice", Molecular Immunology, 2014, vol. 62, pp. 142-149.

Gibson, D. L. et al., "*Salmonella* Produces an O-Antigen Capsule Regulated by AgfD and Important for Environmental Persistence", Journal of Bacteriology, Nov. 2006, p. 7722-7730 Vol. 188, No. 22.

Graham, David Y. et al., "Newer concepts regarding resistance in the treatment Helicobacter pylori infections", Nat Clin Pract Gastroenterol Hepatol. Jun. 2008, vol. 5, No. 6, pp. 321-331.

Graham, David Y. et al., "Epidemiology of Helicobacter Pylori in an Asymptomatic Population in the United States", Gastroenterology 1991, vol. 100, pp. 1495-1501.

Griffin, Amanda J. et al., "Development of protective immunity to *Salmonella*, a mucosal pathogen with a systemic agenda", Mucosal Immunol. Jul. 2011, vol. 4, No. 4, pp. 371-382.

Griffin, Amanda J. et al., "Generation of *Salmonella*-specific Th1 cells requires sustained antigen stimulation", Vaccine. Mar. 24, 2011, vol. 29, No. 15, pp. 2697-2704.

Gunn, Bronwyn M. et al., "Construction of Recombinant Attenuated *Salmonella enterica* Serovar Typhimurium Vaccine Vector Strains for Safety in Newborn and Infant Mice", Clinical and Vaccine Immunology, Mar. 2010, p. 354-362 vol. 17, No. 3.

Hase, Koji et al., "Uptake through glycoprotein 2 of FimH bacteria by M cells initiates mucosal immune response", Nature, Nov. 12, 2009, vol. 462, pp. 226-230.

Hatakeyama, Masanori, "Helicobacter pylori CagA and Gastric Cancer: A Paradigm for Hit-and-Run Carcinogenesis", Cell Host & Microbe, vol. 15, Mar. 12, 2014, pp. 306-316.

Hopkins, Sally et al., "A recombinant *Salmonella typhimurium* Vaccine Induces Local Immunity by Four Different Routes of Immunization", Infection and Immunity, Sep. 1995, p. 3279-3286 vol. 63, No. 9.

Irvine, Katherine L. et al., "Identification of Key residues that confer Rhodobacter sphaeroides LPS Activity at Horse TLR4/MD-2", Plos One, 2014, vol. 9, No. 5, 9 pages.

Jiang, Yanlong et al., "Protection Against Necrotic Enteritis in Broiler Chickens to Regulated Delayed Lysis *Salmonella* Vaccines", Avian Diseases, 2015, vol. 59, pp. 475-485.

Juárez-Rodríguez, Maria et al., "Live Attenuated *Salmonella* Vaccines Displaying Regulated Delayed Lysis and Delayed Antigen Synthesis to Confer Protection against *Mycobacterium tuberculosis*", Infection and Immunity, 2011, pp. 815-831.

Kang, Ho Young et al., "Immune responses to recombinant Pneumococcal PspA Antigen Delivered by Live Attenuated *Salmonella enterica* Serovar Typhimurium Vaccine", Infection and Immunity, Apr. 2002, p. 1739-1749 vol. 70, No. 4.

Kong, Wei et al., "Turning self-destructing *Salmonella* into a universal DNA vaccine delivery platform", PNAS, Nov. 20, 2012, vol. 109, No. 47, pp. 19414-19419.

Kong, Qingke et al., "*Salmonella* synthesizing 1-monophosphorylated LPS exhibits low endotoxic activity while retaining its immunogenicity", J Immunol, Jul. 1, 2011, vol. 187, No. 1, pp. 412-423.

(56) References Cited

OTHER PUBLICATIONS

Kong, Wei et al., "Regulated programmed lysis of recombinant *Salmonella* in host tissues to release protective antigens and confer biological containment", PNAS, Jul. 8, 2008, vol. 105, No. 27, pp. 9361-9366.

Kronsteiner, Barbara et al., "Helicobacter pylori Infection in a Pig Model Is Dominated by Th1 and Cytotoxic CD8 T Cell Responses", Infection and Immunity, Oct. 2013, vol. 81, No. 10, pp. 3803-3813.

Lambert, Paul-Henri et al., "Can successful vaccines teach US how to induce efficient protective immune responses?", Nature Medicine Supplement, Apr. 2005, vol. 11, No. 4, pp. S54-S62.

Aniewski, Pawel et al., "Analysis of Spleen-Induced Fimbria Production in Recombinant Attenuated *Salmonella enterica* Serovar Typhimurium Vaccin Strains", American Society for Microbiology, Jul./Aug. 2017, vol. 3, Issue 4.

Lee, Jun Sik et al., "Outer membrane protein a of *Salmonella enterica* serovar Typhimurium activates dendritic cells and enhances Th1 polarization", BMC Microbiology, 2010, vol. 10, No. 263, 8 pages.

Li, Yuhua et al., A sopB Deletion Mutation Enhances the Immunogenicity and Protective Efficacy of a Heterologous Antigen Delivered by Live Attenuated *Salmonella enterica* Vaccines, Infection and Immunity, Nov. 2008, p. 5238-5246 vol. 76, No. 11.

Li, Yuhua et al., "Evaluation of new generation *Salmonella enterica* serovar Typhimurium vaccines with regulated delayed attenuation to induce immune responses against PspA", PNAS, Jan. 13, 2009, vol. 106, No. 2, pp. 593-598.

Lohmann, Katharina L. et al., "The equine TLR4/MD-2 complex mediates recognition of lipopolysaccharide from Rhodobacter sphaeroides as an agonist", Journal of Endotoxin Research, 2007, vol. 13, No. 4, pp. 235-242.

Lohmann, Katharina L. et al., "Lipopolysaccharide from Rhodobacter sphaeroides is an agonist in equine cells", Journal of Endotoxin Research, 2003, vol. 9, No. 1, pp. 33-37.

Mantis, Nicholas J. et al., "Secretory IgA: Arresting Microbial Pathogens at Epithelial Borders", Immunol Invest, 2010, vol. 39, pp. 383-406.

Megraud, F. "H Pylori antibiotic resistance: prevalence, importance, and advances in testing", Gut, 2004, vol. 53, pp. 1374-1384.

Michalkiewicz, Jacek et al., "Innate Immunity Components and Cytokines in Gastric Mucosa in Children with Helicobacter pylori Infection", Mediators of Inflammation, 2015, vol. 2015, Article ID 176726, 7 pages.

Mini, Roberta et al., "Western Blotting of Total Lysate of Helicobacter pylori in Cases of Atrophic Body Gastritis", Clinical Chemistry, 2006, vol. 52, No. 2, pp. 220-226.

Mao, Ying et al., "Insertion Mutagenesis of wca Reduces Acid and Heat Tolerance of Enterohemorrhagic *Escherichia coli* O157:H7", Journal of Bacteriology, Jun. 2001, p. 3811-3815, vol. 183, No. 12.

Mohammad, Nazanin et al., "In Silico Design of a Chimeric Protein Containing Antigenic Fragments of Helicobacter pylori; A Bioinformatic Approach", The Open Microbiology Journal, 2016, vol. 10, pp. 97-112.

Moon, James J. et al., "Tracking the Dynamics of *Salmonella* specific T cell responses", Curr Top Microbiol Immunol. 2009, vol. 334, pp. 179-198.

Moyat, Mati et al., "Use of VacA as a Vaccine Antigen", Toxins 2016, vol. 8, No. 181, 7 pages.

Muralinath, Maneesha et al., "Immunization with *Salmonella enterica* Serovar Typhimurium-Derived Outer Membrane Vesicles Delivering the Pneumococcal Protein PspA Confers Protection against Challenge with *Streptococcus pneumoniae*", Infection and Immunity, Feb. 2011, p. 887-894 vol. 79, No. 2.

Nakayama, Koji et al., "Construction of an ASD Expression-Cloning Vector: Stable Maintenance and High Level Expression of Cloned Genes in a *Salmonella* Vaccine Strain", Bio/Technology, 1988, vol. 6, pp. 693-697.

Nell, Sandra et al., "Dynamics of Lewis b Binding and Sequence Variation of the babA Adhesin Gene during Chronic Helicobacter pylori Infection in Humans", mBio, Nov./Dec. 2014, vol. 5, Issue 6, 10 pages.

Oleastro, Mónica et al., "The Role of Helicobacter pylori Outer Membrane Proteins in Adherence and Pathogenesis", Biology, 2013, vol. 2, pp. 1110-1134.

Ophir, Tslil et al., "A role for Exopolysaccharides in the protection of Microorganism from Desiccation", Applied and Environmental Microbiology, Feb. 1994, vol. 60, No. 2, pp. 740-745.

Pando, Jesmine M. et al., "The Rcs-Regulated Colanic Acid Capsule Maintains Membrane Potential in *Salmonella enterica* serovar Typhimurium", MBio, May/Jun. 2017, vol. 8, issue 3, 15 pages.

Ranjit, Dev K. et al., "Colanic Acid Intermediates Prevent De Novo Shape Recovery of *Escherichia coli* Spheroplasts, Calling into Question Biological Roles Previously Attributed to Colanic Acid", Journal of Bacteriology, Apr. 2016, vol. 198, No. 8, pp. 1230-1240.

Satin, Barbara et al., "The Neutrophil-activating Protein (HP-NAP) of Helicobacter pylori Is a Protective Antigen and a Major Virulence Factor", J. Exp. Med, May 1, 2022, vol. 191, No. 9, pp. 1467-1476.

Sawai, Naoki et al., "Role of Gamma Interferon in Helicobacter pylori-Induced Gastric Inflammatory Responses in a Mouse Model", Infection and Immunity, Jan. 1999, vol. 67, No. 1, pp. 279-285.

Sebbane, Florent et al., "Kinetics of Disease Progression and Host Response in a Rat Model of Bubonic Plague", American Journal of Pathology, May 2005, vol. 166, No. 5, pp. 1427-1439.

Sepulveda, Antonia R., "Helicobacter, Inflammation, and Gastric Cancer", Curr Pathobiol Rep. Mar. 2013, vol. 1, No. 1, pp. 9-18.

Sha, Jian et al., "Braun Lipoprotein (Lpp) Contributes to Virulence of Yersiniae: Potential Role of Lpp in Inducing Bubonic and Pneumonic Plague", Infection and Immunity, Apr. 2008, p. 1390-1409, vol. 76, No. 4.

Shi, Huoying et al., "Live Recombinant *Salmonella* Typhi Vaccines Constructed to Investigate the Role of rpoS in Eliciting Immunity to a Heterologous Antigen", Plos One, 2010, vol. 5, No. 6, 19 pages.

Shi, Huoying et al., "Immunogenicity of a Live Recombinant *Salmonella enterica* Serovar Typhimurium Vaccine Expressing pspA in Neonates and Infant Mice Born from Naïve and Immunized Mothers", Clinical and Vaccine Immunology, Mar. 2010, p. 363-371, vol. 17, No. 3.

Shi, Huoying et al., "Evaluation of Regulated Delayed Attenuation Strategies for *Salmonella enterica* Serovar Typhi Vaccine Vectors in Neonatal and Infant Mice", Clinical and Vaccine Immunology, Jun. 2013, vol. 20, No. 6,p. 931-944.

Siegrist, Claire-Anne, Vaccine immunology, Section One: General aspects of vaccination, 2013, 19 pages.

Sirard, Jean-Claude, "Live attenuated *Salmonella*: a paradigm of mucosal vaccines", Immunological Reviews, 1999, vol. 171, pp. 5-26.

Srinivasan, Aparna et al., "Activation of *Salmonella*-specific immune responses in the intestinal mucosa", Arch. Immunol. Ther. Exp., 2006, vol. 54, pp. 25-31.

Tam, Miguel A. et al., "Early cellular responses to *Salmonella* infection: dendritic cells, monocytes, and more", Immunological Reviews, 2008, vol. 225, pp. 140-162.

Van Miert, A.S.J.P.A.M et al., "The reaction of different animal species to Bacterial Pyrogens", The Institute of Veterinary Pharmacology and Toxicology, University of Utrecht, Netherlands, Sep. 4, 1967, pp. 532-543.

Walsh, Catherine et al., "Elucidation of the MD-2/TLR4 Interface Required for Signaling by Lipid IVa1" The Journal of Immunology, 2008, vol. 181, pp. 1245-1254.

Wang, Shifeng et al., "A Colanic acid operon deletion mutation enhances induction of early antibody responses by live attenuated *Salmonella* vaccine strains", 2013, Infection and Immunity, Sep. 2013, vol. 81, No. 9, pp. 3148-3162.

Wang, Shifeng et al., "Salmonella vaccine vectors displaying delayed antigen synthesis in Vivo to enhanced Immunogenicity", Infection and Immunity, Sep. 2010, vol. 78, No. 9, pp. 3969-3980.

Wang, Shifeng et al., "Comparison of a regulated delayed Antigen synthesis system with in Vivo-inducible promoters for Antigen delivery by live attenuated *Salmonella* vaccines", Infection and Immunity, Feb. 2011, vol. 79, No. 2, pp. 937-949.

(56) References Cited

OTHER PUBLICATIONS

Wang, Shifeng et al., "New technologies in developing recombinant attenuated *Salmonella* vaccine vectors", Microb. Pathog, May 2013, vol. 58, pp. 17-28.

Woof, Jenny M. et al., "Mucosal immunoglobulins", Immunological Reviews, 2005, vol. 206, pp. 64-82.

Xin, Wei et al., "Analysis of type II secretion of recombinant pheumococcal PspA and PspC in a *Salmonella enterica* Serovar Typhinurium vaccine with regulated delayed antigen synthesis", Infection and Immunity, Jul. 2008, vol. 76, No. 7, pp. 3241-3254.

Xin, Wei et al., "The Asd+-DadB+ dual-plasmid system offers novel means to deliver multiple protective antigens by a recombinant attenuated *Salmonella* Vaccine", Infection and Immunity, Oct. 2012, vol. 80, No. 10, pp. 3621-3633.

Yamaoka, Yoshio et al., "Geographic differences in Gastric Cancer Incidence can be explained by differences between Helicobacter pylori strains", Intern Med, 2008, vol. 47, No. 12, pp. 1077-1083.

Xhang, Xiangmin et al., " Inproving *Salmonella* vector with rec mutation to stabilize the DNA cargoes", BMC Microbiology, 2011, vol. 11, No. 31, 15 pages.

FIG. 1. Regulated delayed lysis plasmid vectors pG8R111 and pG8R114
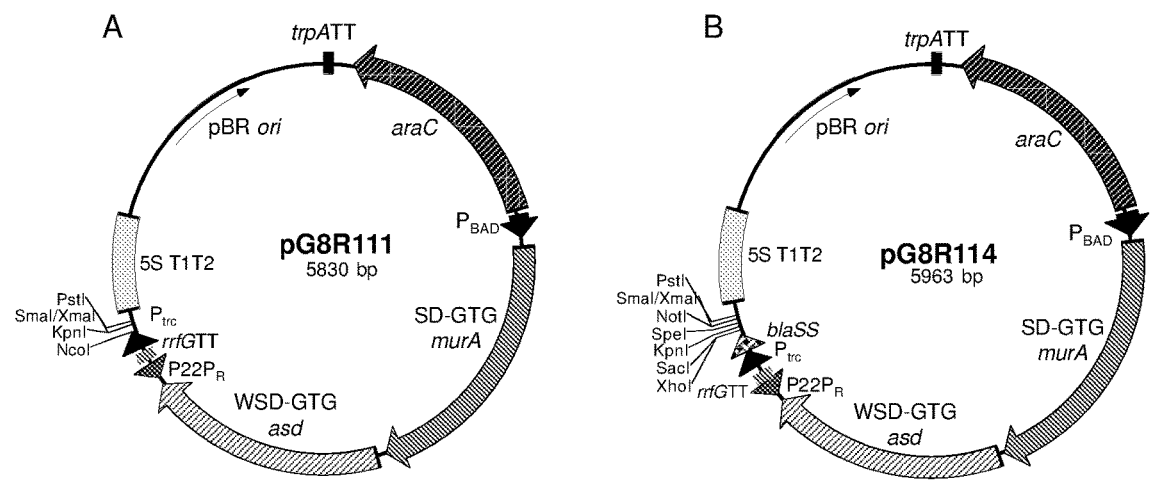
FIG. 2
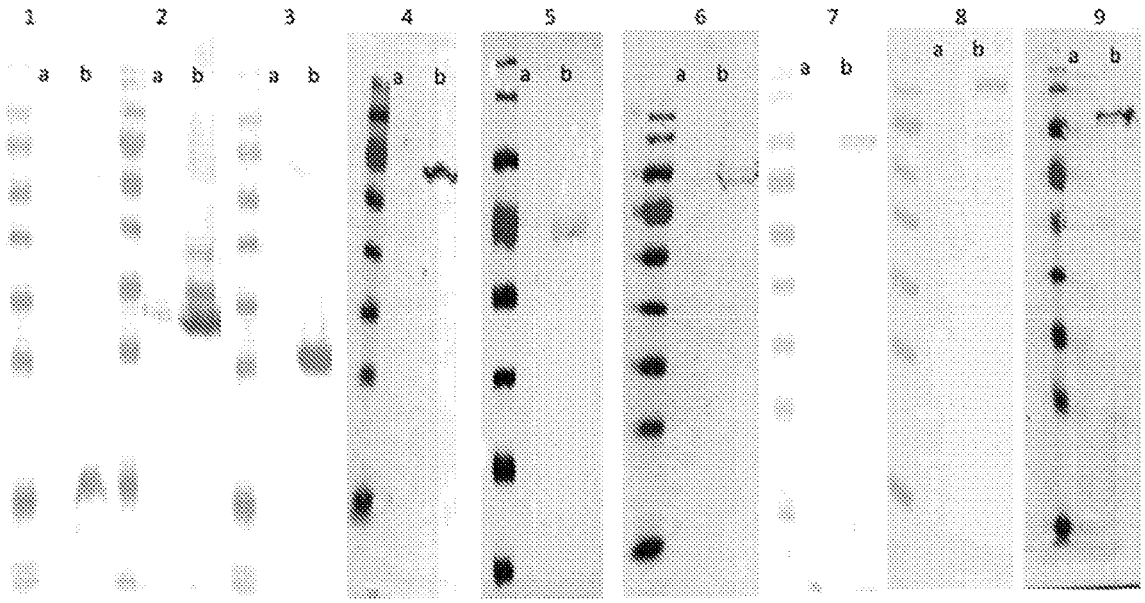

FIG. 3. Regulated delayed lysis plasmid vectors pG8R230 and pG8R262

FIG. 5. Regulated delayed lysis plasmid vectors pG8R65

FIG. 13.
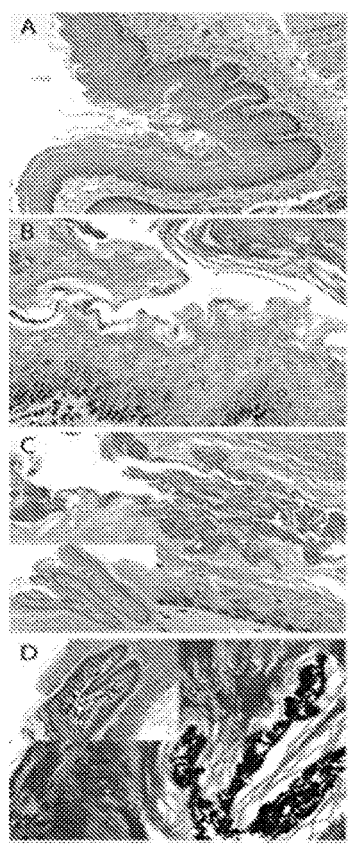
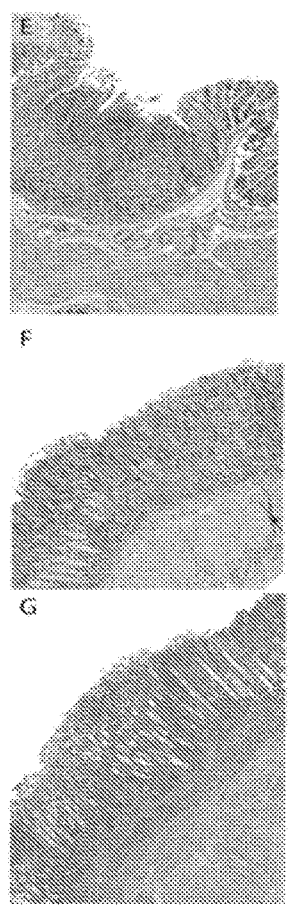
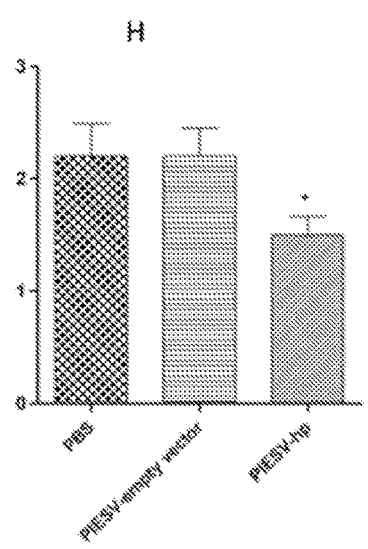

ATTENUATED SALMONELLA SYNTHESIZING ANTIGENS FOR VACCINATING AGAINST HELICOBACTER PYLORI

FEDERAL FUNDING

This invention was made with government support under AI056289, AI1216172 and TR 1001427 awarded by The National Institutes of Health. The government has certain rights in the invention.

REFERENCE TO SEQUENCE LISTING SUBMITTED VIA EFS-WEB

This application includes an electronically submitted sequence listing in .txt format. The .txt file contains a sequence listing entitled "10457-465PC0_ST25" created on Feb. 8, 2021 is 92 KB in size. The sequence listing contained in this .txt file is part of the specification and is hereby incorporated by reference herein in its entirety.

BACKGROUND

*H. pylori* is a Gram-negative bacterium infecting the stomach of more than half of the Earth's human population and is the main cause of gastric pathologies including peptic ulcers, dyspepsia and gastric cancer [1, 2]. Prevalence differs from 10 to >70% [3]. *H. pylori* has been confirmed as a class I carcinogen by the World Health Organization [4]. Gastric cancer is still the second leading cause of death by cancer worldwide [5]. Eradication of *H. pylori* has been frequently considered as an efficient approach to cure peptic ulcer disease in addition to gastric cancer [6]. No doubt, antibiotics are the first choice in treatment. However, *H. pylori* infections present numerous challenges to successful antimicrobial therapy, some of which are limited to *H. pylori* and others are experienced in the treatment of other infections. Challenges arise from the fact that *H. pylori* colonize the stomach where they are protected by a dense mucus layer and an acidic environment. Additionally, the stomach is continuously secreting acid and discharging its contents such that typical therapy would be diluted and washed out [7]. The efficacy of several antimicrobials is greatly reduced at acidic pH and proper pH is needed for them to be effective. *H. pylori* can obtain resistant genotypes and become multi-drug resistant (MDR). Importantly, a recent study has shown that eradication of toxigenic *H. pylori* expressing VacA is not achievable using only antibiotics [8]. In clinical practice, the quick emergence of resistance raised concerns about the correct management of this bacterial infection [9, 10]. Thus, protective and therapeutic vaccines could be an alternative method for antibiotic treatment against *H. pylori* infection. The importance of CD4+ T cells in protective immunity against *H. pylori* has been broadly accepted [11]. Oral administration of recombinant *Salmonella* vectored vaccines could provoke classical Th1-type responses and also induce a significant mucosal SIgA response [12, 13] through transcytosis by micro-fold cells [14] or by direct antigen presentation by interstitial dendritic cells [15]. It was reported that a large number of foreign antigens, synthesized and delivered by live attenuated *Salmonella*, protected animals against a diversity of pathogens including viruses, bacteria and parasites [16]. Oral administration of a live attenuated *Salmonella* vector vaccine synthesizing and delivering *H. pylori* protective antigens could, therefore, be a promising approach to eradicate *H. pylori* infections.

BRIEF DESCRIPTION OF DRAWINGS

FIG. 1. Regulated delayed lysis plasmid vectors pG8R111 (A) and pG8R114 with improved bla SS (B).

FIG. 2. Successful synthesis of nine putative *H. pylori* antigens in *S*. Typhimurium χ12341. (1) Hp-NAP (=NapA), (2) HpaA, (3) UreA, (4) UreB, (5) HopM, (6) BabA, (7) Chimeric Protein, (8) CagA, (9) VacA. (a) Uninduced with IPTG and (b) 2 h after induction with IPTG compared to molecular mass markers. Anti-6xHis monoclonal antibody was used to detect each recombinant protein by western blotting.

FIG. 13. Immunization with the PIESV-Hp mixture reduces inflammation and the number of Gram-positive rod-shaped bacteria in the mouse stomach. Mice immunized with the PIESV-Hp mixture, the PIESV-empty vector and PBS were infected with *H. pylori* SS1 two weeks post last immunization. After thirty days, mice were sacrificed, and stomach tissues were obtained for H&E staining (A) Squamous portion of stomach of mice immunized with the PIESV-Hp mixture showed moderate amounts of hyperkeratosis. (B) Abundant hyperkeratosis with moderate numbers of large rod-shaped bacteria (Gram stain) associated with the keratin layer in mice immunized with PIESV-empty vector. (C) Same as B but with much larger populations of gram-positive bacteria in the keratin layer of mice immunized with PIESV empty vector. (D) Same as C but in mice immunized with PBS. Glandular portion of the stomach with (E) mild, (F) moderate, and (G) severe mucosal and submucosal inflammation in mice immunized with the PIESV-Hp mixture (E & F) or the PIESV empty vector or PBS (G). (H) Reduction in the load of rod-shaped bacteria in immunized mice based of relative frequency scores of 0 (absent), 1 (low), 2 (moderate) and 3 (high).

BRIEF DESCRIPTION OF SEQUENCES

Figure 3:
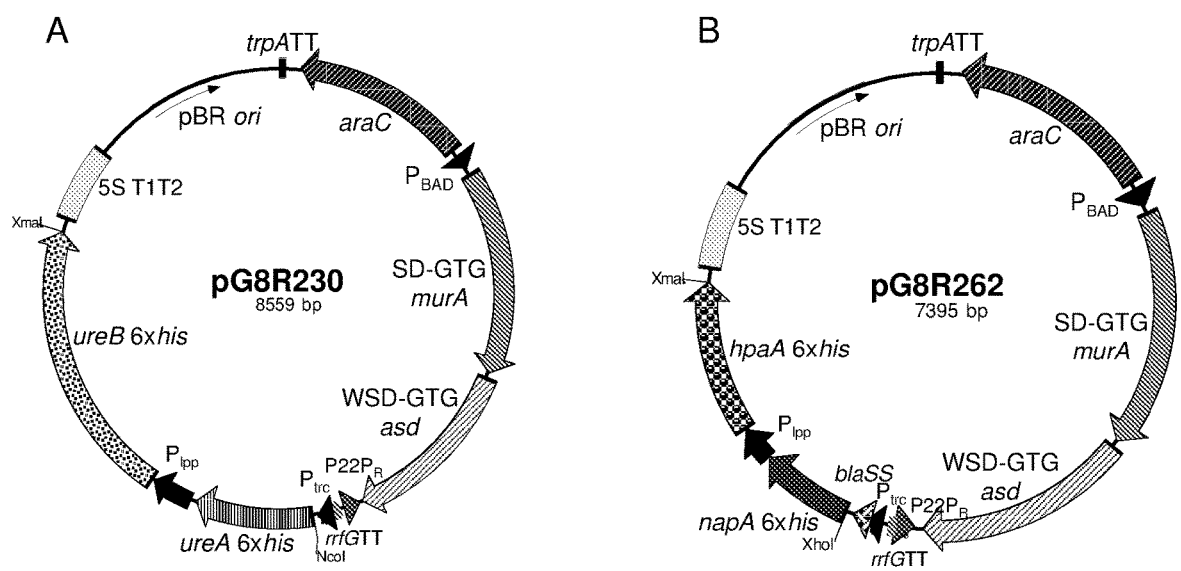
FIG. 3. Regulated delayed lysis plasmid vectors pG8R230 (A) encoding optimized ureA and $P_{lpp}$ ureB *H. pylori* genes inserted into pG8R111 with expression controlled by $P_{trc}$ promoter and pG8R262 (B) encoding optimized napA and $P_{lpp}$ hpaA *H. pylori* genes inserted into pG8R114 with expression controlled by $P_{trc}$ promoter.

SEQ ID NOs: 1-4 show the natural nucleic acid sequence, and optimized nucleic acid and amino acid sequences of HopM antigen, and signal peptide, respectively.

SEQ ID NOs: 5-8 show the natural nucleic acid sequence, and optimized nucleic acid and amino acid sequences of of HpaA antigen and signal peptide, respectively.

SEQ ID NOs: 9-11 show the natural nucleic acid sequence, and optimized nucleic acid and amino acid sequences of of UreA antigen, respectively.

SEQ ID NOs: 12-14 show the natural nucleic acid sequence, and optimized nucleic acid and amino acid sequences of of CagA antigen, respectively.

SEQ ID NOs: 15-20 show the nucleic acid and amino acid sequences of VacA, BabA, and NapA, respectively.

SEQ ID NOs: 21 and 22 show the nucleic acid and amino acid sequences of a chimeric gene and protein, respectively, based on fliD, vacA, ureB, and cagA.

SEQ ID NOs: 23-25 show the natural nucleic acid sequence, and optimized nucleic acid and amino acid sequences of UreB antigen, respectively

DETAILED DESCRIPTION

As disclosed herein, PIESVs have been developed that specifically synthesize heterologous antigens and enhance the induction of immune responses and protection against viruses and bacteria [17, 18]. Such mucosal PIESV delivery induces strong mucosal, systemic and cellular immunities against the targeted pathogen [19-24]. Since *H. pylori* colonize and move through a mucosal body surface, the induction of mucosal immunity dependent on the production of secretory antibodies (SIgA/SIgM) as well as cellular immunity offers the first line of defense against infection with such pathogens [25-30]. Injectable subunit recombinant protein vaccines are unable to induce such mucosal immunity in contrast to PIESVs that induce mucosal, systemic and cellular immunities that can block infections and preclude disease [18, 31-38]. Here, disclosed is PIESVs synthesizing *H. pylori* protective antigens against *H. pylori* SS1 infection.

Definitions

As used herein the specification, "a" or "an" may mean one or more, unless clearly indicated otherwise. As used herein in the claims, when used in conjunction with the word "comprising," the words "a" or "an" may mean one or more than one.

The terms "attenuated" or "attenuation" as used herein refer to the process of rendering certain pathogen virulence attributes needed to cause diseases less able to cause such disease symptoms. In one example, attenuation involves imparting an attenuation mutation in the pathogen.

The term "attenuating mutation" refers to a mutation imparted into a pathogen that reduces infectivity, virulence, toxicity, induction of disease symptoms, and/or impairment of a subject upon administration of the pathogen (e.g. PIESV strain). Examples of attenuating mutations include those mutations that facilitate lysis in vivo (e.g. impairing synthesis of essential constituents of peptidoglycan layer), reduce or impair synthesis of LPS or other cell-surface components, and one or more mutations that provide auxotrophy (e.g. dependence on an amino acid, purine, pyrimidine, or vitamin for growth).

The term "attenuated derivative of an invasive pathogenic microorganism" refers to a microorganism that is derived from an invasive pathogenic microorganism but which has been genetically modified to be attenuated.

As used herein, "codon" means, interchangeably, (i) a triplet of ribonucleotides in an mRNA which is translated into an amino acid in a polypeptide or a code for initiation or termination of translation, or (ii) a triplet of deoxyribonucleotides in a gene whose complementary triplet is transcribed into a triplet of ribonucleotides in an mRNA which, in turn, is translated into an amino acid in a polypeptide or a code for initiation or termination of translation. Thus, for example, 5'-TCC-3' and 5'-UCC-3' are both "codons" for serine, as the term "codon" is used herein.

The term "codon optimized" or "codon optimization" as used herein refers to enhancing the ability of the antigen encoding sequence to be expressed in the *Salmonella* vaccine strain by selecting codons that are used for highly expressed genes in *Salmonella*.

Such codon optimization also includes changing the GC content of the antigen encoding sequence to be similar to that used for *Salmonella* (i.e., ~52% GC). In addition, the codon optimization can also be used to enhance the stability of the mRNA encoded by the antigen encoding sequence so as to be less likely to be degraded by RNases.

The term "delayed attenuation" as used herein refers to a means of gene regulation such that the attenuation attribute is not expressed during growth of the vaccine strain or during its administration to an animal host but is not expressed after the vaccine enters the animal host and is manifest as a consequence of vaccine cell division in vivo with gradual dilution of the virulence gene product by at least half at each cell division in vivo.

The term "high level synthesis" refers to a means of synthesizing a protein antigen at a level that exceeds that level of synthesis that would be synthesized by a chromosomal gene encoding that antigen and can be achieved by encoding the antigen gene on a multi-copy plasmid and/or by placing the antigen encoding sequence under the control of a promoter known to cause gene product synthesis at an elevated level greater than would be caused by using the native promoter for that antigen encoding gene.

The term "balanced-lethal plasmid-host" is the design of the plasmid-host composition such that survival of the host is dependent on the maintenance of the plasmid such that loss of the plasmid results in death of the host. (See Nakayama, K., Kelly, S. & Curtiss, R. Construction of an ASD+ Expression-Cloning Vector: Stable Maintenance and High Level Expression of Cloned Genes in a *Salmonella* Vaccine Strain. *Nat Biotechnol* 6, 693-697 (1988) or Galán J E, Nakayama K, Curtiss R 3rd. Cloning and characterization of the asd gene of *Salmonella* typhimurium: use in stable maintenance of recombinant plasmids in *Salmonella* vaccine strains. Gene. 1990 Sep. 28; 94(1):29-35, whose teachings are incorporated by reference).

The term "regulated delayed lysis" refers to a construction in which the expression of one or more genes specifying synthesis of peptidoglycan precursors such as but not limited to diaminopimelic acid and muramic acid are regulated by a sugar-dependent process such that the genes are expressed in the presence of a sugar such as but not limited to arabinose supplied during cultivation of the strain and cease to be expressed in vivo since the sugar is absent to result in lysis as a consequence of cell division of the PIESV strain in vivo. The genes conferring the regulated delayed lysis phenotype may be either chromosomal and/or plasmid encoded.

The term "regulated delayed lysis plasmid" refers to a construction in which the expression of one or more genes specifying synthesis of peptidoglycan precursors such as but not limited to diaminopimelic acid and muramic acid that are regulated by a sugar-dependent process are located on a plasmid vector encoding synthesis of one or more protective antigens.

The terms "animal host", "host" or "subject" are used interchangeably and refers to a human or nonhuman mammal into which an attenuated derivative of an invasive pathogenic microorganism has been administered. In a specific embodiment, the animal host is a human.

The term "operably linked" as used herein means that one nucleic acid sequence is linked to another nucleic acid sequence, and therefore the function or expression thereof is influenced by the linked nucleic acid sequence.

The term "administering" or "administration" of an agent as used herein means providing the agent to a subject using any of the various methods or delivery systems for administering agents or pharmaceutical compositions known to those skilled in the art. Agents described herein may be administered by oral, intradermal, intravenous, intramuscular, intraocular, intranasal, intrapulmonary, epidermal, subcutaneous, mucosal, or transcutaneous administration.

A used herein, the term "immune response" includes a response by a subject's immune system to a vaccine Immune responses include both cell-mediated immune responses (responses mediated by antigen-specific T cells and non-specific cells of the immune system) and humoral immune responses (responses mediated by antibodies present in the plasma lymph, and tissue fluids). The term "immune response" encompasses both the initial responses to an immunogen as well as memory responses that are a result of "acquired immunity."

The term "Protective Immunity Enhanced *Salmonella* Vaccine" or "(PIESV)" refers to a vector strain that has been engineered to synthesize and deliver an immunogen (e.g. *Helicobacter* protein or other type of antigen).

The term "Protective Immunity Enhanced *Salmonella* Vaccine vector strain" or "PIESV vector strain" refers to a strain of *Salmonella* that has one or more attenuating mutations and is capable of being engineered to express an immunogen insertion.

The term "protective immunity" as used herein refers to induction of an immune response upon administration of a vaccine sufficient to confer protection against a pathogen.

As used herein, the term "vaccine" refers to an immunogen or a composition comprising an immunogen that elicits an endogenous immune response in a subject (e.g., a human or animal) The endogenous immune response may result in, for example, the switching of a Th1 biased immune response to a Th2 biased immune response, the activation or enhancement of T effector cell responses and/or the reduction of T regulatory cell response, the activation of antigen-specific naive lymphocytes that may then give rise to antibody-secreting B cells or antigen-specific effector and memory T cells or both, and/or the direct activation of antibody-secreting B cells. Typically, a vaccine provides for protective immunity against a pathogen.

The term "biologically active fragment" or "biologically active variant" refers to a fragment or variant of a sequence that maintains its biological activity. In the context of *H. pylori* antigen sequences, a biologically active fragment or biologically active variant is a fragment or variant of an antigen amino acid sequence that elicits an immune response in a host.

The term "variant" as used herein refers to a nucleic acid sequence or amino acid sequence that possesses at least about 85, 90, 95, 96, 97, 98 or 99 percent sequence identity to another nucleic acid sequence or amino acid sequence, respectively.

The term "sequence identity" or "identity," as used herein in the context of two polynucleotides or polypeptides, refers to the residues in the sequences of the two molecules that are the same when aligned for maximum correspondence over a specified comparison window.

As used herein, the term "percentage of sequence identity" or "percent sequence identity" may refer to the value determined by comparing two optimally aligned sequences (e.g., nucleic acid sequences or polypeptide sequences) of a molecule over a comparison window, wherein the portion of the sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleotide or amino acid residue occurs in both sequences to yield the number of matched positions, dividing the number of matched positions by the total number of positions in the comparison window, and multiplying the result by 100 to yield the percentage of sequence identity. A sequence that is identical at every position in comparison to a reference sequence is said to be 100% identical to the reference sequence, and vice-versa. The term "about" with respect to a numerical value of a sequence length means the stated value with a +/- variance of up to 1-5 percent. For example, about 30 contiguous nucleotides means a range of 27-33 contiguous nucleotides, or any range in between. The term "about" with respect to a numerical value of percentage of sequence identity means the stated percentage value with a +/− variance of up to 1-3 percent rounded to the nearest integer. For example, about 90% sequence identity means a range of 87-93%. However, the percentage of sequence identity cannot exceed 100 percent. Thus, about 98% sequence identity means a range of 95-100%.

Overview

Salmonella has been extensively investigated among bacterial genera for delivering recombinant protective antigens and DNA vaccine vectors due to its capability to be delivered mucosally, thereby stopping the use of needles for immunization [18]. Live attenuated bacterial vaccines preferably comprise strains that possess two or more stable attenuating mutations dispersed in the bacteria chromosome and plasmids (without antibiotic-resistant markers) into which genes encoding heterologous antigens from microbial pathogens can be inserted. The attenuating mutations should be in genes encoding essential components of bacterial cell structures or biosynthetic pathways for crucial nutrients that are not freely available in any environment that the PIESV may reside outside of the laboratory [18].

In this study, PIESVs were employed to deliver and synthesize nine recombinant protective antigens of *H. pylori*. Mice were immunized with each construct alone or a combination of them. After that, Based on the results obtained, a series of plasmids were constructed encoding for synthesis of two antigens for delivery by the PIESV construct. Immunization of mice with mixtures of these constructs revealed the best antigen combinations. It was found that immunization of mice with the combination of two plasmids each carrying genetic sequences encoding two different antigens (totally four antigens including HpaA, NapA (also termed Hp-NAP), UreA and UreB) provided statistically significant protection against *H. pylori* SS 1 challenge infection. These results not only emphasize the efficacy of the cocktail vaccine to provide sterile protection but also show the strong applicability of PIESVs, especially the improved plasmids used in this system. The induction of protective immunity by a PIESV delivering multiple antigens in the hostile environment of the stomach was a new and surprising result. To unravel the mechanism of protection provided by the cocktail vaccine, the humoral and cellular immune responses induced by immunization were measured and compared to mice immunized with a combination of the two PIESV-empty vector strains or PBS.

Although the detailed mechanism by which immunization protects against *H. pylori* remains to be clarified, the vital role of cell-mediated immunity has been well-known by showing that protection against *H. pylori* infection can be obtained even in the lack of B cells [77]. In this regard, it has been shown that immunological eradication of *H. pylori* usually is contingent on Th1-type responses and IFN-γ, the prototype Th1 cytokine, playing a main role in the control of *H. pylori* infection by activating macrophages and changing antibody responses toward protective IgG2c in C57BL/6 mice [78]. The data herein shows very high levels of Th1 (IL-12 and IFN-γ) and Th17 (IL-17) cytokines during recall responses of T cells from mice immunized with the cocktail mixture of PIESV strains each delivering two antigens each.

Consistent with the proliferative response, T cells from mice immunized with the vaccine, produced higher levels of IFN-γ in response to each component of the cocktail than mice that received PBS or the two empty-vector PIESV strains alone. In addition, T cells of immunized mice produced high levels of IL-6 when re-exposed to the immunizing antigens. IL-6 is deemed one of the mediators directing the transition between innate and adaptive immunity. Its production is mostly targeted by the PAMP-mediated TLR signaling cascade and as a result, IL-6 gene-deficient mice display impaired defense against some bacterial infections [79]. Thus, it is possible that this cytokine plays a key role in providing immunity against *H. pylori*. Besides, Th17 cells and their effector cytokines seem to mediate immunity against numerous infections, mainly those caused by extracellular pathogens like *H. pylori* [80]. Th17 immune responses include neutrophil recruitment, secretion of antimicrobial peptides, and Th1-mediated protection driven by IL-17 [81,82]. In the study described in the Examples herein, a significant amount of IL-17 was measured after the re-stimulation of T cells with each recombinant antigen in the cocktail vaccine.

Consistent with the proliferative response, T cells from mice immunized with the cocktail mixture PIESV vaccine delivering four protective antigens, produced higher levels of IFN-γ in response to each component of the cocktail than mice that received PBS or a mixture of the empty vector PIESV strains. In addition, T cells of immunized mice produced high levels of IL-6 when re-exposed to the immunizing antigens. IL-6 is deemed one of the mediators directing the transition between innate and adaptive immunity. Its production is mostly targeted by the PAMP-mediated TLR signaling cascade and as a result, IL-6 gene-deficient mice display impaired defense against some bacterial infections (79). Thus, it is possible that this cytokine plays a key role in providing immunity against *H. pylori* infection. Besides, Th17 cells and their effector cytokines seem to mediate immunity against numerous infections, mainly those caused by extracellular pathogens like *H. pylori* (80). Th17 immune responses include neutrophil recruitment, secretion of antimicrobial peptides, and Th1-mediated protection driven by IL-17 (81, 82). Thus, a significant amount of IL-17 was measured after the re-stimulation of T cells with each recombinant antigen in the cocktail vaccine. The level of circulating IL-22 cytokine also spiked after immunization with the PIESV-Hp mixture and the PIESV-empty vector mixture compared to the non-immunized control group only receiving PBS. It seems that *Salmonella* vaccines are able to induce the production of circulating of IL-22 that has been shown to play an important role in protecting the gut tissue integrity and enhance disease lessening through chronic *Salmonella* Infection (83).

To gain insight further into the underlying mechanism, the kinetics of antibody production against each component of the vaccine were observed and it was found that both antigen-specific IgG1 and IgG2c antibodies were produced. Notably, the IgG1/IgG2c ratio also showed that the response elicited in immunized mice had a strong Th1 bias. Since IFN-γ and IgG2c are markers of the Th1 type of immune response in C57BL/6 mice, and synthesis of IgG1 can be controlled by Th2 clones, seeing the results obtained from cytokine assays and these findings, one might conclude that the immune responses elicited by the vaccine was of a mixed Th1/Th17 type [78].

The mucosal immune responses produced by immunization were measured. With that goal, the gastric IgA secretion into the gastric mucosa and immune-mediated inflammation were measured in immunized mice. Compared to control immunized mice, immunized mice elicited significant levels of each antigen-specific gastric IgA. These surprising findings indicate that immunization with PIESV strains delivering heterologous antigens efficiently stimulated gastric mucosal immune responses.

The responses of other components of the immune system in immunized mice against infection by *H. pylori* were also investigated. Thus, synthesis of several antimicrobial peptides and chemokines were assessed. The results only showed that production of CXCL2 was significantly upregulated in the stomach of immunized mice. CXCL2 is also a mighty neutrophil chemoattractant and is involved in numerous immune responses comprising wound healing, cancer metastasis, and angiogenesis [84]. This result shows that the composite vaccine is capable to induce recall innate as well as acquired immunity. Systemic immune responses were also studied in immunized mice. Although in proliferation assays, CD8+ T cells were propagated more than CD4+ T cells in response to re-stimulation, the number of CD4+ T cells but not CD8+ T cells expressing IFN-γ increased after infection with *H. pylori* SS1 in the spleen of immunized mice. This supports the IgG titer data that indicate that systemic immunity was skewed towards a Th1 response after immunization. However, local immunity in the stomach tissues may be more dependent on CD8+ T cells. Further investigation is therefore needed to clarify the contribution of CD4 versus CD8 T cells in the stomach tissue.

The result of histopathology measurements showed an increased number of gram-positive rod-shaped bacteria in the stomach of control groups compared to the immunized group. Although the species of this population was not verified, this finding shows the role of *H. pylori* infection in increasing the number of other gram-positive bacilli which might have a role in worsening the stomach complications caused by *H. pylori* infection. In this regard, it has been indicated that gastric colonization by non-*H. pylori* bacteria, such as Bacteroides, Actinobacteria, Fusobacteria, Firmicutes, and Proteobacteria, could influence the risk for gastric cancer [85-89]. Notably, the vaccine embodiments disclosed herein not only provided sterile protection in seven out of 10 of the immunized mice but it also caused a significant reduction in the titer of gram-positive rod-shaped bacteria.

In sum, a *S.* Typhimurium-based live vaccine including the delivery of four protective antigens of *H. pylori* confers significantly high protection against *H. pylori* infection in mice. Additionally, immunological studies showed the induction of both specific acquired immune responses against each antigen and the innate immunity responses. The findings herein also showed the increased number of gram-positive rod-shaped bacteria in the presence of *H. pylori* in control groups compared to the immunized mice.

Plasmid

An attenuated microorganism as described herein that is capable of the regulated expression of at least one nucleic acid sequence encoding a *Helicobacter* antigen may also comprise, in part, a plasmid vector. The plasmid vector comprises a nucleic acid sequence encoding at least one *Helicobacter* antigen operably linked to a promoter. The promoter is regulated by the chromosomally encoded repressor, such that the expression of the nucleic acid sequence encoding an antigen is repressed during in vitro growth of the microorganism, but the microorganism is capable of high-level synthesis of the antigen in an animal or human host.

As used herein, "plasmid vector" refers to an autonomously replicating nucleic acid unit. The term plasmid vector is used in its broadest sense and includes many types of vectors. Examples include bacteriophage viral vectors, cosmid, phasmid, in addition to conventional plasmid vectors. It is noted that bacteriophage viral vectors include integrated prophages or plasmid derivatives of phages (e.g. lambda dv is a plasmid derivative of lambda phage that can be used as a vector). Also, it is noted that some bacteriophages infect bacteria as prophages but exist as in plasmid form upon infection into the bacterium (e.g. P1 bacteriophage of *Shigella* and *E. coli.*).

As is well known in the art, plasmids and other vectors may possess a wide array of promoters, multiple cloning sequences, transcription terminators, etc., and vectors may be selected so as to control the level of expression of the nucleic acid sequence encoding an antigen by controlling the relative copy number of the vector. In some instances, in which the vector might encode a surface localized adhesin as the antigen, or an antigen capable of stimulating T-cell immunity, it may be preferable to use a vector with a low copy number such as at least two, three, four, five, six, seven, eight, nine, or ten copies per bacterial cell. A non-limiting example of a low copy number vector may be a vector comprising the pSC101 ori.

In other cases, an intermediate copy number vector might be optimal for inducing desired immune responses. For instance, an intermediate copy number vector may have at least 10, 11, 12, 13, 14, 15, 16, 17, 18, 19, 20, 21, 22, 23, 24, 25, 26, 27, 28, 29, or 30 copies per bacterial cell. A non-limiting example of an intermediate copy number vector may be a vector comprising the p15A ori.

In still other cases, a high copy number vector might be optimal for the induction of maximal antibody responses or mucosal immune responses. A high copy number vector may have at least 31, 35, 40, 45, 50, 55, 60, 65, 70, 75, 80, 85, 90, 95, or 100 copies per bacterial cell. In some embodiments, a high copy number vector may have at least 100, 125, 150, 175, 200, 225, 250, 275, 300, 325, 350, 375, or 400 copies per bacterial cell. Non-limiting examples of high copy number vectors may include a vector comprising the pBR ori or the pUC ori.

Additionally, vector copy number may be increased by selecting for mutations that increase plasmid copy number. These mutations may occur in the bacterial chromosome but are more likely to occur in the plasmid vector.

Preferably, vectors used herein do not comprise antibiotic resistance markers to select for maintenance of the vector.

A vector may comprise one or more than one nucleic acid sequence encoding a *Helicobacter* antigen, whether regulated or not, as detailed above (SEQ ID NOs: 1-23).

Attenuation of the Recombinant Bacterium

In each of the above embodiments, the microorganism capable of regulated expression of *Helicobacter* antigens also is attenuated. "Attenuated" refers to the state of the microorganism (e.g., bacterium) wherein the microorganism has been weakened from its wild-type fitness by some form of recombinant or physical manipulation. This may include altering the genotype of the microorganism to reduce its ability to cause disease. However, the bacterium's ability to colonize the gut (in the case of *Salmonella*) and internal effector lymphoid tissues to induce immune responses is, preferably, not substantially compromised. For instance, in one embodiment, regulated attenuation allows the recombinant microorganism to express one or more nucleic acids encoding products important for the microorganism to withstand stresses encountered in the host after immunization. This allows efficient invasion and colonization of lymphoid tissues before the recombinant microorganism is regulated to display the attenuated phenotype.

In one embodiment, a microorganism may be attenuated by regulating LPS O-antigen synthesis. In another embodiment, a recombinant microorganism may be attenuated as described below. In which case, both regulated attenuation and regulated expression of a *Helicobacter* antigen encoding sequence may be dependent upon an arabinose regulatable system. Consequently, the concentration of arabinose needed for optimal expression of the regulated enteric antigen encoding sequence may not be the same as the concentration for optimal expression of attenuation. In an exemplary embodiment, the concentration of arabinose for the optimization of both regulated attenuation and regulated expression of sequences encoding antigen will be substantially the same. In other embodiments, such regulation of attenuation or regulation of gene expression may be dependent on other sugars such as mannose or rhamnose, which are unavailable in a non-phosphorylated form in vivo.

Accordingly, the promoter and/or the nucleic acid sequence encoding an attenuation protein may be modified to optimize the system. Methods of modification are detailed above. Briefly, for example, the SD ribosome binding sequence may be altered, and/or the start codon may be altered from ATG to GTG for the nucleic acid sequences encoding the virulence protein, so that the production levels of the virulence protein are optimal for both the regulated attenuation phenotype and the regulated expression when growing strains with a given concentration of arabinose. In addition, these attenuating nucleic acid sequences may be regulated by other systems using well-established protocols known to one of skill in the art. For example, they may be regulated using promoters dependent on addition of maltose, rhamnose, or xylose rather than arabinose.

Other methods of attenuation are known in the art. For instance, attenuation may be accomplished by altering (e.g., deleting) native nucleic acid sequences found in the wild-type bacterium. For instance, if the microorganism is Salmonella, non-limiting examples of nucleic acid sequences which may be used for attenuation include: a pab nucleic acid sequence, a pur nucleic acid sequence, an aro nucleic acid sequence, asd, a dap nucleic acid sequence, nadA, pncB, galE, pmi, fur, rpsL, ompR, htrA, hemA, cdt, cya, crp, dam, phoP, phoQ, rfc, rfaH, waaL, poxA, galU, mviA, sodC, recA, ssrA, sirA, sifA, inv, hilA, rpoE, flgM, tonB, slyA, and any combination thereof. Exemplary attenuating mutations may be aroA, aroC, aroD, cdt, cya, crp, phoP, phoQ, ompR, galE, and htrA.

In certain embodiments, the above nucleic acid sequences may be placed under the control of a sugar regulated promoter wherein the sugar is present during in vitro growth of the recombinant bacterium, but substantially absent within an animal or human host. The cessation in transcription of the nucleic acid sequences listed above would then result in attenuation and the inability of the recombinant microorganism to induce disease symptoms.

The microorganism may also be modified to create a balanced-lethal host-vector system, although other types of systems may also be used (e.g., creating complementation heterozygotes). For the balanced-lethal host-vector system, the microorganism may be modified by manipulating its ability to synthesize various essential constituents needed for synthesis of the rigid peptidoglycan layer of its cell wall. In one example, the constituent is diaminopimelic acid (DAP). Various enzymes are involved in the eventual synthesis of DAP. In one example, the microorganism is modified by using a ΔasdA mutation to eliminate the bacterium's ability to produce β-aspartate semialdehyde dehydrogenase, an enzyme essential for the synthesis of DAP. One of skill in the art can also use the teachings of U.S. Pat. No. 6,872,547 for other types of mutations of nucleic acid sequences that result in the abolition of the synthesis of DAP. These nucleic acid sequences may include, but are not limited to, dapA, dapB, dapC, dapD, dapE, dapF, and asd.

Other modifications that may be employed include modifications to a bacterium's ability to synthesize D-alanine or to synthesize D-glutamic acid (e.g., Δmurl mutations), which are both unique constituents of the peptidoglycan layer of the bacterial cell wall. In any of these cases, plasmid vectors can possess the wild-type gene to complement the deleted chromosomal gene to establish the balanced-lethal vector-host system. This system is stably maintained in vivo due to the absence of the required nutrient imposed by the chromosomal mutation with loss of the plasmid resulting in death of the vaccine cell.

Yet another balanced-lethal host-vector system comprises modifying the microorganism such that the synthesis of an essential constituent of the rigid layer of the bacterial cell wall is dependent on a nutrient (e.g., arabinose) that can be supplied during the growth of the microorganism. For example, a microorganism may comprise the $\Delta P_{murA}$::TT araC $P_{araBAD}$ murA deletion-insertion mutation. This type of mutation makes synthesis of muramic acid (another unique essential constituent of the peptidoglycan layer of the bacterial cell wall) dependent on the presence of arabinose that can be supplied during growth of the microorganism in vitro.

When arabinose is absent, however, as it is in an animal or human host, the essential constituent of the peptidoglycan layer of the cell wall is not synthesized. This mutation represents an arabinose dependent lethal mutation. In the absence of arabinose, synthesis of muramic acid ceases and lysis of the microorganism occurs because the peptidoglycan layer of the cell wall is not synthesized. It is not possible to generate ΔmurA mutations because they are lethal. The necessary nutrient, a phosphorylated muramic acid, cannot be exogenously supplied because enteric bacteria cannot take the nutrient up from the media. Recombinant bacteria with a $\Delta P_{murA}$::TT araC $P_{araBAD}$ murA deletion-insertion mutation grown in the presence of arabinose exhibit effective colonization of effector lymphoid tissues after oral vaccination prior to undergoing lysis due to the inability to synthesize muramic acid.

Similarly, various embodiments may comprise the araC $P_{araBAD}$ c2 cassette inserted into the asd nucleic acid sequence that encodes aspartate semialdehyde dehydrogenase. Since the araC nucleic acid sequence is transcribed in a direction that could lead to interference in the expression of adjacent nucleic acid sequences and adversely affect vaccine strain performance, a transcription termination (TT) sequence is generally inserted 3' to the araC nucleic acid sequence. The chromosomal asd nucleic acid sequence is typically inactivated to enable use of plasmid vectors encoding the wild-type asd nucleic acid sequence in the balanced-lethal host-vector system. This allows stable maintenance of plasmids in vivo in the absence of any drug resistance attributes that are not permissible in live bacterial vaccines. In some of these embodiments, the wild-type asd nucleic acid sequence may be encoded by the vector described above.

In one embodiment, ΔasdA27::TT araC $P_{araBAD}$ c2 has an improved SD sequence and a codon optimized c2 nucleic acid sequence. The C2 repressor synthesized in the presence of arabinose is used to repress nucleic acid sequence expression from P22 $P_R$ and $P_L$ promoters. In another embodiment, ΔasdA27::TT araC $P_{araBAD}$ c2 has the 1104 base-pair asd nucleic acid sequence deleted (1 to 1104, but not including the TAG stop codon) and the 1989 base-pair fragment containing T4 ipIII TT araC $P_{araBAD}$ c2 inserted. The c2 nucleic acid sequence in ΔasdA27::TT araC $P_{araBAD}$ c2 has a SD sequence that was optimized to TAAGGAGGT. It also has an improved $P_{araBAD}$ promoter such that the −10 sequence is improved from TACTGT to TATAAT. Furthermore, it has a codon optimized c2 nucleic acid sequence, in which the second codon was modified from AAT to AAA.

In further embodiments, the microorganism may be attenuated by regulating the murA nucleic acid sequence encoding the first enzyme in muramic acid synthesis and the asd nucleic acid sequence essential for DAP synthesis. These embodiments may comprise the chromosomal deletion-insertion mutations ΔasdA27::TT araC $P_{araBAD}$ c2 and $\Delta P_{murA25}$::TT araC $P_{araBAD}$ murA. This host-vector grows in LB broth with 0.1% L-arabinose, but is unable to grow in or on media devoid of arabinose since it undergoes cell wall-less death by lysis. Either GTG or TTG start codons for the murA and asd nucleic acid sequences are important to decrease translation efficiency on multi-copy plasmids. For instance, plasmid vector pG8R114 contains the murA nucleic acid sequence (with altered start codon sequences to decrease translation efficiency) under the control of an araC $P_{araBAD}$ promoter. Also, the second nucleic acid sequence under the direction of this promoter is the asd nucleic acid sequence (with altered start codon sequences to decrease translation efficiency). The P22 $P_R$ promoter is in the anti-sense direction of both the asd nucleic acid sequence and the murA nucleic acid sequence. The P22 $P_R$ is repressed by the C2 repressor made during growth of the strain in media with arabinose (due to the ΔasdA27::TT araC $P_{araBAD}$ c2 deletion-insertion). However, C2 concentration decreases due to cell division in vivo to cause $P_R$ directed synthesis of anti-sense mRNA to further block translation of asd and murA mRNA. The araC $P_{araBAD}$ sequence is also not from E. coli B/r as originally described but represents a sequence derived from E. coli K-12 strain χ289 with tighter control and less leakiness in the absence of arabinose. In the preferred embodiment, transcription terminators (TT) flank all of the domains for controlled lysis, replication, and expression so that expression in one domain does not affect the activities of another domain. As a safety feature, the plasmid asd nucleic acid sequence does not replace the chromosomal asd mutation since they have a deleted sequence in common, consequently, the E. coli murA nucleic acid sequence was used in the plasmid instead of using the Salmonella murA nucleic acid sequence. The recombinant microorganism of this embodiment is avirulent at oral doses in excess of $10^9$ CFU to BALB/c mice. In addition to being fully attenuated, this construction exhibits complete biological containment with no in vivo recombinant bacteria survivors detectable after 21 days and no recombinant bacteria survivors during or after excretion. This property enhances vaccine safety and minimizes potential for immunization of those not intended to be immunized or in humans not elected to be immunized.

Regulatable Promoter

The native promoter of a nucleic acid encoding an attenuation protein is replaced with a regulatable promoter operably linked to the nucleic acid sequence encoding an attenuation protein. The term "operably linked," is defined above.

The regulatable promoter used herein generally allows transcription of the nucleic acid sequence encoding the attenuation protein while in a permissive environment (i.e. in vitro growth), but cease transcription of the nucleic acid sequence encoding an attenuation protein while in a non-permissive environment (i.e. during growth of the microorganism in an animal or human host). For instance, the promoter may be responsive to a physical or chemical difference between the permissive and non-permissive environment. Suitable examples of such regulatable promoters are known in the art and detailed above.

In some embodiments, the promoter may be responsive to the level of arabinose in the environment, as described above. In other embodiments, the promoter may be responsive to the level of maltose, rhamnose, or xylose in the environment, as described above. The promoters detailed herein are known in the art, and methods of operably linking them to a nucleic acid sequence encoding an attenuation protein are known in the art.

Helicobacter Antigens

Various Helicobacter antigens and sequences may be implemented in the vaccine system and microorganism disclosed herein. Examples of Helicobacter antigens that may be implemented include but are not limited to (1) Hp-NAP (also termed NapA) (e.g. SEQ ID No. 20), (2) HpaA (e.g. SEQ ID NO. 7), (3) UreA (e.g. SEQ ID NO. 11), (4) UreB (e.g. SEQ ID NO. 25), (5) HopM (e.g. SEQ ID NO. 3), (6) BabA (e.g. SEQ ID NO. 18), (7) Chimeric Protein (e.g. SEQ ID NO. 22), (8) CagA (e.g. SEQ ID NO. 14), (9) VacA (e.g. SEQ ID NO. 16) antigens. Nucleic acid and amino acid sequences relating to the aforementioned 1-9 antigens are provided in SEQ ID NOs 1-25. The sequences of these antigens are known and provided in the cited literature. In preparation for vector construction, we do a complete bioinformatic analysis of all structural properties of each protein and the structure of the transcribed mRNA analyzed to then modify DNA codons to enhance stability of mRNA and efficiency of translation in Salmonella. Sometimes protein engineering may be conducted to delete sequences that interfere with stability or synthesis by the PIESV vector strain that impair growth and that are not likely important for immunogenicity. In certain embodiments, nucleic acid sequences encoding the aforementioned nine Helicobacter antigens may include the native sequences of the foregoing 1-9 antigens or codon optimized versions of these 1-9 antigens. In specific examples, embodiments relate to the Helicobacter antigens (1-9 above), or biologically active fragments or biologically active variants of these antigens, or nucleic acid acids encoding the same. Thus, nucleic acid sequences encoding a given antigen may be incorporated into engineered vectors as an expression construct for expression in a host.

For Helicobacter antigens without native signal sequences, the commercially synthesized DNA sequences were most often inserted into pG8R111 (pBR ori), or optionally, pYA4589 (p15A ori). For those proteins with a native signal sequence, the native signal sequence is removed, and the codon-optimized sequence lacking the native SS is inserted into the pG8R114 (pBR ori) and pG8R113 (p15A ori) vectors with the improved bla SS (43) to maximize antigen synthesis levels and secretion to enhance production of immunogenic outer membrane vesicles. We also insert sequences without their native signal peptides into the T3SS vector pG8R110 (p15A ori).

Secretory Signals

As taught herein, secretory signal sequences may be included in the plasmid vectors to direct delivery of the expressed sequence out of the cell. These include secretory signal sequences for the type 2 and type 3 secretory systems. The improved bla SS used in pG8R114 and other plasmid vectors is described in Jiang et al. [43] and the sequence for the T3SS with fusion to the N-terminal 80 amino acids of the SopE protein as used in pG8R110 is given in Juarez et al. [64].

Biological Containment

Under certain embodiments, a live attenuated microorganism may possess the potential to survive and multiply if excreted from a host. This leads to the possibility that individuals not electing to be immunized may be exposed to the attenuated microorganism. It is also possible that attenuated microorganisms that survive and persist in an animal host destined for food consumption might contaminate the meat during slaughter and be transmitted through the food chain to human consumers. Consequently, in certain embodiments, an attenuated microorganism of the invention may comprise one or more mutations that decrease, if not preclude, the ability of *Salmonella* vaccines to persist in the GI tract of animals.

In some embodiments, the attenuated microorganism may comprise a method of regulated delayed lysis in vivo that prevents bacterial persistence in vivo and survival if excreted. These mutations include: Δ(wza-wcaM)-8 that prevents synthesis of colanic acid and other polysaccharide capsules that protect lysing cells from display of complete lysis and thus enhances the level of biological containment afforded by using the regulated delayed lysis in vivo attribute. ΔasdA27::TT araC $P_{araBAD}$ c2 insertion-deletion mutation to impose a requirement for the peptidoglycan constituent DAP and Δ$P_{murA25}$::TT araC $P_{araBAD}$ murA insertion-deletion mutation as a conditional-lethal mutation blocking synthesis of the peptidoglycan constituent muramic acid. The latter two mutations are typically complemented by a regulated delayed lysis plasmid vector such as pG8R110, pG8R111 and pG8R114 (FIG. 1) that have an arabinose-dependent expression of asdA and murA genes. An attenuated microorganism comprising such mutations grows normally in the presence of arabinose. In vivo, however, the bacterium ceases to express any nucleic acids encoding the AsdA and MurA enzymes, such that synthesis of the peptidoglycan cell wall layer ceases, ultimately resulting in the lysis of the bacterium. This lysis may result in the release of a bolus of antigen specific for an enteric pathogen, thereby serving as a means to enhance induction of immunity against that enteric pathogen while conferring complete biological containment. The waaL gene encodes an enzyme needed to enable attachment of the LPS O-antigen to the LPS core. The regulated loss of this ability specified by the rhaRS $P_{rhaBAD}$ waaL construction in a strain possessing a precise deletion of the native waaL gene confers a means of regulated delayed attenuation that causes *Salmonella* vaccine cells to become sensitive to complement and more readily phagocytized by macrophages. This phenotype also facilitates complete lysis of cells and is another contributing attribute ensuring biological containment.

Vaccine Compositions and Administration

An attenuated microorganism of the invention has been modified to enhance its ability to synthesize and deliver antigens that would induce protective immunity to infections caused by other pathogens, in this case from *Helicobacter*. As such this recombinant attenuated microorganism may be particularly suited for use as a vaccine. Infection of an animal host with a *Salmonella* strain typically leads to colonization of the gut-associated lymphoid tissue (GALT) or Peyer's patches, which leads to the induction of a generalized mucosal immune response to the attenuated microorganism. Further penetration of the bacterium into the mesenteric lymph nodes, liver and spleen augments the induction of systemic and cellular immune responses directed against the bacterium. Thus, the use of recombinant *Salmonella* for oral immunization stimulates all three branches of the immune system, which is particularly important for immunizing against infectious disease agents that colonize on and/or invade through mucosal surfaces.

An attenuated microorganism of the invention may be administered to a host as a vaccine composition. As used herein, a vaccine composition is a composition designed to elicit an immune response to the attenuated microorganism, including any antigens that may be expressed by the bacterium. In an exemplary embodiment, the immune response is protective. As used herein, "protective" means that the immune response contributes to the lessening of any symptoms associated with infection of a host with the pathogen the antigen was derived from or designed to elicit a response against. For example, a protective antigen from a pathogen, such as *Helicobacter* spp, may induce an immune response that helps to ameliorate symptoms associated with *Helicobacter* infection or reduce the morbidity and mortality associated with infection with the pathogen. The use of the term "protective" in this invention does not necessarily require that the host is completely protected from the effects of the pathogen.

Vaccine compositions of the present invention may be administered to any host capable of mounting an immune response. Such hosts may include all vertebrates, for example, human or nonhuman mammals. In a specific embodiment, the mammal is a ruminant such as cow, horse, pig, goat, or sheep. The vaccine can be administered as a prophylactic or for treatment purposes. In an alternative embodiment, the animal host is a bird, such as turkey, geese or chickens.

In exemplary embodiments, the attenuated microorganism is alive when administered to a host in a vaccine composition. Suitable vaccine composition formulations and methods of administration are detailed below.

Vaccine Composition

The *Salmonella* vaccines discussed herein are typically lyophilized after production and may be reconstituted in a pharmaceutically acceptable carrier prior to administration. Such a carrier may be any solvent or solid material for encapsulation that is non-toxic to the inoculated host and compatible with the attenuated microorganism. A carrier may give form or consistency, or act as a diluent. Suitable pharmaceutical carriers may include liquid carriers, such as normal saline and other non-toxic salts at or near physiological concentrations, and solid carriers not used for humans, such as talc or sucrose, or animal feed. Carriers may also include stabilizing agents, wetting and emulsifying agents, salts for varying osmolarity, encapsulating agents, buffers, and skin penetration enhancers. Carriers and excipients as well as formulations for parenteral and nonparenteral drug delivery are set forth in Remington's Pharmaceutical Sciences 19th Ed. Mack Publishing (1995). When used for administering via the respiratory tract, the vaccine is preferably presented in the form of an aerosol.

The dosages of a vaccine or vaccine composition disclosed herein can and will vary depending on the attenuated microorganism, the regulated antigen, and the intended host, as will be appreciated by one of skill in the art. Generally speaking, the dosage need only be sufficient to elicit a protective immune response in a majority of hosts. Routine experimentation may readily establish the required dosage. Typical initial dosages of vaccine for oral administration could be about $1 \times 10^7$ to $1 \times 10^{10}$ CPU depending upon the age of the host to be immunized. Administering multiple dosages may also be used as needed to provide the desired level of protective immunity.

Methods of Administration

In order to stimulate a preferred response of the GALT, NALT or BALT cells, administration of the vaccine composition directly into the gut, nasopharynx, or bronchus is preferred, such as by oral administration, intranasal administration, gastric intubation or in the form of aerosols, although other methods of administering the attenuated microorganism, such as intravenous, intramuscular, subcutaneous injection or intramammary, intrapenile, intrarectal, vaginal administration, or other parenteral routes, are possible.

In some embodiments, these compositions are formulated for administration by injection (e.g., intraperitoneally, intravenously, subcutaneously, intramuscularly, etc.). Accordingly, these compositions are preferably combined with pharmaceutically acceptable vehicles such as saline, Ringer's solution, dextrose solution, and the like.

In an exemplary embodiment, attenuated microorganisms may be administered orally. Oral administration of a composition comprising an attenuated microorganism allows for greater ease in disseminating vaccine compositions for infectious agents to a large number of people in need thereof, for example, in Third World countries or during times of biological warfare. In addition, oral administration allows for attachment of the bacterium to, and invasion of, the gut-associated lymphoid tissues (GALT or Peyer's patches) and/or effective colonization of the mesenteric lymph nodes, liver, and spleen. This route of administration thus enhances the induction of mucosal immune responses as well as systemic and cellular immune responses.

In another embodiment, attenuated microorganisms may be administered by coarse spray. The vaccines are administered by this whole-body spray route in an amount that is effective in eliciting an immune response, i.e. antibody and/or cellular immunity. Whole-body spray administration is surprisingly effective for vaccines comprising a live avirulent derivative of an enteropathogenic bacteria such as attenuated *Salmonella*. The effective doses, which elicit an immune response, are roughly comparable to doses that are effective by the oral route of administration, such as administration in the drinking water.

Kits

The invention also encompasses kits comprising any one of the compositions above in a suitable aliquot for vaccinating a host in need thereof. In one embodiment, the kit further comprises instructions for use. In other embodiments, the composition is lyophilized such that addition of a hydrating agent (e.g., buffered saline) reconstitutes the composition to generate a vaccine composition ready to administer, preferably orally.

Methods of Use

A further aspect of the invention encompasses methods of using an attenuated microorganism of the invention. For instance, in one embodiment the invention provides a method for modulating a host's immune system. The method comprises administering to the host an effective amount of a composition comprising an attenuated microorganism of the invention. One of skill in the art will appreciate that an effective amount of a composition is an amount that will generate the desired immune response (e.g., mucosal, humoral or cellular). Methods of monitoring a host's immune response are well-known to physicians, veterinarians, and other skilled practitioners. For instance, assays such as ELISA, and ELISPOT may be used. Effectiveness may be determined by monitoring the amount of the antigen of interest remaining in the host, or by measuring a decrease in disease incidence caused by a given pathogen in a host. For certain pathogens, cultures or swabs taken as biological samples from a host may be used to monitor the existence or amount of pathogen in the individual.

In another embodiment, the invention provides a method for eliciting an immune response against a *Helicobacter* antigen in a host. The method comprises administrating to the host an effective amount of a composition comprising an attenuated microorganism of the invention.

In still another embodiment, an attenuated microorganism of the invention may be used in a method for eliciting an immune response against *Helicobacter* in a host in need thereof. The method comprises administrating to the host an effective amount of a composition comprising an attenuated microorganism as described herein. In a further embodiment, an attenuated microorganism described herein may be used in a method for ameliorating one or more symptoms of *Helicobacter* infection in a host in need thereof. The method comprises administering an effective amount of a composition comprising an attenuated microorganism as described herein.

The following examples are included to demonstrate preferred embodiments of the invention. It should be appreciated by those of skill in the art that the techniques disclosed in the examples that follow represent techniques discovered by the inventors to function well in the practice of the invention. Those of skill in the art should, however, in light of the present disclosure, appreciate that many changes can be made in the specific embodiments that are disclosed and still obtain a like or similar result without departing from the spirit and scope of the invention, therefore all matter set forth or shown in the accompanying drawings is to be interpreted as illustrative and not in a limiting sense.

EXAMPLES

Example 1

*Salmonella* Strain χ12341

Figure 4:
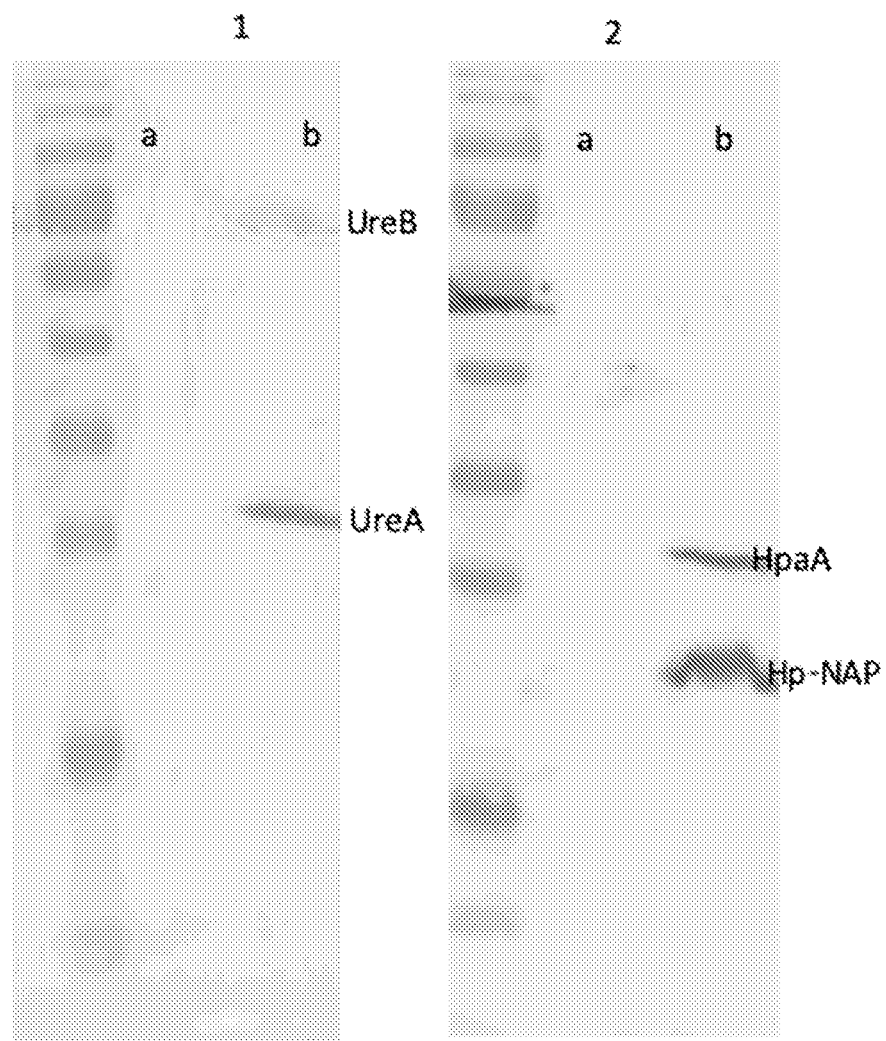
FIG. 4. Successful simultaneous synthesis of four protective *H. pylori* antigens using two different plasmids in *S*. Typhimurium χ12341. (1) UreA and UreB encoded on pG8R230 and (2) Hp-NAP and HpaA encoded on pG8R262. (a) Uninduced with IPTG and (b) 2 h after induction with IPTG compared to molecular mass markers. Anti-6xHis monoclonal antibody was used to detect each recombinant protein in western blotting.

The $\Delta P_{murA}$::TT araC $P_{araBAD}$ murA and $\Delta asdA$::TT araC $P_{araBAD}$ c2 mutations regulate synthesis of diaminopimelic acid acid and muramic acid, two essential constituents of peptidoglycan, which enable PIESV lysis in the absence of DAP and inability to synthesize the MurA enzyme without arabinose in vivo (40). The $\Delta pmi$ $\Delta waaL$ $\Delta pagL$::TT rhaRS $P_{rhaBAD}$ waaL mutations collectively provide regulated delayed attenuation and cause cessation in the synthesis of LPS O-antigen in the absence of the sugars mannose and rhamnose in vivo (41, 61, 62). The deletion Δ(wza-wcaM) enhances complete lysis, blocks the synthesis of cell surface polymers to prevent biofilm formation and enhances induced immunities (63). The ΔrelA::araC $P_{araBAD}$ lacI TT mutation confers the regulated delayed antigen synthesis phenotype that enhances PIESV colonization and induction of immune responses by the arabinose-dependent regulated LacI synthesis so that $P_{trc}$-regulated genes on plasmid vectors are gradually expressed as LacI is diluted at each cell division during in vivo growth (64-66). The ΔrecF mutation decreases inter- and intra-plasmidic recombination to stabilize PIESVs (67). The ΔsifA mutation enables PIESV escape from the *Salmonella*-containing vesicles (SCVs) to cause PIESV cells to lyse in the cytosol (68, 69). This enables delivery of protective antigens to the proteasome for class I presentation to generate CD8−, CD17− and NKT-dependent immunities.

Codon-optimized sequences encoding all nine *H. pylori* antigens were successfully inserted into the plasmid vectors pG8R111 or pG8R114 (FIG. 1) to yield the plasmids listed in Table 1. The expression of each antigen was confirmed by SDS-PAGE and western blot using a monoclonal antibody against the 6His-tag (FIG. 2) to yield the plasmids listed in Table 1. Results of the plasmid stability experiment showed that all recombinant plasmids encoding antigens except HopM were stable in the *Salmonella* vaccine strain. However, only 30% of *Salmonella* cells lost the plasmid specifying HopM synthesis after 50 generations of growth under permissive conditions. Based on results obtained from initial protection experiments as detailed in Table 2, the set of antigens providing considerable protection, were selected to be expressed by pG8R111 and pG8R114, respectively. χ12341 (pG8R230 encoding UreA and UreB) and χ12341 (pG8R262 encoding NapA and HpaA) (see FIG. 3) specified synthesis of the four encoded antigens after IPTG induction (FIG. 4). We also designed and expressed a chimeric antigen including protective parts of four putative antigens (FliD, UreB, VacA and CagA) of *H. pylori* using pG8R111 in PIESV χ12341 as described in the Materials and Methods (see FIG. 5).

Example 2

Immunization of Mice With *Salmonella* Carrying pG8R230 and pG8R262 Induces Significant Protection Against *H. pylori* SS1 Challenge To determine whether immunization with vaccine candidates lowers the bacterial load in the stomachs of infected mice, we ascertained CFUs of *H. pylori* using quantitative bacterial culture procedures. Immunized mice were infected with *H. pylori* SS1 two weeks after the last immunization. Then, four weeks after challenge, the stomachs of euthanized mice were removed, minced, homogenized, serially diluted and then cultured on the selective agar medium. As shown in Table 2 and FIG. 6, higher levels of protection were observed in mice immunized with the *Salmonella* vaccine PIESV-Hp strains carrying pG8R230(UreA+UreB) and pG8R262(NapA+HpaA). Notably, seven out of 10 immunized mice in this group showed sterile protection and the other three mice showed a significant reduction in a load of bacteria compared to mice receiving PBS.

Example 3

Figure 7:
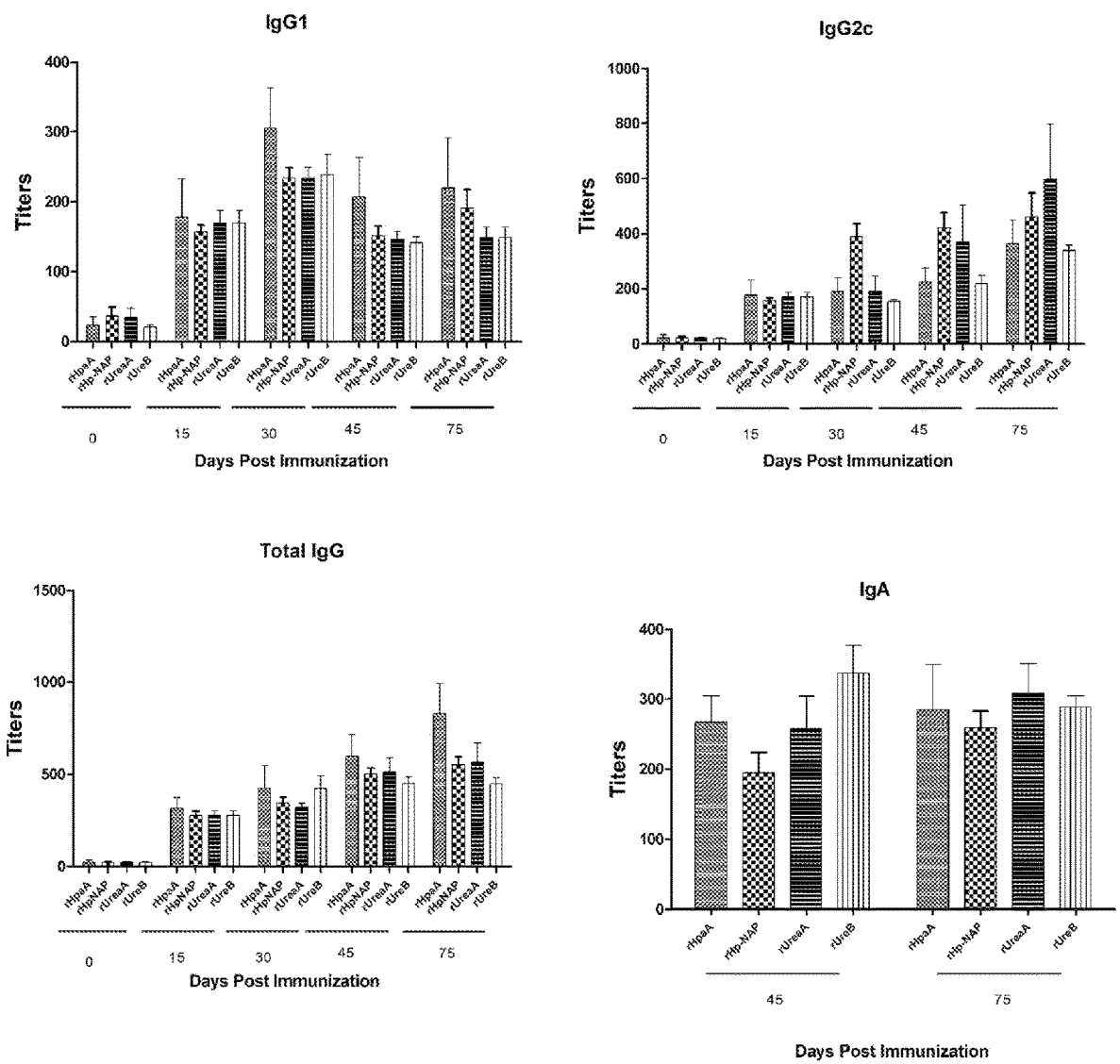
FIG. 7. Analysis of the specific antibody responses in immunized animals. Kinetics of specific antibody responses after oral immunization with a cocktail vaccine of χ12341 (pG8R230) and χ12341 (pG8R262) delivering UreA and UreB and NapA and HpaA, respectively. Mice were bled (submandibular bleeding method) on the indicated days, and specific IgG1 and IgG2c and total IgG antibody titers against recombinant UreA, UreB, NapA and HpaA evaluated by ELISA. Titer values represent the mean±SD of sera from three analyses of five animals each. Stomach suspensions were obtained 45 days post first immunization and specific IgA titers were analyzed by ELISA.

Immunization of Mice With *Salmonella* Carrying pG8R230 and pG8R262 Induces Strong Specific Humoral and Mucosal Immune Responses To study the humoral response against antigens in mice immunized with PIESV vector strains delivering four antigens, sera were obtained at several time points over three months following initial immunization Immunization of mice induced strong and specific immunoglobulin G (IgG) responses against each component of the cocktail vaccine including pG8R230 (UreA+UreB) and pG8R262 (NapA+HpaA), in which IgG2c (Th1-related isotypes) titers were usually slightly above those of the IgG1 subtype (FIG. 7). The total IgG and IgG2c titers against each antigen started to increase during the second week after the first immunization and peaked after 75 days. However, IgG1 titers peaked at 45 days post first immunization and titers fell after 75 days. These results indicated that immunization of mice with *Salmonella* vaccine vectors carrying pG8R230 (UreA+UreB) and pG8R262 (NapA+HpaA) elicit a Th1-biased immune response. To assess whether immunization with PIESV strains delivering these four antigens also induced mucosal immune responses, gastric IgA production was evaluated for each antigen in stomachs of immunized mice. As shown in FIG. 7, the immunized mice with the cocktail of four antigens significantly augmented gastric mucosal IgA titers against each component of the cocktail vaccine. These findings indicate that immunization of mice with a combination of pG8R230 (UreA+UreB) and pG8R262 (NapA+HpaA) synthesized and orally delivered by two PIESV vector strains provokes both specific systemic and mucosal humoral immune responses.

Example 4

Figure 6:
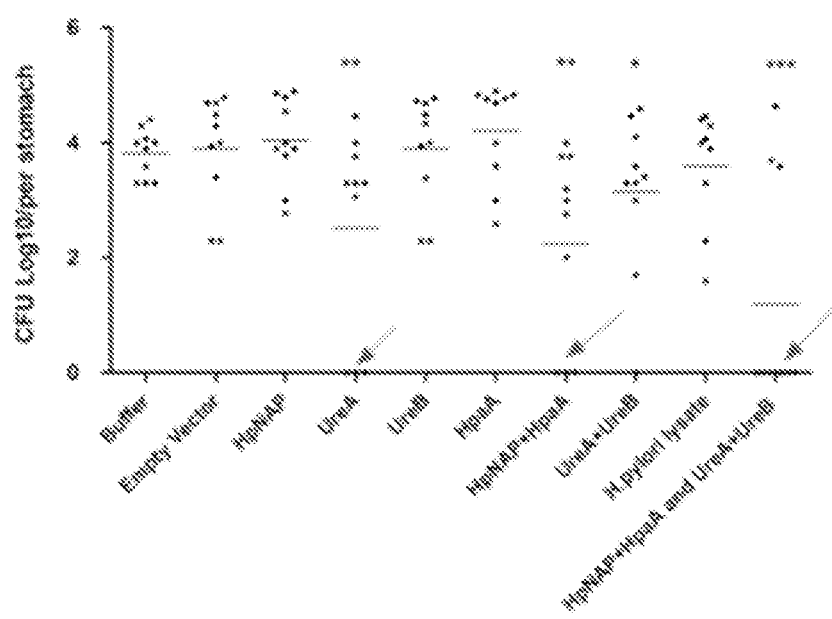
FIG. 6. Protection against *H. pylori* SS1 challenge infection following oral vaccination of mice with individual and combinations of χ12341 strains harboring plasmids listed in Table 1 synthesizing and delivering specified *H. pylori* antigens.
Figure 8:
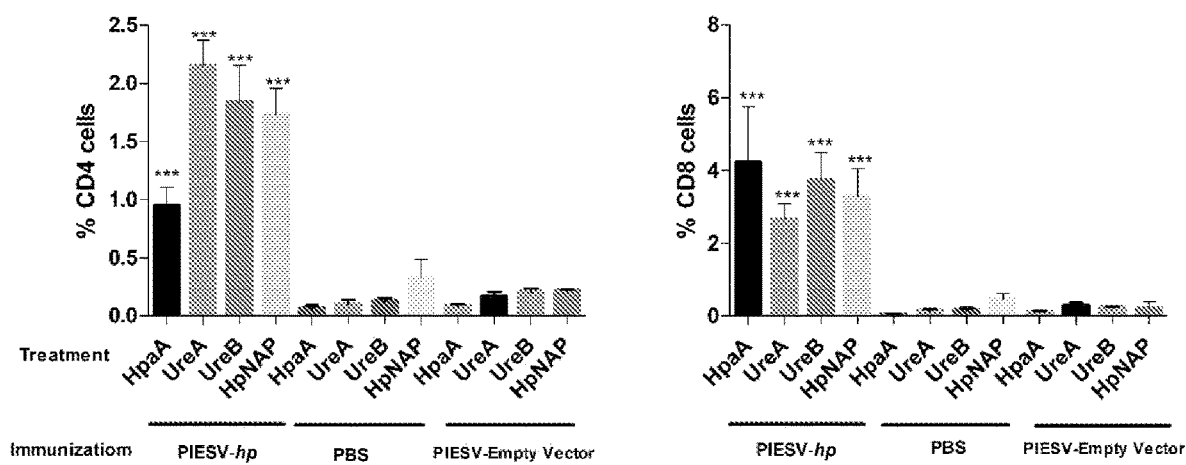
FIG. 8. Proliferative responses of T cells from mice immunized with the χ12341 (pG8R230) and χ12341 (pG8R262) mixture, χ12341 (pG8R111)=PIESV-empty vector) and PBS. T cells from immunized mice were isolated 45 days post first immunization and co-cultured with dendritic cells treated with 20 μg/ml recombinant NapA, HpaA, UreA and UreB and the proliferative responses were subsequently assayed by CellTrace. T cells were also stained with proper antibodies to be analyzed for the proliferation of $CD4^+$ and $CD8^+$ T cells by flow cytometry. * P<0.05;  P<0.01; * P<0.001.

Immunization of Mice With *Salmonella* Carrying pG8R230 and pG8R262 Induces Mixed Th1-, Th2-, and Th17-Type Immune Responses T-Cell Propagation To find out the dominant subset of T cells in the spleens of immunized mice and assess whether such T cells could propagate after re-stimulation with related antigens in vitro, T cells were co-cultured with dendritic cells pulsed with each component of the cocktail vaccine. The percentage of CD4+ and CD8+ cells in the immunized group were significantly increased in comparison to PBS or PIESV-empty vector immunized mice (FIG. 8). Additionally, CD8+ cells propagated more than CD4+ cells showing a dominant cytotoxic response in immunized mice in response to each antigen (FIG. 6).

Cytokine Production

Figure 9:
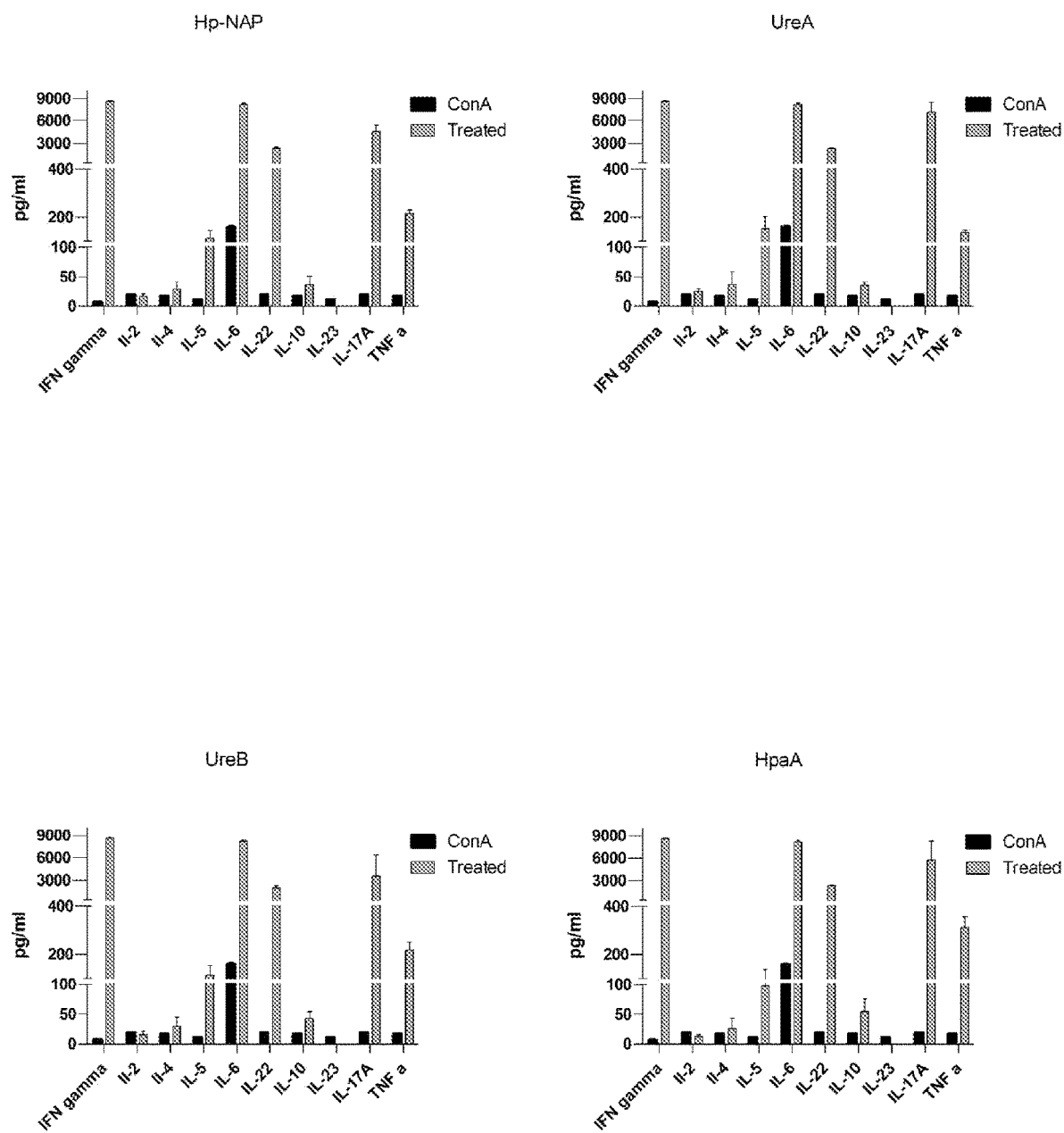
FIG. 9. Cytokine production by T cells from mice immunized with the mixture of χ12341 (pG8R230) and χ12341 (pG8R262). T cells were obtained 45 days post first immunization from immunized mice and co-cultured with dendritic cells already treated with 20 μg/ml recombinant NapA, HpaA, UreA and UreB. Cytokine concentrations in culture supernatants were measured by multiplex ELISA. The data are the mean±SD of five individual mice from each group.
Figure 10:
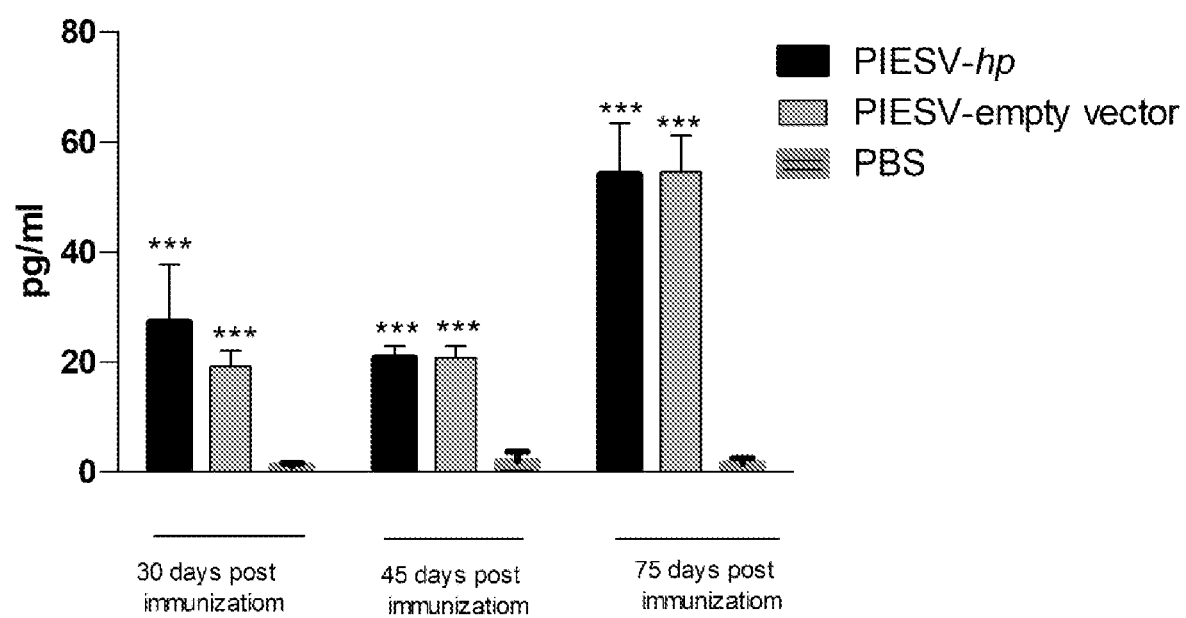
FIG. 10. Level of IL-22 increased in mice immunized with the PIESV-Hp mixture. Sera obtained 30, 45 and 75 days after first immunization of mice with PIESV-Hp, PIESV-empty vectors and PBS were analyzed for the presence of IL-22. *: P<0.05; : P<0.01; *: P<0.001.

Since cytokines produced by activated T cells are indicators of the type of Th responses, we also measured the amounts of ten different cytokines in supernatants obtained in T-cell propagation experiments. Cytokine secretion by the re-stimulated T cells was evaluated by Multiplex ELISA. In comparison to the controls, T cells of mice immunized with the combination of pG8R230 (UreA+UreB) and pG8R262 (NapA+HpaA) synthesized and delivered by two PIESV vector strains secreted significantly higher amounts of IFN-γ, IL-5, IL-6, IL-22, IL-17A and TNF-α in response to each recombinant protein used for immunization (FIG. 9) We could also detect small amounts of IL-2, IL-4 and IL-10 but not IL-23 secreted against each antigen after re-stimulation with related antigens. These results suggest that immunization of mice with a combination of Hp-NAP, UreA, UreB and HpaA synthesized by the PIESV strains induces a mix of Th1, Th2, and Th17 responses. Further study using sera obtained from immunized mice showed that the level of circulating IL-22 cytokine increased following immunization compared to the non-immunized control groups (FIG. 10).

Immunized Mice Increase IFN-γ+ CD4 T and CXCL2 After Infection With *H. pylon* SS1

Figure 11:
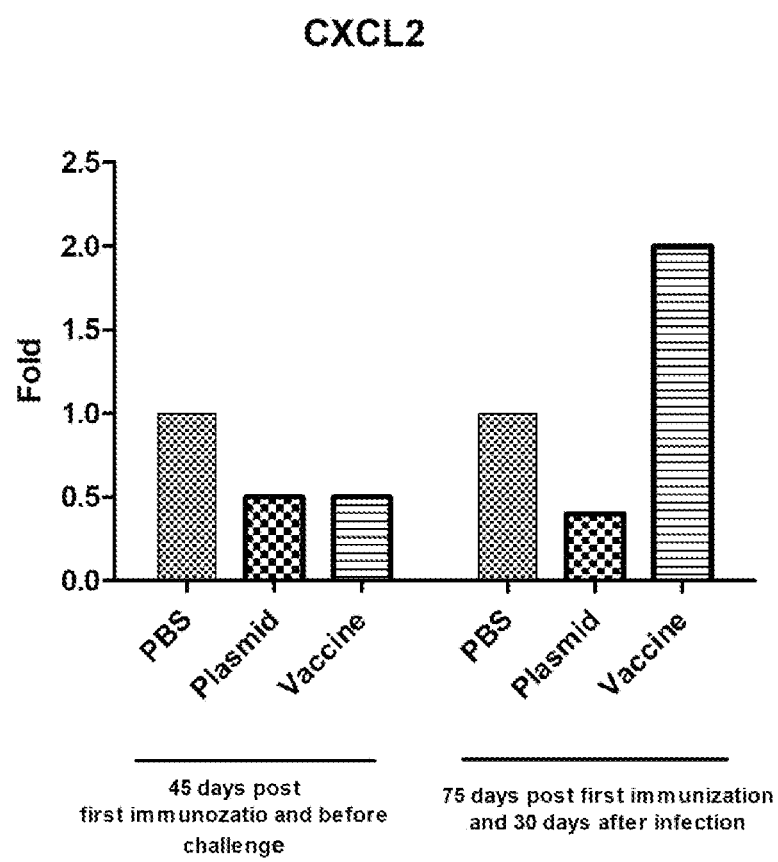
FIG. 11. CXCL2 is increased in stomach of *H. pylori* SS1-infected mice immunized with PIESV-Hp mixture. CXCL2 mRNA synthesis in stomach of *H. pylori* SS1-infected mice immunized with PIESV-Hp, and PIESV (empty vector) and PBS were compared (n=10). *: P<0.05

To obtain a deeper understanding of the roles of antimicrobial peptides and immunological markers in the protection provided in immunized mice, ten days after infecting the tested mice with *H. pylori* SS1, mouse stomachs and spleens were obtained. Reg3a, Reg3b, CXCL1, CXCL2, and CXCL5 in stomach tissues were investigated by qPCR. Spleen samples were further analyzed for T-cell markers and cytokines. In the stomachs of immunized mice after infection with *H. pylori* SS1, the expression of CXCL2 increased two-fold while the expression of the remaining genes did not change (FIG. 11).

Figure 12:
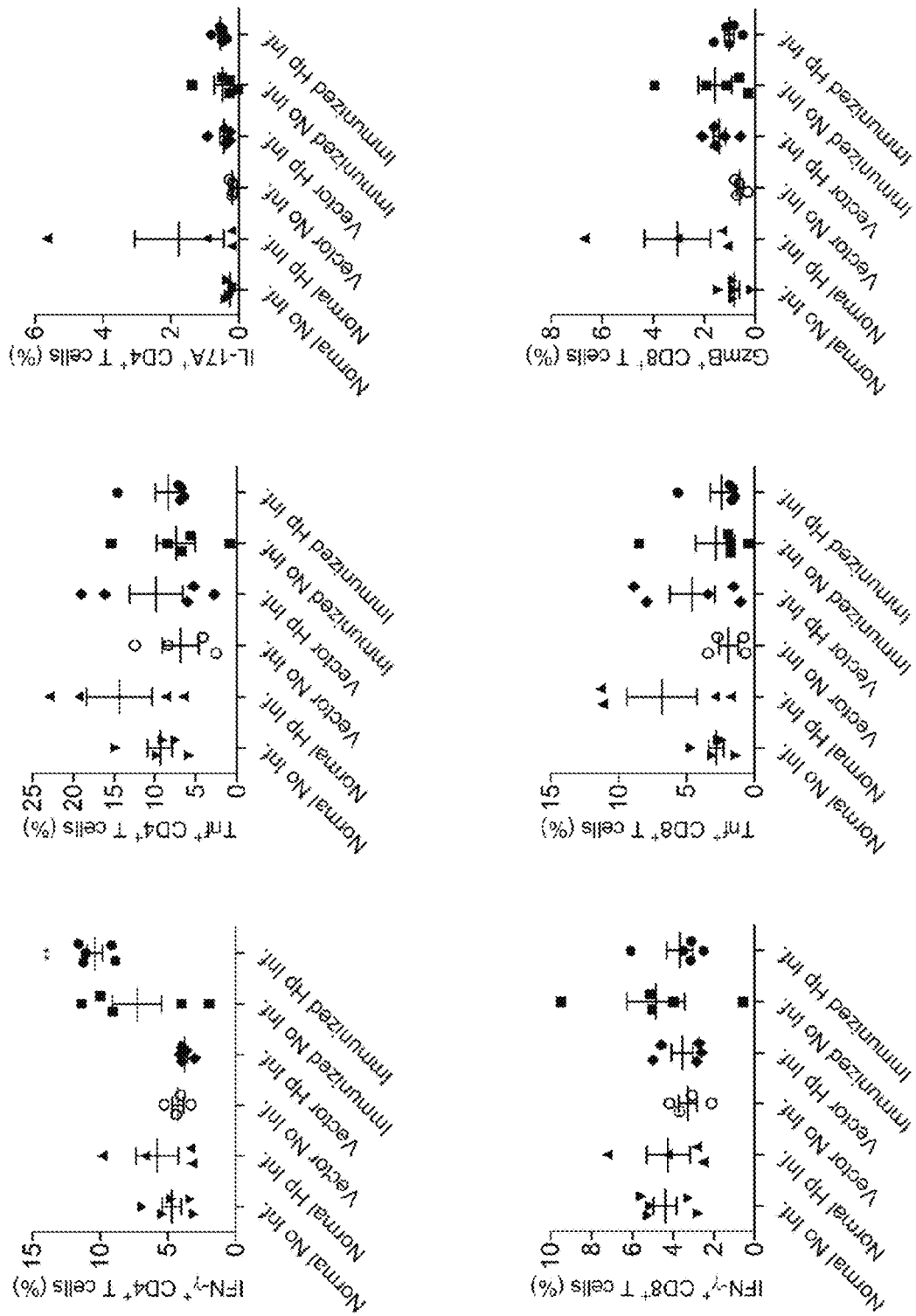
FIG. 12. PIESV-Hp mixture immunized mice showing increases in IFN-γ+ CD4 T and CXCL2 after challenge infection with *H. pylori* SS1. Fifty-five days after the first immunization, mouse spleens were collected. Single-cell suspensions from spleens were isolated and then stained with proper antibodies to be analyzed by flow cytometry. *: P<0.05

In response to *H. pylori* SS1 infection, IFN-γ+ CD4 T cells increased in the spleens of immunized mice compared to the controls. Additionally, no significant changes in TNF+ or IL-17A+ CD4 T cells in the spleen for any test groups were seen. There also were no significant changes in IFN-γ+, TNF+ or GranzymeB+ CD8 T cells in the spleen for any test group (FIG. 12).

Histopathology

The stomach tissues were evaluated and scored based on severity 0 to 3 for criteria including mucosal inflammation and type, submucosal inflammation and type, presence of non-*H. pylori* bacteria, mucosal ulceration, and hyperkeratosis of squamous portions of the stomach. The scale 0-3 refers to 0=normal, 1=mild, 2=moderate, 3=severe. The inflammation ranged from nominal to severe both in the mucosa and submucosa of both the glandular and squamous portions of the stomach and consisted of lymphocytes, plasma cells with or without smaller numbers of neutrophils. Mice in control group had large amounts of hyperkeratosis in the squamous portions of the stomach which are often associated with moderate to large numbers of large, Gram-positive, rod-shaped bacteria on the surface or within the laminated keratin. The hyperkeratosis and associated bacteria are suggestive of hyporexia or anorexia for a relatively prolonged period of at least 2 days. In anorectic rodents, the build-up of excess keratin is presumably caused by reduced mechanical removal by the passage of food (70). The hyperkeratosis was not seen in a single area as suggested at the limiting ridge, but throughout all of the squamous lined areas of the forestomach.

However, significant weight loss was not seen in any group of mice. Overall, the mice receiving the PIESV-empty vector had relatively higher inflammation and numbers of non-*H. pylori* bacteria (gram-positive rod-shaped bacilli) compared to immunized mice. These findings might suggest the role of other gram-positive bacteria as well as *H. pylori* infection in the development of stomach complications. Additionally, these findings demonstrated that the vaccine candidate not only protects against *H. pylori* SS1 but also against other non-*H. pylori* flora, which may have a role in stomach complications (FIG. 13).

Materials and Methods for Examples 1-4

Bacterial Strains and Growth Conditions

Bacterial strains and plasmids used in this study are listed in Table 1. *Escherichia coli* and *S.* Typhimurium UK-1 derivative strains were routinely cultured at 37° C. in LB broth [19] or on LB agar. *S.* Typhimurium UK-1 mutant strains were supplemented with 50 μg/ml of diaminopimelic acid (DAP), 0.05% arabinose, 0.1% mannose and 0.1% rhamnose when necessary for bacterial growth as described in previous work (39-41). For animal experiments, *S.* Typhimurium $\chi$12341 was cultured in LB broth with appropriate supplements. Overnight cultures were diluted 1:100 and grown with aeration (200 rpm) to an optical density at 600 nm of ~0.85. Bacteria were then centrifuged at 5,000×g for 15 min at room temperature and resuspended in buffered saline with 0.01% gelatin (BSG) (42). The *H. pylori* strain SS1 (a kind gift from Prof. James G. Fox, Massachusetts Institute of Technology) was grown on *Brucella* agar supplemented with 5% sheep blood, 25 μg/ml trimethoprim, 3.3 μg/ml polymyxin B, 100 μg/ml vancomycin, 50 μg/ml amphotericin B, 200 μg/ml bacitracinin and 10 μg/ml nalidixic acid in an anaerobic jar with a microaerophilic gas generating kit (BD, USA) for 5 days at 37° C.

Plasmids and Constructs

The regulated lysis vector pG8R111 (FIG. 1A) for synthesis and delivery of antigens has a $P_{trc}$-regulated synthesis of encoded protein antigens for delivery by cell lysis and araC $P_{araBAD}$-regulated murA and asdA genes with GTG start codons to lessen translation efficiency. The pG8R111 has a weaker SD AAGGCAA to further reduce the production of AsdA. The P22 $P_R$ located with opposite orientation to the transcription of the araC $P_{araBAD}$ GTG-murA GTG-asdA genes is repressed by the C2 repressor made during the growth of $\chi$12341 with arabinose. However, C2 concentration decreases due to cell division in vivo to cause $P_R$-directed anti-sense mRNA synthesis to block translation of residual asdA and murA mRNA. Transcription terminators (TT) flank all plasmid domains for controlled lysis, replication, and gene expression so that expression in one domain does not affect activities of another domain. pG8R114 (FIG. 1B) is derived from pG8R111 with a much-improved optimized β-lactmase signal sequence (43), the fusion of molecules to the bla SS in pG8R114 leads to delivery of molecules to the periplasm that results in increased production of outer membrane vesicles (OMVs) and releasing into the supernatant fluid surrounding PIESV cells that enhance induced immune responses (44, 45). We made constructs to synthesize nine putative protective *H. pylori* antigens (1, 46-54) (Table.1). These constructs were evaluated for synthesis and delivery and protective immunity induction in mice. Antigens included VacA, CagA, UreB, UreA, HpaA, BabA, HopM, Hp-NAP and a chimeric antigen. To design the chimeric antigen with the most antigenic fragments of FliD, UreB, VacA and CagA, bioinformatic tools (48) were used to identify T-cell and B-cell epitopes. Sequences encoding FliD (1-600), UreB (327-385), VacA (744-805) and CagA (51-100) polypeptides were accessed from GenBank. To assist epitope exposure, flexible glycine-serine (GS) linkers were included between the gene segments. Sequences were codon-optimized to have a high-level expression in *S.* Typhimurium and GC contents adjusted to be closer to that for *Salmonella*. All gene synthesis was performed by Biomatik (Cambridge, Ontario, Canada). To detect the synthesis of recombinant proteins, a 6 His-tag sequence was added at the 3' end of each gene before the stop codon. Based on the presence or absence of a signal peptide encoded in each antigen gene, antigens were divided into two groups. For those antigens without a signal peptide, the synthesized genes were cloned into pG8R111 whereas for those *H. pylori* antigens with signal sequences, these were removed, and the codon-optimized sequences were inserted into pG8R114 with fusion to the bla SS (Table 1). The sequence encoding the NapA sequence was an exception since it was equally well expressed when inserted into pG8R111 or fused to the bla SS and inserted into pG8R114. Considering the results obtained from the initial protection experiments summarized in Table 2, four antigens were selected for further study. In this regard, the delivery of the UreB, HpaA or NapA (=HP-NAP) antigen alone to vaccinated mice did not result in a significant reduction in the stomach colonization by the *H. pylori* SS1 challenge strain, but when delivered with a second *H. pylori* antigen (and especially UreA), induced significant reduction in *H. pylori* stomach colonization. This synergistic enhancement in induced protective immunity was an unexpected and surprising result. The codon-optimized *H. pylori* ureA, ureB, napA and hpaA genes were fused with $P_{lpp}$ in front of the second gene and then were cloned under control of the $P_{trc}$ promoter of G8R111 or pGR114 (Table 1) (FIG. 1). The resulting plasmids pG8R230 and pG8R262 (FIG.3) carrying these genes were finally electroporated into $\chi$12341. To obtain purified recombinant Hp-NAP (=NapA), UreA, UreB and HpaA, sequences encoding each antigen were cloned into pET28a (+) using NcoI at N-terminal and XbaI at C-terminal sites. pET28 derivatives with inserts were electroporated into *E. coli* BL21(DE3) for synthesis and purification of gene products.

Determination of Plasmid Stability

Measurement of plasmid stability is described previously (42). Briefly, vaccine strains grown overnight (G0) were diluted 1:1000 into pre-warmed fully supplemented LB grown (permissive growth conditions) with aeration for 12 h at 37° C. This process was repeated for approximately 50 generations (the last subculture is called G5) and the proportions of cells holding the Asd$^+$ plasmids were determined for each culture. The percentage of clones holding the plasmids from each culture was determined by counting the colonies grown on LB agar with and without DAP. The continued ability of these clones to synthesize *H. pylori* antigens was also checked after 50 generations using western blotting.

Recombinant Protein Synthesis Evaluated by SDS-PAGE and Western Blot Analyses

*S.* Typhimurium strain χ12341 carrying recombinant plasmids (PIESV-Hp) or empty vectors (PIESV-empty vector) were cultured in LB containing 0.05% arabinose, 0.1% mannose and 0.1% rhamnose at 37° C. LB containing kanamycin 50 µg/ml was used to culture *E. coli* BL21 carrying recombinant plasmids as well. When the bacteria reached an OD600 of 0.6, 1 mM IPTG was added to the cultures to induce heterologous *H. pylori* protein syntheses. Protein samples from bacterial cultures were separated and analyzed by SDS-polyacrylamide gel electrophoresis with transfer to nitrocellulose membranes as previously described (55). Recombinant proteins were detected by anti-6xHis peroxidase (Roche, Basel, Switzerland) (1/40,000) for 2 h. *E. coli* BL21 carrying pG8R289 (ureA-6xHis), pG8R290 (ureB-6xHis), pG8R291 (hpaA-6xHis) or pG8R292 (napA-6xHis) were grown overnight at 37° C. in LB broth supplemented with 50 µg/ml kanamycin. The procedures for protein synthesis and purification have been described in our previous study (4). Prestained Protein Ladder, 10 to 180 kDa (Thermofisher, USA) was used as the protein marker.

Immunization of Mice

All animal experiments were approved by the University of Florida Institutional Animal Care and Use Committee. Six to eight-week-old SPF female C57BL/6 mice (n=10/group), were purchased from Charles River Laboratories (Wilmington, MA). Mice were acclimated for one week after arrival before starting the experiments.

Immunization procedures followed the previous description (4, 55, 56). Briefly, food and water were not given to mice for 6 h prior to the immunization and re-supplied 30 min later. Mice were orally immunized with 20 µl BSG containing $10^9$ CFU of each strain, combination of strains, or with 20 µl BSG alone as the negative control on day 0 and boosted on days 14 and 28. Blood samples were collected individually on days 0, 14, 28, 42 and 72 and serum collected individually after centrifugation for individual analysis of antibody responses. Mice (10 mice) were immunized with $10^9$ CFU of each PIESV synthesizing and delivering different antigens. A mixture of PIESV strains delivering pG8R111 and pG8R114 (PIESV-empty vectors) were used as controls.

Protection Experiment

To assess whether the vaccination of mice with *Salmonella* delivering *H. pylori* antigens was able to reduce bacterial load of *H. pylori* in the stomachs of infected mice, mice were infected with $5 \times 10^8$ *H. pylori* SS1 thrice at one day intervals two weeks after the last immunization. Four weeks post infection, mice were euthanized and their stomachs removed and *H. pylori* CFUs quantified. For this purpose, the quantitative bacterial culture of mouse stomach was used. Briefly, a half section of the stomach from each euthanized mouse was completely homogenized, serially diluted, and then cultured on selective medium as described above.

Evaluation of Serum Antibody Responses by ELISA

To specifically evaluate serum total IgG, IgG1 and IgG2c titers in immunized mice, an enzyme-linked immunosorbent assay (ELISA) was used. 96-well polystyrene plates (Nalge Nunc. Rochester, NY, USA) were coated with purified recombinant HpaA, UreA, UreB and Hp-NAP (5 mg/ml). Upon over-night incubation, the plates were washed three times with TBST buffer (Tris-buffered saline, pH 7.4, containing 0.05% Tween 20) followed by blocking with 300 µl PBS containing 10% FBS for 2 h at 37° C. After adding serial dilutions of mouse sera to the plates, they were incubated for 2 h at room temperature and then washed. HRP-conjugated goat-anti-mouse IgG1, IgG2c or total IgG (Southernbiotech, Birmingham, AL, USA) were added to the wells and incubated for another 90 min at 37° C. After the last washing step, specific reactivity was calculated by the addition of 50 µl/well of the enzyme-substrate TMB (Thermofisher, USA). The reaction was stopped by adding 15 µl of 2 M $H_2SO_4$. Next, the absorbance at 450 nm was measured. To define a cut-off value for the test, the mean specific OD plus three-fold SD of sera from mice immunized with BSG was calculated at a 1:100 dilution. Serum titers were calculated as the reciprocal of the last serum dilution providing an OD higher than the cut-off (57). To assess stomach mucosal IgA production, the secretory IgA was extracted by incubation of mouse stomachs in PBS containing 5% non-fat dry milk, 4-(2-aminoethyl)-benzenesulphonyl fluorid (Calbiochem), 1 mg/ml 3.25 mM aprotinin, 10 mM leupeptin (Sigma), and bestatin (Boehringer-Mannheim Biochemicals). After extensive vortexing and centrifugation (16,000 g for 10 min), the supernatants were used for the determination of antibody titers. An ELISA was used as described above.

T-Cell Activation Cell and Cytokine Profiling

A. Isolation of DCs From Mouse Bone Marrow:

C57BL/6 mice were euthanized, femurs were removed under sterile conditions, and then soaked in 70% alcohol for a minute. Both ends of the bone were cut off with scissors, and the needle of a 1-mL syringe was inserted into the bone cavity to rinse the BM out of the cavity into a sterile culture dish with RPMI 1640 supplemented with 2 mM L-glutamine, 100 U/ml penicillin, 100 µg/ml streptomycin and 10% heat-inactivated fetal bovine serum. The cell suspension in the dish was collected and counted. The cells suspended were distributed in plates at a density of $2 \times 10^6$ cells/per plate. Subsequently, GM-CSF was added into the medium to a final concentration of 20 ng/mL. The cells were cultured at 37° C. in an incubator containing 5% $CO_2$. The culture medium was replaced 72 h later to remove the unattached cells and cell debris, then the fresh medium was supplemented with GM-CSF. On day 10, the semi-suspended cells and loosely attached cells were collected by gently pipetting the medium against the plate. The cells were pulsed with recombinant proteins (HpaA, Hp-NAP, UreA and UreB) and incubated in complete medium overnight before co-culturing with T cells.

B. Antigen-Specific T-Cell Assay:

Mouse spleens were obtained from mice immunized with PIESV-Hp (hpaA, napA, ureA, ureB), PIESV-empty vector or PBS, at 45 days post the first immunization. T cells were isolated and counted using EasySep™ Mouse T Cell Isolation Kit (STEMCELL, Cambridge, MA USA). T cells were then stained with CellTrace (Thermofisher, USA) to trace the propagation of T cells after re-stimulation by flow cytometry. After that, T cells and DCs already pulsed with recombinant proteins (HpaA, UreA, UreB and Hp-NAP) were co-cultured 10 to 1, (T cells to DCs, respectively) and incubated for 7 days. Supernatants were collected and cells were stained by antibodies against CD3, CD4, and CD8. Using Flow cytometer, T-cell propagation against each antigen in addition to different types of T cells were investigated.

C. Cytokine Assay:

The concentration of ten different cytokines including IFN-γ, TNF-alpha, IL-2, IL-4, IL-5, IL-6, IL-10, IL-17A, IL-22, and IL-23 were measured in both sera and supernatants described in the previous section. We used Multiplex Assays Using Luminex (Millipore-Sigma, USA) to evaluate the concentration of cytokines in the samples. In this method, the sample is added to a mixture of color-coded beads, pre-coated with different cytokine-specific capture antibodies. The antibodies finally bind to the interested cytokines. Specific detection antibodies of cytokines of interest conjugated with biotin are added and form an antibody-antigen sandwich. PE-conjugated streptavidin is then added. It attaches to the biotinylated detection antibodies. Polystyrene beads are read on a dual-laser flow-based detection set, using Luminex 200™. One laser categorizes the bead and defines the cytokine that is being detected. The second laser defines the greatness of the PE-derived signal, which is in direct quantity to the amount of cytokine bound.

Immunological Responses in Stomach of Immunized Mice After Infection With *H. pylori*

A. Spleen Single-Cell Suspension Preparation and Flow Cytometry:

To obtain further information about how the immune system responded in the immunized mice after infection with *H. pylori*, ten days after the challenge (day 55) mouse spleens were collected. Single-cell suspensions from spleens were prepared by pressing spleens through 100 μm cell strainers. Cell suspensions were washed in PBS and resuspended in red blood cell lysis buffer [155 mM $NH_4Cl$; 10 mM $KHCO_3$; 0.1 mM EDTA] for 8 min on ice. Cell suspensions were washed again with PBS before staining. Antibodies were purchased from eBioscience (CD8a, IFNγ, IL-17A, CD16/32, and TNFα), BioLegend (GranzymeB, Aqua Live/Dead), or TONBO (CD3 and CD4). CD16/32 antibody was used to block nonspecific binding to Fc receptors before all surface staining. For cytokine staining, cells were stimulated with 50 ng/mL phorbol-12-myristate-13-acetate (PMA) and 500 ng/mL ionomycin for 4 h, and Brefeldin A (2 mg/mL) was added 2 h before cell harvest. Dead cells were discriminated by LIVE/DEAD Fixable Violet Dead Cell Stain Kit (Invitrogen). Sample acquisition was performed on FACSCantoII and analyzed with FlowJo (version 10.2, Tree Star).

B. Quantitative Real-Time PCR Analysis:

The expression of CXCL1, CXCL2, CXCL5, Reg3a, Reg3b, Reg3d and Reg3g were investigated using qPCR (58, 59). Briefly, extracted RNA from mouse stomach biopsy specimens obtained ten days after infection were reverse-transcribed to cDNA by PrimeScript™ RT reagent Kit (ThermoFisher). Real-time PCR was performed on the IQ5 (Bio-Rad) with PowerUp™ SYBER™ Green Master Mix (appliedbiosystems, USA) according to the manufacturer's specifications. β-actin was used for normalizing the expression. The relative gene expression was expressed as fold change calculated by the ΔΔCt method (60).

Histology

Mouse stomachs were obtained 75 days post the first immunization. Stomach tissues were fixed in 10% neutral buffered formalin for at least 24 h. The trimmed tissues were routinely processed, paraffin-embedded, sectioned at 5 μm, and stained with hematoxylin and eosin. Selected sections of stomach tissues were also evaluated with Warthin-Starry and Gram stains to identify bacteria. The pathologist was blinded as to the experimental groups and treatments of the study. Histologic samples of both glandular and squamous portions of the stomach were examined and evaluated and scored based on intensity 0 to 3 for criteria including mucosal inflammation and type, submucosal inflammation and type, non-*H. pylori* bacteria, mucosal ulceration, and hyperkeratosis of squamous stomach.

Statistical Analysis

Statistical analysis was done using SPSS computer software, version 17.0. The statistical differences between two groups were studied by t-test and results among several groups were obtained by one factor analysis of variance (ANOVA) and Tukey's post hoc test. The statistical border for accepting significance was p<0.05. Data were envisaged using the GraphPad Prism 7 program.

TABLE 1

Plasmids and strains used in this study

| Strain or Plasmid | Genotype or relevant characteristics | Derivation or source |
|---|---|---|
| *E. coli* | | |
| BL21(DE3) | F⁻ ompT $hsdS_B$ ($r_B^- m_B^-$) gal dcm (DE3) | Novagen |
| χ6212 | F⁻ λ⁻ φ80 Δ(lacZYA-argF) endA1 recA1 hsdR17 deoR thi-1 glnV44 gyrA96 relA1 ΔasdA4 | [81] |
| *Salmonella* Typhimurium χ12341 | $\Delta P_{murA25}$::TT araC $P_{araBAD}$ murA ΔasdA27::TT araC $P_{araBAD}$ c2 Δ(wza-wcaM)-8 Δ Δpmi · ΔrelA197::araC $P_{araBAD}$ lacI TT ΔrecF126 ΔsifA26 ΔwaaL46 ΔpagL64::TT rhaRS $P_{rhaBAI}$ | (Wang, Unpublished data) |
| Plasmid | | |
| pET28a+ | Expressing vector, Kan+, pBR ori, T7 promoter | Novagen |
| pG8R111 | Lysis vector, pBR ori, $P_{trc}$, araC $P_{araBAD}$ SD-GTG murA, weak SD-GTG asdA | (Wang, unpublished) |
| pG8R114 | Lysis vector with optimized bla SS, pBR ori, $P_{trc}$ araC $P_{araBAD}$ SD-GTG murA, weak SD-GTG asdA | (Wang, unpublished) |
| pG8R60 | The optimized hpaA gene of *H. pylori* fused with a C-terminal 6xHis was cloned under control of the $P_{trc}$ promoter of pG8R114. | This study |
| pG8R61 | The optimized ureA gene of *H. pylori* fused with a C-terminal 6xHis was cloned under control of the $P_{trc}$ promoter of pG8R111. | This study |

TABLE 1-continued

Plasmids and strains used in this study

| Strain or Plasmid | Genotype or relevant characteristics | Derivation or source |
| --- | --- | --- |
| pG8R62 | The optimized cagA gene of *H. pylori* fused with a C-terminal 6xHis was cloned under control of the $P_{trc}$ promoter of pG8R111. | This study |
| pG8R63 | The optimized babA gene of *H. pylori* fused with a C-terminal 6xHis was cloned under control of the $P_{trc}$ promoter of pG8R114. | This study |
| pG8R64 | The optimized napA gene of *H. pylori* fused with a C-terminal 6xHis was cloned under control of the $P_{trc}$ promoter of pG8R111. | This study |
| pG8R65 | The optimized chimeric gene (fliD, ureB, vacA, cagA) gene of *H. pylori* fused with a C-terminal 6xHis was cloned under control of the $P_{trc}$ promoter of pG8R111. | This study |
| pG8R66 | The optimized ureB gene of *H. pylori* fused with a C-terminal 6xHis was cloned under control of the $P_{trc}$ promoter of pG8R111. | This study |
| pG8R165 | The optimized hopM gene of *H. pylori* fused with a C-terminal 6xHis was cloned under control of the $P_{trc}$ promoter of pG8R114. | This study |
| pG8R166 | The optimized vacA gene of *H. pylori* fused with C-terminal 6xHis was cloned under control of the $P_{trc}$ promoter in pG8R111. | This study |
| pG8R230 | The optimized ureA and $P_{lpp}$ ureB genes of *H. pylori* were fused together with a C-terminal 6xHis and was cloned under control of the $P_{trc}$ promoter of pG8R111. | This study |
| pG8R232 | The optimized napA and $P_{lpp}$ ureA genes of *H. pylori* were fused together with a C-terminal 6xHis and was cloned under control of the $P_{trc}$ promoter of pG8R114. | This study |
| pG8R233 | The optimized napA and $P_{lpp}$ ureB genes of *H. pylori* were fused together with a C-terminal 6xHis and was cloned under control of the $P_{trc}$ promoter of pG8R111. | This study |
| pG8R234 | The optimized napA and $P_{lpp}$ ureA genes of *H. pylori* were fused together with a C-terminal 6xHis and was cloned under control of the $P_{trc}$ promoter of pG8R114. | This study |
| pG8R235 | The optimized hpaA and $P_{lpp}$ ureB genes of *H. pylori* were fused together with a C-terminal 6xHis and was cloned under control of the $P_{trc}$ promoter of pG8R114. | This study |
| pG8R262 | The optimized napA and $P_{lpp}$ hpaA genes of *H. pylori* were fused together with a C-terminal 6xHis and was cloned under control of the $P_{trc}$ promoter of pG8R114. | This study |
| pG8R289 | The ureA gene of *H. pylori* fused with a C-terminal 6xHis cloned into the NcoI and XbaI sites in pET28a | This study |
| pG8R290 | The ureB gene of *H. pylori* fused with a C-terminal 6xHis cloned into the NcoI and XbaI sites in pET28a | This study |
| pG8R291 | The hpaA gene of *H. pylori* fused with a C-terminal 6xHis cloned into the NcoI and XbaI sites in pET28a | This study |
| pG8R292 | The napA gene of *H. pylori* fused with a C-terminal 6xHis cloned into the NcoI and XbaI sites in pET28a | This study |

TABLE 2

Colonization of stomach by *H. pylori* in immunized mice.

| Group | Antigens | Log10 CFU of *H. pylori* |
| --- | --- | --- |
| 1 | HpaA | 4.2 |
| 2 | Hp-NAP | 4 |
| 3 | UreA | 2.52* |
| 4 | UreB | 3.9 |
| 5 | UreB + UreA | 1.8** |
| 6 | VacA, +Hp-NAP | 1.9** |
| 7 | UreA + HpaA | 1.4*** |
| 8 | HpaA + BabA | 3.34 |
| 9 | CagA + VacA | 2.31* |
| 10 | Chimeric (FliD, UreB, VacA, CagA) | 2.3* |
| 11 | BabA + HopM | 3.8 |
| 12 | HopM + CagA | 2.45 |
| 13 | Hp-NAP + HpaA | 1.9** |
| 14 | HpaA + UreB | 1.8** |
| 15 | UreB + VacA | 4 |
| 16 | VacA + UreA | 1.9** |
| 17 | Hp-NAP + UreB | 1.63** |
| 18 | UreA + HopM | 3.3 |
| 19 | HopM + Hp-NAP | 4.3 |
| 20 | *H. pylori* lysate | 2.8* |
| 21 | BSG | 3.6 |
| 22 | Empty vector | 3.7 |
| 23 | *UreA + UreB HpaA + Hp-NAP | 1.19*** |

*P < 0.05;
**P < 0.01;
***P < 0.001 compared with PBS and Empty vector

Groups refer to immunization of groups of ten mice with χ12341 containing the plasmids listed in Table 1 encoding the *H. pylori* antigens specified.

Example 5

Figure 5:
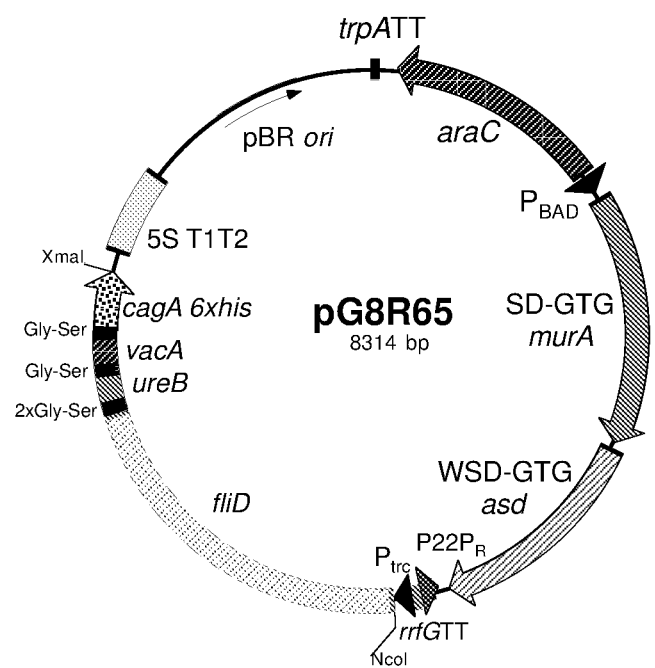
FIG. 5. Regulated delayed lysis plasmid vector pG8R65 encoding the fliD-ureB-vacA-cagA fusion derived from pG8R111.

Presentation of Protective *H. pylori* Antigens Encoded on Regulated Delayed Lysis Plasmid Vectors in Improved PIESV Vector Strains As described in Example 1, the *S.* Typhimurium PIESV vector strain χ12341was used to synthesize and deliver the *H. pylori* protein antigens to vaccinated mice to generate the results described in Examples 2, 3 and 4. As described in the Materials and Methods for Examples 1-4, in the section on Immunization of mice, the mice were immunized on day 0 and boosted with the same dose of vaccine on days 14 and 28. This vaccination regimen was determined to be optimal to achieve the levels of protection observed. However, it would be preferable to enable induction or protective immunity after a single vaccination. This would reduce the expense associated with having to give multiple vaccinations and the problems in ensuring that vaccinated individuals return for their second and third vaccine doses. In other studies, it has been determined that χ12341, although excellent for delivering antigens to induce protective immunity to broiler chickens against bacterial pathogens, does not persist long enough in mice after a single vaccination to induce a high level of protective immunity.

χ12341 with the plasmid vectors pG8R111 and pG8R114 (FIG. 1) displays the regulated delayed lysis in vivo phenotype due to the absence of arabinose needed for synthesis of aspartate semialdehyde dehydrogenase encoded by the asdA gene and UDP-N-acetylglucosamine enolpyruvyl transferase encoded by the murA gene necessary for the synthesis of diaminopimelic acid (DAP) and muramic acid, respectively, two unique essential components of the peptidoglycan rigid layer of the bacterial cell wall. In the absence of arabinose, these strains ultimately undergo lysis as the asdA- and murA-encoded enzymes are diluted as a consequence of PIESV cell division in vivo. Although *Salmonella* has a generation time of some 40 to 50 min when growing in the lab in LB broth, cell division in vivo takes much longer varying from 10 to 20 h depending on the specific in vivo intra or extracellular habitat. We have investigated many means to modulate alterations in the rate of in vivo cell division of *Salmonella* vaccine vector strains with the discovery of genotypes to enable sufficiently prolonged persistence with protective antigen synthesis and delivery to maximize induction of mucosal, systemic and cellular protective immune responses but at the same time to ensure expression of biological containment with no long-term persistence of viable PIESV cells in vivo and no survival if shed into the environment. These collective attributes are unique and important, since persistence of viable *Salmonella* vaccine cells for two to three weeks in vivo is critical for the induction of cellular immune responses of long duration due to induction of immune memory responses (1).

Based on these discoveries described in co-pending U.S. Provisional Application No. 63/120,940 filed Dec. 3, 2020, we described the construction of *S.* Typhimurium χ12615 with the genotype $\Delta P_{murA25}$::TT araC $P_{araBAD}$ murA ΔasdA27::TT araC $P_{araBAD}$ c2 ΔwaaL46 ΔpagL38::TT rhaRS $P_{rhaBAD2}$ waaL2 Δ(wza-wcaM)-8 ΔrelA1123 ΔrecF126 ΔsifA26 ΔaraBAD65::TT ΔrhaBADSR515 ΔpagP8 ΔlpxR9 (pSTUK201 Δ(traM-traX)-36::araC $P_{araBAD}$ lacI TT. Many of the mutations in χ12615 are also present in χ12341 from which χ12615 was derived. These beneficial mutations present in χ12341 have thus been retained. These include Δ(wza-wcaM)-8 that eliminates some 20 genes that encode enzymes that *Salmonella* can use to synthesize extracellular polysaccharides such as colanic acid (2) that is made under stress and reduces completeness of regulated cell lysis (3-7) and LPS O-antigen capsule (8-10) that both act to suppress induction of immune responses. In addition, the Δ(wza-wcaM)-8 mutation enhances early onset induced antibody responses (2). The ΔrecF126 mutation reduces inter- and intra-plasmidic recombination and thus stabilizes maintenance of the genetic integrity of regulated lysis plasmid vectors (11). The ΔsifA26 mutation enables PIESV constructs to escape from the *Salmonella* Containing Vacuole (SCV, an endosome compartment) so that lysis of some vaccine cells occurs in the cytosol so that protective antigens released during lysis can be presented to the proteasome for Class I presentation to facilitate induction of CD8, CD17 and NKT cellular immune responses (12-15).

It is well recognized that animal sensitivity to the endotoxin of gram-negative bacteria composed of the LPS lipid A moiety varies over a 1000-fold range with birds such as chickens being very tolerant/resistant while humans and especially horses are extremely sensitive (16-21). Since deletion of genes for synthesis of lipid A is lethal due to the importance of lipid A in constituting the lipid in the outer layer of the outer membrane in gram negative bacteria, it is critical to determine the components of lipid A leading to toxicity to determine how they might be modified or eliminated to reduce toxicity. However, lipid A constitutes a Pathogen-Associated Molecular Pattern (PAMP) now generally referred to as a Microbe-Associated Molecular Pattern (MAMP) since they are present on all gram-negative bacteria) that interacts with TLR4 to recruit innate immunity. This interaction is therefore of critical importance in enhancing the immunogenicity of bacterial vectored vaccines. We have therefore included the ΔpagP8 and ΔlpxR9 mutations in χ12615 to lessen lipid A toxicity and can then easily replace the ΔpagP8 mutation with the ΔpagP81::$P_{lpp}$ lpxE deletion-insertion mutation that synthesizes the *Francisella tularensis* LpxE enzyme that eliminates the 1' phosphate from lipid A to render lipid A totally nontoxic while retaining ability to bind to TLR4 (22).

The inclusion of the ΔaraBAD65::TT and ΔrhaBADSR515 mutations to block catabolism of arabinose or rhamnose present in vaccine cells at the time of harvesting from the fermenter delays by one to three in vivo cell divisions the cessation in synthesis of arabinose and rhamnose regulated genes. This then delays the time in which vaccine cells commence to synthesize protective antigens expressed under the control of the LacI repressible $P_{trc}$ promoter, the time for cessation of LPS O-antigen and the time for commencement of cell lysis.

Since the Δpmi-2426 mutation in χ12341 leaves two sugars still attached to the LPS core, it was removed in the construction of χ12615. Since the elimination of the WaaL enzyme which is the ligase that attaches LPS O-antigen units to the LPS core, the elimination of the Δpmi-2426 mutation increases the sensitivity of vaccine cells to C'-mediated cytotoxicity. While this is an added safety benefit, dead cells cannot synthesize protective antigens or undergo programmed continued cell lysis. We thus replaced the ΔpagL64::TT rhaRS $P_{rhaBAD1}$ waaL1 mutation in χ12341 with the ΔpagL38::TT rhaRS $P_{rhaBAD1}$ waaL2 sequence in χ12615 to cause a higher level of WaaL synthesis that would require more in vivo cell divisions for the amount of WaaL to be diluted out. This in turn increases the number of in vivo cell divisions for complete loss of LPS O-antigen and display of complete sensitivity to C'-mediated cytotoxicity. To achieve this the $P_{rhaBAD}$-10 sequence in the ΔpagL64::TT rhaRS $P_{rhaBAD1}$ waaL1 deletion-insertion mutation was changed from TAGACT to TATAAT, the SD sequence changed from AAGG to AGGA and two Lys AAA codons inserted after the ATG start codon in the ΔpagL38::TT rhaRS waaL2. These three changes increased RNA polymerase binding to the promoter, ribosome loading at the ribosome-binding site and efficiency of translation initiation.

The last significant improvement in χ12615 was to replace the chromosomal ΔrelA::araC $P_{araBAD}$ lacI TT mutation with the Δ(traM-traX)-36::araC $P_{araBAD}$ lacI TT) mutation that is present in the *S.* Typhimurium virulence plasmid now designated pSTUK201. This mutation deletes a large segment of the virulence plasmid sequence encoding genes that permitted the virulence plasmid to be conjugationally transferred to other bacterial cells. Thus, this substitution enhances the safety of the vaccine vector while retaining the regulated delayed antigen synthesis attribute. χ12615 also has the chromosomal ΔrelA1123 mutation which uncouples a dependance on protein synthesis for continued cell growth that is required to achieve complete lysis of the vaccine construct in vivo to release a bolus of protective antigens.

The detailed methods with description of suicide vectors used in strain modification to construct χ12615 and the nucleotide sequences of the genetic modifications are provided in co-pending U.S. Provisional Application No. 63/120,940 filed Dec. 3, 2020.

We have therefore constructed derivatives of χ12615 with the regulated delayed lysis plasmids pG8R111 and pG8R114 (Table 1) to serve as empty-vector control constructs and the plasmid derivatives encoding *H. pylori* protective antigens pG8R230 and pG8R262 (FIG. 3) and the *H. pylori* gene fusion construct pG8R65 (FIG. 5). These constructs have been tested for genetic correctness and stability and for ability to synthesize the *H. pylori* antigens in a regulated manner.

In ongoing studies as disclosed in co-pending U.S. Provisional Application No. 63/120,940 filed Dec. 3, 2020, we are investigating other improvements to further enhance the safety and immunogenicity of χ12615.

*S.* Typhimurium has some 12 operons encoding fimbrial appendages. Some of these fimbriae contribute to intestinal colonization because of adherent components on the fimbriae. However, some of these fimbriae fail to be synthesized under any in vitro condition and are not synthesized in the GI tract either. However, the Sta and Saf fimbriae that are not synthesized under any laboratory experimental condition are synthesized and assembled in vivo in spleens (23). This in vivo up-regulation in synthesis and assembly was an important observation since the spleen is possibly the most important internal effector lymphoid tissue and is responsible for generating long-lasting protective immunity. Constitutive in vivo synthesis of either the Saf fimbriae or the Stc fimbriae in PIESV strains can be achieved by the addition of either the $\Delta P_{safS}::P_{murA}$ safA or $\Delta P_{stc}::P_{murA}$ stcA deletion-insertion mutation, in which synthesis and assembly is specified by the constitutive promoter of the mur operon, essential for synthesis of the rigid peptidoglycan layer of the cell wall. Such PIESV vaccine vector strains delivering the protective *Streptococcus pneumoniae* PspA protective antigen enhanced both the anti-PspA antibody responses and increased the levels of protective immunity to challenge of vaccinated animals with a wild-type virulent *S. pneumoniae* strain (23). Representative results demonstrating that constitutive expression of the operons encoding the Saf and Stc fimbriae in antigen delivery vaccine vector strains are better at conferring protective immunity to pathogen challenge are presented in Table 3.

TABLE 3

Protective efficacy of PIESV strains expressing Saf or Stc fimbriae in a constitutive manner and delivering the *S. pneumoniae* PspA antigen to orally vaccinated BALB/c mice

| Strain | Constitutively expressed fimbrial genes | No. of mice alive/ total no. | % survival |
|---|---|---|---|
| χ11850(pYA4088) | saf | 10/19 | 52.6 |
| χ11851(pYA4088) | stc | 10/19 | 52.6 |
| χ9088(pYA4088) | none | 3/11 | 27.3 |
| None (PBS) (control) | — | 0/18 | 0.0 |

Seven-week-old BALB/c mice were immunized orally with ~1×10$^8$ CFU of the indicated *S.* Typhimurium vaccine strains and boosted with the same dose 6 weeks later. All mice were challenged by intraperitoneal inoculation 4 weeks after the booster dose with ~1×10$^4$ CFU of virulent *S. pneumoniae* strain WU2. Deaths were recorded until 3 weeks post-infection.

It is also likely that the Saf and Stc fimbriae that represent MAMPs recruit innate immunity by interaction with some TLR, which has yet to be identified. Based on these observations, the addition of either or both the $\Delta P_{safS}::P_{murA}$ safA and $\Delta Pstc::P_{murA}$ stcA deletion-insertion mutation to the PIESV vector strain χ12615 should enhance colonization of the spleen to enhance the level of induced protective immunity of delivered *H. pylori* protective antigens.

Example 6

Enhancement of Levels of Protective Immunity Against *H. pylori* by Delivery of Protective Antigens by Improved PIESV Vector Strains With Co-Administration of a Self-Destructing Attenuated Adjuvant *Salmonella* (SDAAS) Strain In previous work we have modified *Salmonella* strains to undergo rapid in vivo lysis to recruit rapid induction of innate immune responses to enhance induction of protective immunity by co-administered subunit, live attenuated and live vectored vaccines. The construction and properties of these SDAAS strains are described in U.S. Ser. No. 63/017,866 (Live self-destructing bacterial adjuvants to enhance induction of immunity). Enhancement in the levels of protective immunity induced by the PIESV constructs synthesizing and delivering *H. pylori* protective antigens can thus be achieved by co-administration of SDAAS strains in either the Family A or Family B lineages (that differ in their rates of lysis in vivo).

Thus, the Family A SDAAS strain χ12661 (Δalr-3 ΔdadB4 ΔasdA33 ΔfliC180 Δ(hin-fljBA)-219 ΔpagP8 ΔlpxR9 ΔpagL7 ΔeptA4 ΔarnT6 ΔsifA26 ΔrecA62) can be administered either mucosally (intranasal) or parenterally (subcutaneous, intramuscular, intravenous) at the same time as the PIESV strains delivering *H. pylori* antigens are orally administered. In this case, χ12615 (pG8R230) plus χ12615 (pG8R262) or improved derivatives would be used to maximize the induction of protective immunity against the consequences of *H. pylori* infections. χ12661 will efficiently recruit innate immunity via interaction with TLR4 (due to the ΔpagP8 ΔlpxR9 ΔpagL7 ΔeptA4 ΔarnT6 mutations) and TLR5 (due to the ΔfliC180 and Δ(hin-fljBA)-219 mutations) that are on the surface of many cell types in the vaccinated animal host. After invasion into host cells and escape from the SCV (due to the ΔsifA26 mutation), χ12661 will rapidly lyse (due to the Δalr-3 ΔdadB4 ΔasdA33 mutations) to liberate peptidoglycan-derived components to interact with internal Nod1 and Nod2 and DNA partially degraded due to the ΔrecA62 mutation to generate CpG motifs that will interact with TLR9 (also on the internal membrane surfaces of host cells). Thus, the administration of χ12661 will stimulate induction of innate immunity by multiple means.

Alternatively, if the Family A SDAAS strain lyses too rapidly to minimize the impact of stimulating innate immunity via Nod1, Nod2 and TLR9 that requires entry into host cells prior to lysis, we can use a Family B SDAAS strain as the co-administered adjuvant Family B SDAAS strains possess sugar-regulated expression of genes for peptidoglycan precursors such that lysis occurs after several cell divisions in vivo. This provides more time for invasion of the SDAAS strain into host cells prior to lysis. In such a case we could use the Family B strain χ12626 ($\Delta P_{asdA55}$::TT araC $P_{araBAD}$ asd Δalr-3 $\Delta P_{dadB66}$::TT araC $P_{araBAD}$ dadB ΔfliC180 ΔpagP81::$P_{lpp}$lpxE ΔpagL7 ΔlpxR9 Δ(hin-fljBA)-219 ΔarnT6 ΔeptA4 ΔsifA26 ΔwbaP45). Since the Family B SDAAS strain increases in number due to several cell divisions prior to lysis, there is an enhanced probability of toxicity due to released lipid A (even though modified by the ΔpagL7 ΔlpxR9 ΔarnT6 ΔeptA4 mutations). We therefore included the ΔpagP81::$P_{lpp}$lpxE mutation that eliminated the 1' phosphate on lipid A responsible for most of the toxicity of lipid A [22]. Other mutations and associated phenotypes are similar in the Family A and B strains or they could be identical. For example, the ΔwbaP45 mutation in χ12626, which eliminates the LPS O-antigen to expose the LPS core, enhances recruitment via interaction with TLR4.

Example 7

Use of PIESV Constructs to Vaccinate Animal Hosts With Infections by *Helicobacter* Strains Closely Related to *H. pylori*

*Helicobacter* species are prevalently associated with chronic stomach ailments and disease in various animal species. *H. suis* infects pigs and causes disease and economic losses in the pork industry [24]. *H. suis* is also reasonably prevalent in humans and contributes to gastric stress and disease [24]. Since the antigen genes in *H. pylori* for the four identified protective antigens UreA, UreB, NapA and HapA are all present in *S. suis* and have sizes and amino acid sequences that are very similar (see Table 4), it is possible that the vaccine constructs χ12615 (pG8R230) and χ12615 (pG8R262) would induce some level of protective immunity to vaccinated pigs against infection and disease by *H. suis*. Although *S.* Typhimurium vectored vaccines work reasonably well in swine, it might be preferable to use *S.* Choleraesuis vaccine vector with the regulated delayed lysis phenotype since *S.* Choleraesuis is host-adapted to swine as a very invasive *S. enterica* serotype.

TABLE 4

Comparison in *Helicobacter pylori* and in *Helicobacter suis* gene sequences

| Antigen | Size HP(aa/bp) | Size HS(aa/bp) | Signal peptide HP | Signal peptide HS | Identity % HP to HS | Positive % HP to HS |
|---|---|---|---|---|---|---|
| UreA | 238/717 | 236/711 | — | — | 79.9 | 90.0 |
| UreB | 569/1710 | 569/1710 | — | — | 86.6 | 93.0 |
| HpaA | 260/783 | 251/756 | 27/28 | 18/19 | 56.0 | 77.0 |
| NapA | 144/435 | 146/441 | — | — | 70.1 | 86.0 |
| CagA | 1247/3743 | — | — | — | — | — |
| VacA | 961/2886 | — | 33/34 | — | — | — |

Signal peptide prediction by SignalP 5.0
Identity and Positive (similarity) by NCBI blasP

REFERENCES FOR EXAMPLES 5-7

1. Griffin A J, McSorley S J. 2011. Generation of *Salmonella*-specific Th1 cells requires sustained antigen stimulation. Vaccine 29:2697-2704.
2. Wang S, Shi H, Li Y, Shi Z, Zhang X, Baek C H, Mothershead T, Curtiss R, III. 2013. A colanic acid operon deletion mutation enhances induction of early antibody responses by live attenuated *Salmonella* vaccine strains. Infect Immun 81:3148-3162.
3. Pando J M, Karlinsey J E, Lara J C, Libby S J, Fang F C. 2017. The Rcs-Regulated Colanic Acid Capsule Maintains Membrane Potential in *Salmonella enterica* serovar Typhimurium. mBio 8:200808-17.
4. Mao Y, Doyle M P, Chen J. 2001. Insertion mutagenesis of wca reduces acid and heat tolerance of enterohemorrhagic *Escherichia coli* O157:H7. J Bacteriol 183:3811-3815.
5. Ophir T, Gutnick D L. 1994. A role for exopolysaccharides in the protection of microorganisms from desiccation. Appl Environ Microbiol 60:740-745.
6. Chen J, Lee SM, Mao Y. 2004. Protective effect of exopolysaccharide colanic acid of *Escherichia coli* O157: H7 to osmotic and oxidative stress. Int J Food Microbiol 93:281-286.
7. Ranjit D K, Young K D. 2016. Colanic Acid Intermediates Prevent De Novo Shape Recovery of *Escherichia coli* Spheroplasts, Calling into Question Biological Roles Previously Attributed to Colanic Acid. J Bacteriol 198:1230-1240.
8. Adcox H E, Vasicek E M, Dwivedi V, Hoang K V, Turner J, Gunn J S. 2016. *Salmonella* Extracellular Matrix Components Influence Biofilm Formation and Gallbladder Colonization. Infect Immun 84:3243-3251.
9. Crawford R W, Gibson D L, Kay W W, Gunn J S. 2008. Identification of a bile-induced exopolysaccharide required for *Salmonella* biofilm formation on gallstone surfaces. Infect Immun 76:5341-5349.
10. Gibson D L, White A P, Snyder S D, Martin S, Heiss C, Azadi P, Surette M, Kay W W. 2006. *Salmonella* produces an O-antigen capsule regulated by AgfD and important for environmental persistence. J Bacteriol 188:7722-7730.
11. Zhang X, Wanda S Y, Brenneman K, Kong W, Roland K, Curtiss R, III. 2011. Improving *Salmonella* vector with rec mutation to stabilize the DNA cargoes. BMC Microbiol 11:31.
12. Ashraf S, Kong W, Wang S, Yang J, Curtiss R, III. 2011. Protective cellular responses elicited by vaccination with influenza nucleoprotein delivered by a live recombinant attenuated *Salmonella* vaccine. Vaccine 29:3990-4002.
13. Juárez-Rodríguez M D, Yang J, Kader R, Alamuri P, Curtiss R, III, Clark-Curtiss J E. 2012. Live attenuated *Salmonella* vaccines displaying regulated delayed lysis and delayed antigen synthesis to confer protection against *Mycobacterium tuberculosis*. Infect Immun 80:815-831.
14. Jiang Y, Mo H, Willingham C, Wang S, Park J Y, Kong W, Roland K L, Curtiss R, III. 2015. Protection Against Necrotic Enteritis in Broiler Chickens by Regulated Delayed Lysis *Salmonella* Vaccines. Avian Dis 59:475-485.
15. Kong W, Wang X, Fields E, Okon B, Jenkins M C, Wilkins G, Brovold M, Golden T, Gonzales A, Golden G, Clark-Curtiss J E, Curtiss R, III. 2020. Mucosal delivery of a self-destructing *Salmonella*-based vaccine inducing immunity against Eimeria Manuscript format and headings for Avian Diseases 64:254-268 2020 Mar. 9. doi: 10.1637/aviandiseases-D-19-00159. Online ahead of print. PMID: 33112952
16. Irvine K L, Gangloff M, Walsh C M, Spring D R, Gay N J, Bryant C E. 2014. Identification of key residues that confer Rhodobacter sphaeroides LPS activity at horse TLR4/MD-2. PLoS One 9:e98776.
17. Lohmann K L, Vandenplas M L, Barton M H, Bryant C E, Moore J N. 2007. The equine TLR4/MD-2 complex mediates recognition of lipopolysaccharide from Rhodobacter sphaeroides as an agonist. J Endotoxin Res 13:235-242.
18. Lohmann K L, Vandenplas M, Barton M H, Moore J N. 2003. Lipopolysaccharide from Rhodobacter sphaeroides is an agonist in equine cells. J Endotoxin Res 9:33-37.
19. Walsh C, Gangloff M, Monie T, Smyth T, Wei B, McKinley T J, Maskell D, Gay N, Bryant C. 2008. Elucidation of the MD-2/TLR4 interface required for signaling by lipid IVa. J Immunol 181:1245-1254.
20. van Miert A S, Frens J. 1968. The reaction of different animal species to bacterial pyrogens. Zentralbl Veterinarmed A 15:532-543.

21. De Boever S, Beyaert R, Vandemaele F, Baert K, Duchateau L, Goddeeris B, De Backer P, Croubels S. 2008. The influence of age and repeated lipopolysaccharide administration on body temperature and the concentration of interleukin-6 and IgM antibodies against lipopolysaccharide in broiler chickens. Avian Pathol 37:39-44.
22. Kong Q, Six D A, Roland K L, Liu Q, Gu L, Reynolds C M, Wang X, Raetz C R, Curtiss R, III. 2011. *Salmonella* synthesizing 1-dephosphorylated lipopolysaccharide exhibits low endotoxic activity while retaining its immunogenicity. J Immunol 187:412-423.
23. Łaniewski P, Baek C H, Roland K L, Curtiss R, III. 2017. Analysis of Spleen-Induced Fimbria Production in Recombinant Attenuated *Salmonella enterica* Serovar Typhimurium Vaccine Strains. MBio 8:e01189-17.
24. Flahou, B., Van Deun, K., Pasmans, F., Smet, A., Volf, J., Rychlik, I., Ducatelle, R., Haesebrouck, F. 2012. The local immune response of mice after *Helicobacter suis* infection: strain differences and distinction with *Helicobacter pylori*. Vet. Research 43:article 75.

REFERENCES FOR BACKGROUND AND EXAMPLES 1-4

1. Blanchard T G, Czinn S J. Identification of *Helicobacter pylori* and the evolution of an efficacious childhood vaccine to protect against gastritis and peptic ulcer disease. Pediatric research. 2017; 81(1-2):170-6.
2. Correa P, Piazuelo M B. *Helicobacter pylori* infection and gastric adenocarcinoma. US gastroenterology & hepatology review. 2011; 7(1):59-64.
3. Graham D Y, Malaty H M, Evans D G, Evans D J, Jr., Klein P D, Adam E. Epidemiology of *Helicobacter pylori* in an asymptomatic population in the United States. Effect of age, race, and socioeconomic status. Gastroenterology. 1991; 100(6):1495-501.
4. Ghasemi A, Mohammad N, Mautner J, Taghipour Karsabet M, Amani J, Ardjmand A, et al. Immunization with a recombinant fusion protein protects mice against *Helicobacter pylori* infection. Vaccine. 2018; 36(34):5124-32.
5. Yamaoka Y, Kato M, Asaka M. Geographic differences in gastric cancer incidence can be explained by differences between *Helicobacter pylori* strains. Internal medicine. 2008; 47(12):1077-83.
6. Talebi Bezmin Abadi A. Vaccine against *Helicobacter pylori*: Inevitable approach. World journal of gastroenterology: WJG. 2016; 22(11):3150-7.
7. Graham D Y, Shiotani A. New concepts of resistance in the treatment of *Helicobacter pylori* infections. Nature clinical practice Gastroenterology & hepatology. 2008; 5(6):321-31.
8. Capurro M I, Greenfield L K, Prashar A, Xia S, Abdullah M, Wong H, et al. VacA generates a protective intracellular reservoir for *Helicobacter pylori* that is eliminated by activation of the lysosomal calcium channel TRPML1. Nat Microbiol. 2019; 4(8):1411-23.
9. Megraud F. *H. pylori* antibiotic resistance: prevalence, importance, and advances in testing. Gut. 2004; 53(9): 1374-84.
10. Sepulveda A R. *Helicobacter*, Inflammation, and Gastric Cancer. Current pathobiology reports. 2013; 1(1):9-18.
11. Ermak T H, Giannasca P J, Nichols R, Myers G A, Nedrud J, Weltzin R, et al. Immunization of mice with urease vaccine affords protection against *Helicobacter pylori* infection in the absence of antibodies and is mediated by MHC class II-restricted responses. J Exp Med. 1998; 188(12):2277-88.
12. Lee J S, Jung I D, Lee C M, Park J W, Chun S H, Jeong S K, et al. Outer membrane protein a of *Salmonella enterica* serovar Typhimurium activates dendritic cells and enhances Th1 polarization. BMC Microbiol. 2010; 10:263.
13. Sawai N, Kita M, Kodama T, Tanahashi T, Yamaoka Y, Tagawa Y, et al. Role of gamma interferon in *Helicobacter pylori*-induced gastric inflammatory responses in a mouse model. Infect Immun. 1999; 67(1):279-85.
14. Hase K, Kawano K, Nochi T, Pontes G S, Fukuda S, Ebisawa M, et al. Uptake through glycoprotein 2 of FimH(+) bacteria by M cells initiates mucosal immune response. Nature. 2009; 462(7270):226-30.
15. Sirard J C, Niedergang F, Kraehenbuhl J P. Live attenuated *Salmonella*: a paradigm of mucosal vaccines. Immunol Rev. 1999; 171:5-26.
16. Chatfield S N, Strugnell R A, Dougan G. Live *Salmonella* as vaccines and carriers of foreign antigenic determinants. Vaccine. 1989; 7(6):495-8.
17. Kong W, Wang X, Fields E, Okon B, Jenkins M C, Wilkins G, et al. Mucosal Delivery of a Self-destructing *Salmonella*-Based Vaccine Inducing Immunity Against Eimeria. Avian Dis. 2020; 64(3):254-68.
18. Clark-Curtiss J E, Curtiss R, 3rd. *Salmonella* Vaccines: Conduits for Protective Antigens. J Immunol. 2018; 200 (1):39-48.
19. Curtiss R, III. Bacterial infectious disease control by vaccine development. J Clin Invest. 2002; 110(8):1061-6
20. Cheminay C, Hensel M. Rational design of *Salmonella* recombinant vaccines. International journal of medical microbiology: IJMM. 2008; 298(1-2):87-98.
21. Cardenas L, Clements J D. Oral immunization using live attenuated *Salmonella* spp as carriers of foreign antigens. Clinical microbiology reviews. 1992; 5(3):328-42.
22. Curtiss R, III, Xin W, Li Y, Kong W, Wanda S Y, Gunn B, et al. New technologies in using recombinant attenuated *Salmonella* vaccine vectors. Crit Rev Immunol. 2010; 30(3):255-70.
23. Atkins H S, Morton M, Griffin K F, Stokes M G, Nataro J P, Titball R W. Recombinant *Salmonella* vaccines for biodefence. Vaccine. 2006; 24(15):2710-7.
24. Wang S, Kong Q, Curtiss R, III. New technologies in developing recombinant attenuated *Salmonella* vaccine vectors. Microbial pathogenesis. 2013; 58:17-28.
25. Mantis N J, Forbes S J. Secretory IgA: arresting microbial pathogens at epithelial borders. Immunological investigations. 2010; 39(4-5):383-406.
26. Brandtzaeg P. Role of mucosal immunity in influenza. Developments in biologicals. 2003; 115:39-48.
27. Brandtzaeg P. Role of secretory antibodies in the defence against infections. International journal of medical microbiology: IJMM. 2003; 293(1):3-15.
28. Brandtzaeg P, Farstad I N, Haraldsen G. Regional specialization in the mucosal immune system: primed cells do not always home along the same track. Immunology today. 1999; 20(6):267-77.
29. Brandtzaeg P, Farstad I N, Johansen F E, Morton H C, Norderhaug I N, Yamanaka T. The B-cell system of human mucosae and exocrine glands. Immunol Rev. 1999; 171:45-87.
30. Woof J M, Mestecky J. Mucosal immunoglobulins. Immunol Rev. 2005; 206:64-82.
31. Moon J J, McSorley S J. Tracking the dynamics of *Salmonella* specific T cell responses. Curr Top Microbiol Immunol. 2009; 334:179-98.

32. Srinivasan A, McSorley S J. Activation of *Salmonella*-specific immune responses in the intestinal mucosa. Arch Immunol Ther Exp (Warsz). 2006; 54(1):25-31.
33. Griffin A J, McSorley S J. Development of protective immunity to *Salmonella*, a mucosal pathogen with a systemic agenda. Mucosal Immunol. 2011; 4(4):371-82.
34. Broz P, Ohlson M B, Monack D M. Innate immune response to *Salmonella* typhimurium, a model enteric pathogen. Gut Microbes. 2012; 3(2):62-70.
35. Tam M A, Rydstrom A, Sundquist M, Wick M J. Early cellular responses to *Salmonella* infection: dendritic cells, monocytes, and more. Immunol Rev. 2008; 225:140-62.
36. Hopkins S, Kraehenbuhl J P, Schodel F, Potts A, Peterson D, de Grandi P, et al. A recombinant *Salmonella* typhimurium vaccine induces local immunity by four different routes of immunization. Infect Immun 1995; 63(9):3279-86.
37. Srinivasan J, Tinge S, Wright R, Herr JC, Curtiss R, III. Oral immunization with attenuated *Salmonella* expressing human sperm antigen induces antibodies in serum and the reproductive tract. Biology of reproduction. 1995; 53(2): 462-71.
38. Shi H, Wang S, Roland K L, Gunn B M, Curtiss R, III. Immunogenicity of a live recombinant *Salmonella enterica* serovar Typhimurium vaccine expressing pspA in neonates and infant mice born from naive and immunized mothers. Clin Vaccine Immunol. 2010; 17(3):363-71.
39. Curtiss R, III., Wanda S Y, Gunn B M, Zhang X, Tinge S A, Ananthnarayan V, et al. *Salmonella enterica* serovar Typhimurium strains with regulated delayed attenuation in vivo. Infect Immun. 2009; 77(3):1071-82.
40. Kong W, Wanda S Y, Zhang X, Bollen W, Tinge S A, Roland K L, et al. Regulated programmed lysis of recombinant *Salmonella* in host tissues to release protective antigens and confer biological containment. Proc Natl Acad Sci USA. 2008; 105(27):9361-6.
41. Collins L V, Attridge S, Hackett J. Mutations at rfc or pmi attenuate *Salmonella* typhimurium virulence for mice. Infect Immun 1991; 59(3):1079-85.
42. Sanapala S, Rahav H, Patel H, Sun W, Curtiss R, III. Multiple antigens of *Yersinia pestis* delivered by live recombinant attenuated *Salmonella* vaccine strains elicit protective immunity against plague. Vaccine. 2016; 34(21):2410-6.
43. Jiang Y, Mo H, Willingham C, Wang S, Park J Y, Kong W, et al. Protection Against Necrotic Enteritis in Broiler Chickens by Regulated Delayed Lysis *Salmonella* Vaccines. Avian diseases. 2015; 59(4):475-85.
44. Muralinath M, Kuehn M J, Roland K L, Curtiss R, III. Immunization with *Salmonella enterica* serovar Typhimurium-derived outer membrane vesicles delivering the pneumococcal protein PspA confers protection against challenge with *Streptococcus pneumoniae*. Infect Immun 2011; 79(2):887-94.
45. Kang H Y, Srinivasan J, Curtiss R, 3rd. Immune responses to recombinant pneumococcal PspA antigen delivered by live attenuated *Salmonella enterica* serovar typhimurium vaccine. Infect Immun. 2002; 70(4):1739-49.
46. Oleastro M, Menard A. The Role of *Helicobacter pylori* Outer Membrane Proteins in Adherence and Pathogenesis. Biology. 2013; 2(3):1110-34.
47. Hatakeyama M. *Helicobacter pylori* CagA and gastric cancer: a paradigm for hit-and-run carcinogenesis. Cell Host Microbe. 2014; 15(3):306-16.
48. Mohammad N, Karsabet M T, Amani J, Ardjmand A, Zadeh M R, Gholi M K, et al. In Silico Design of a Chimeric Protein Containing Antigenic Fragments of *Helicobacter pylori*; A Bioinformatic Approach. The open microbiology journal. 2016; 10:97-112.
49. Satin B, Del Giudice G, Della Bianca V, Dusi S, Laudanna C, Tonello F, et al. The neutrophil-activating protein (HP-NAP) of *Helicobacter pylori* is a protective antigen and a major virulence factor. J Exp Med. 2000; 191(9):1467-76.
50. Nell S, Kennemann L, Schwarz S, Josenhans C, Suerbaum S. Dynamics of Lewis b binding and sequence variation of the babA adhesin gene during chronic *Helicobacter pylori* infection in humans. MBio. 2014; 5(6): e02281-14.
51. Moyat M, Velin D. Use of VacA as a Vaccine Antigen. Toxins. 2016; 8(6).
52. Gagnaire A, Nadel B, Raoult D, Neefjes J, Gorvel J P. Collateral damage: insights into bacterial mechanisms that predispose host cells to cancer. Nat Rev Microbiol. 2017; 15(2):109-28.
53. Del Giudice G, Malfertheiner P, Rappuoli R. Development of vaccines against *Helicobacter pylori*. Expert review of vaccines. 2009; 8(8):1037-49.
54. Carlsohn E, Nystrom J, Bolin I, Nilsson C L, Svennerholm A M. HpaA is essential for *Helicobacter pylori* colonization in mice. Infect Immun 2006; 74(2):920-6.
55. Ghasemi A, Mohammad N, Mautner J, Karsabet M T, Ardjmand A, Moniri R. Immunization with recombinant FliD confers protection against *Helicobacter pylori* infection in mice. Molecular immunology. 2018; 94:176-82.
56. Branger C G, Sun W, Torres-Escobar A, Perry R, Roland K L, Fetherston J, et al. Evaluation of Psn, HmuR and a modified LcrV protein delivered to mice by live attenuated *Salmonella* as a vaccine against bubonic and pneumonic *Yersinia pestis* challenge. Vaccine. 2010; 29(2): 274-82.
57. Ghasemi A, Jeddi-Tehrani M, Mautner J, Salari M H, Zarnani A H. Simultaneous immunization of mice with Omp31 and TF provides protection against *Brucella melitensis* infection. Vaccine. 2015; 33(42):5532-8.
58. Teng Y S, Liu Y G, Chen X H, Wang T T, Cheng P, Lv Y P, et al. Decreased IL-17RB expression impairs CD11b. Cell Death Dis. 2019; 10(2):79.
59. Shi Y, Yang Z, Zhang T, Shen L, Li Y, Ding S. SIRT1-targeted miR-543 autophagy inhibition and epithelial-mesenchymal transition promotion in *Helicobacter pylori* CagA-associated gastric cancer. Cell Death Dis. 2019; 10(9):625.
60. Rao X, Huang X, Zhou Z, Lin X. An improvement of the 2^(-delta delta CT) method for quantitative real-time polymerase chain reaction data analysis. Biostat Bioinforma Biomath. 2013; 3(3):71-85.
61. Kaniuk N A, Vinogradov E, Whitfield C. Investigation of the structural requirements in the lipopolysaccharide core acceptor for ligation of O antigens in the genus *Salmonella*: WaaL "ligase" is not the sole determinant of acceptor specificity. J Biol Chem. 2004; 279(35):36470-80.
62. Kong Q, Liu Q, Jansen A M, Curtiss R, III. Regulated delayed expression of rfc enhances the immunogenicity and protective efficacy of a heterologous antigen delivered by live attenuated *Salmonella enterica* vaccines. Vaccine. 2010; 28(37):6094-103.
63. Wang S, Shi H, Li Y, Shi Z, Zhang X, Baek C H, et al. A colanic acid operon deletion mutation enhances induction of early antibody responses by live attenuated *Salmonella* vaccine strains. Infect Immun. 2013; 81(9):3148-62.
64. Juárez-Rodríguez M D, Yang J, Kader R, Alamuri P, Curtiss R, III, Clark-Curtiss J E. Live attenuated *Salmonella* vaccines displaying regulated delayed lysis and delayed antigen synthesis to confer protection against *Mycobacterium tuberculosis*. Infect Immun 2012; 80(2): 815-31.
65. Wang S, Li Y, Scarpellini G, Kong W, Shi H, Baek C H, et al. *Salmonella* vaccine vectors displaying delayed antigen synthesis in vivo to enhance immunogenicity. Infect Immun. 2010; 78(9):3969-80.
66. Xin W, Wanda S Y, Li Y, Wang S, Mo H, Curtiss R, III. Analysis of type II secretion of recombinant pneumococcal PspA and PspC in a *Salmonella enterica* serovar Typhimurium vaccine with regulated delayed antigen synthesis. Infect Immun 2008; 76(7):3241-54.
67. Zhang X, Wanda S Y, Brenneman K, Kong W, Roland K, Curtiss R, III. Improving *Salmonella* vector with rec mutation to stabilize the DNA cargoes. BMC Microbiol. 2011; 11:31.
68. Ashraf S, Kong W, Wang S, Yang J, Curtiss R, III. Protective cellular responses elicited by vaccination with influenza nucleoprotein delivered by a live recombinant attenuated *Salmonella* vaccine. Vaccine. 2011; 29(23): 3990-4002.
69. Kong W, Brovold M, Koeneman B A, Clark-Curtiss J, Curtiss R, III. Turning self-destructing *Salmonella* into a universal DNA vaccine delivery platform. Proc Natl Acad Sci USA. 2012; 109(47):19414-9.
70. Frantz J D B G, Cartwright M E, Crissman J W, Macklin A W, Moronpot R R. Proliferative lesions of the non-glandular and glandular stomach in rats, GI-3, In: Guides for Toxologic Pathology, STP/ARP/AFIP. Washington, DC 1991.
71. Corthésy-Theulaz I E, Hopkins S, Bachmann D, Saldinger P F, Porta N, Haas R, et al. Mice are protected from *Helicobacter pylori* infection by nasal immunization with attenuated *Salmonella* typhimurium phoPc expressing urease A and B subunits. Infect Immun. 1998; 66(2): 581-6.
72. Gómez-Duarte O G, Lucas B, Yan Z X, Panthel K, Haas R, Meyer T F. Protection of mice against gastric colonization by *Helicobacter pylori* by single oral dose immunization with attenuated *Salmonella* typhimurium producing urease subunits A and B. Vaccine. 1998; 16(5):460-71.
73. Liu K Y, Shi Y, Luo P, Yu S, Chen L, Zhao Z, et al. Therapeutic efficacy of oral immunization with attenuated *Salmonella* typhimurium expressing *Helicobacter pylori* CagA, VacA and UreB fusion proteins in mice model. Vaccine. 2011; 29(38):6679-85.
74. Angelakopoulos H, Hohmann E L. Pilot study of phoP/phoQ-deleted *Salmonella enterica* serovar typhimurium expressing *Helicobacter pylori* urease in adult volunteers. Infect Immun 2000; 68(4):2135-41.
75. Amanna I J, Slifka M K. Contributions of humoral and cellular immunity to vaccine-induced protection in humans. Virology. 2011; 411(2):206-15.
76. Bumann D, Metzger W G, Mansouri E, Palme O, Wendland M, Hurwitz R, et al. Safety and immunogenicity of live recombinant *Salmonella enterica* serovar Typhi Ty21a expressing urease A and B from *Helicobacter pylori* in human volunteers. Vaccine. 2001; 20(5-6):845-52.
77. Ernst P B, Pappo J. T-cell-mediated mucosal immunity in the absence of antibody: lessons from *Helicobacter pylori* infection. Acta Odontol Scand. 2001; 59(4):216-21.
78. Rad R, Brenner L, Bauer S, Schwendy S, Layland L, da Costa C P, et al. CD25+/Foxp3+ T cells regulate gastric inflammation and *Helicobacter pylori* colonization in vivo. Gastroenterology. 2006; 131(2):525-37.
79. Naugler W E, Karin M. The wolf in sheep's clothing: the role of interleukin-6 in immunity, inflammation and cancer. Trends Mol Med. 2008; 14(3):109-19.
80. Ouyang W, Kolls J K, Zheng Y. The biological functions of T helper 17 cell effector cytokines in inflammation. Immunity 2008; 28(4):454-67.
81. Chung D R, Kasper D L, Panzo R J, Chitnis T, Grusby M J, Sayegh M H, et al. CD4+ T cells mediate abscess formation in intra-abdominal sepsis by an IL-17-dependent mechanism. J Immunol. 2003; 170(4):1958-63.
82. Kumar P, Chen K, Kolls J K. Th17 cell based vaccines in mucosal immunity. Curr Opin Immunol. 2013; 25(3): 373-80.
83. Lo B C, Shin S B, Canals Hernaez D, Refaeli I, Yu H B, Goebeler V, et al. IL-22 Preserves Gut Epithelial Integrity and Promotes Disease Remission during Chronic. J Immunol. 2019; 202(3):956-65.
84. Al-Alwan L A, Chang Y, Mogas A, Halayko A J, Baglole C J, Martin J G, et al. Differential roles of CXCL2 and CXCL3 and their receptors in regulating normal and asthmatic airway smooth muscle cell migration. J Immunol. 2013; 191(5):2731-41.
85. Lertpiriyapong K, Whary M T, Muthupalani S, Lofgren J L, Gamazon E R, Feng Y, et al. Gastric colonisation with a restricted commensal microbiota replicates the promotion of neoplastic lesions by diverse intestinal microbiota in the *Helicobacter pylori* INS-GAS mouse model of gastric carcinogenesis. Gut. 2014; 63(1):54-63.
86. Ryan K A, Jayaraman T, Daly P, Canchaya C, Curran S, Fang F, et al. Isolation of *lactobacilli* with probiotic properties from the human stomach. Lett Appl Microbiol. 2008; 47(4):269-74.
87. Roos S, Engstrand L, Jonsson H. *Lactobacillus gastricus* sp. *nov.*, *Lactobacillus antri* sp. *nov.*, *Lactobacillus kalixensis* sp. *nov.* and *Lactobacillus ultunensis* sp. *nov.*, isolated from human stomach mucosa. Int J Syst Evol Microbiol. 2005; 55(Pt 1):77-82.
88. Maldonado-Contreras A, Goldfarb K C, Godoy-Vitorino F, Karaoz U, Contreras M, Blaser M J, et al. Structure of the human gastric bacterial community in relation to *Helicobacter pylori* status. ISME J. 2011; 5(4):574-9.
89. Stearns J C, Lynch M D, Senadheera D B, Tenenbaum H C, Goldberg M B, Cvitkovitch D G, et al. Bacterial biogeography of the human digestive tract. Sci Rep. 2011; 1:170.

GENERAL REFERENCES RELATED TO *SALMONELLA* VACCINE VECTORS

DiPetrillo et al. Vaccine (1999), 18:449-459
Metzger et al., Vaccine (2004) 22:2273-2277.

The teachings of the references provided herein are incorporated in their entirety to the extent not inconsistent with the teachings herein.

This disclosure is written to describe the invention to a person having ordinary skill in the art, who will understand that this disclosure is not limited to the specific examples or embodiments described. The examples and embodiments are single instances of the invention which will make a much larger scope apparent to the person having ordinary skill in the art. Unless defined otherwise, all technical and scientific terms used herein have the same meaning as commonly understood by the person having ordinary skill in the art. It is also to be understood that the terminology used herein is for the purpose of describing examples and embodiments only, and is not intended to be limiting, since the scope of the present disclosure will be limited only by the appended claims.

All the features disclosed in this specification (including any accompanying claims, abstract, and drawings) may be replaced by alternative features serving the same, equivalent, or similar purpose, unless expressly stated otherwise. Thus, unless expressly stated otherwise, each feature disclosed is one example only of a generic series of equivalent or similar features. The examples and embodiments described herein are for illustrative purposes only and that various modifications or changes in light thereof will be suggested to the person having ordinary skill in the art and are to be included within the spirit and purview of this application. Many variations and modifications may be made to the embodiments of the disclosure without departing substantially from the spirit and principles of the disclosure. All such modifications and variations are intended to be included herein within the scope of this disclosure. For example, unless otherwise indicated, the present disclosure is not limited to particular materials, reagents, reaction materials, manufacturing processes, or the like, as such can vary. It is also to be understood that the terminology used herein is for purposes of describing particular embodiments only and is not intended to be limiting. It is also possible in the present disclosure that steps can be executed in different sequence where this is logically possible.

What is claimed is:

1. An attenuated derivative of an invasive pathogenic microorganism that undergoes regulated delayed lysis in vivo that comprises an expression construct engineered to synthesize at least one *Helicobacter* protein, the expression construct comprising a polynucleotide sequences encoding the at least one *Helicobacter* protein, wherein upon administration to an animal host, the microorganism expresses and delivers the at least one *Helicobacter* protein to the animal host, wherein the attenuated derivative of an invasive pathogenic microorganism comprises a PIESV.

2. The attenuated derivative of an invasive pathogenic microorganism of claim 1 wherein the microorganism is a gram-negative pathogenic bacterium.

3. The attenuated derivative of an invasive pathogenic microorganism of claim 2 wherein the pathogenic bacterium is of the family Enterobacteriaceae.

4. The attenuated derivative of an invasive pathogenic microorganism claim 3 wherein the bacterium of the family Enterobacteriaceae is a *Salmonella enterica* bacterium.

5. The attenuated derivative of an invasive pathogenic microorganism of claim 1, wherein the attenuated microorganism is (i) attenuated due to the presence of one or more mutations conferring regulated delayed attenuation within the animal host; and/or (ii) modified to enable regulated delayed synthesis of the at least one *Helicobacter* protein encoded by the expression construct in the attenuated microorganism within the animal host.

6. The attenuated derivative of an invasive pathogenic microorganism of claim 1 wherein the expression construct comprises a plasmid that comprises a balanced-lethal plasmid-microorganism combination such that loss of the plasmid leads to death by lysis of the microorganism.

7. The attenuated derivative of an invasive pathogenic microorganism of claim 6, wherein the maintenance of the balanced-lethal plasmid-microorganism combination is dependent on the supply of a sugar present during growth of the microorganism but leads to the ultimate lysis of the microorganism within an animal host since the sugar is unavailable in the animal host.

8. The attenuated derivative of an invasive pathogenic microorganism of claim 1, wherein the at least one *Helicobacter* protein comprises Hp-NAP, HpaA, UreA, UreB, HopM, BabA, Chimeric Protein, CagA, or VacA.

9. The attenuated derivative of an invasive pathogenic microorganism of claim 8, wherein the at least one *Helicobacter* protein comprises two or more *Helicobacter* proteins.

10. The attenuated derivative of an invasive pathogenic microorganism of claim 9, wherein the two or more *Helicobacter* proteins are UreA and UreB.

11. The attenuated derivative of an invasive pathogenic microorganism of claim 9, wherein the two or more *Helicobacter* proteins are HpaA and NapA (Hp-NAP).

12. The attenuated derivative of an invasive pathogenic microorganism of of claim 1, wherein the microorganism is engineered to facilitate biological containment.

13. An attenuated derivative of an invasive pathogenic microorganism that undergoes regulated delayed lysis in vivo that comprises an expression construct engineered to synthesize at least three *Helicobacter* proteins, the expression construct comprising a polynucleotide sequences encoding the at least three *Helicobacter* proteins, wherein upon administration to an animal host, the microorganism expresses and delivers the at least three *Helicobacter* proteins to the animal host, wherein the attenuated derivative of an invasive pathogenic microorganism comprises a PIESV.

14. The attenuated derivative of an invasive pathogenic microorganism of claim 13, wherein the at least three *Helicobacter* proteins are selected from the group consisting of Hp-NAP, HpaA, UreA, UreB, HopM, BabA, CagA, and VacA.

15. The attenuated derivative of an invasive pathogenic microorganism of claim 13, wherein the at least three *Helicobacter* proteins are provided in a chimeric protein.

16. The attenuated derivative of an invasive pathogenic microorganism claim 14, wherein the antigens comprise the following amino acid sequences Hp-NAP (also termed NapA) (SEQ ID No. 20), HpaA (SEQ ID NO. 7), UreA (SEQ ID NO. 11), UreB (SEQ ID NO. 25), HopM (SEQ ID NO. 3), BabA (SEQ ID NO. 18), Chimeric Protein (SEQ ID NO. 22), CagA (SEQ ID NO. 14), VacA (SEQ ID NO. 16).

17. The attenuated derivative of an invasive pathogenic microorganism of claim 9, wherein the two or more *Helicobacter* proteins are (i) VacA and UreA; (ii) VacA and Hp-NAP; (iii) UreA and HpA; (iv) UreB and HpA; or (v) UreB and Hp-NAP.

18. The attenuated derivative of an invasive pathogenic microorganism of claim 1, wherein the attenuated derivative comprises PIESV strain χ12341 or strain χ12615.

* * * * *

```
                        SEQUENCE LISTING

<160> NUMBER OF SEQ ID NOS: 26

<210> SEQ ID NO 1
<211> LENGTH: 2028
<212> TYPE: DNA
<213> ORGANISM: Helicobacter pylori

<400> SEQUENCE: 1
gaagatgacg gattttacat gagcgtgggc tatcaaatcg gtgaagcggt tcaaaaagtg      60
aaaaacactg tagcattgca aaatcttgca gacagatacg ataacttgag caacctttta     120
aaccaataca attacttaaa ttccttagtc aatctagcca gcacgcctag cgcgattacc     180
ggtgcgattg gcaatctaag ctcaagcgcg atcaacctca ctagcgctac caccacttcc     240
cccgcctatc aagctgtggc tttagcgctc aatgccgctg tgggcatgtg gcaagtcata     300
gcctttggta ttagctgcgg ccctggcccc aatcttggcc cagaacattt agaaaatggg     360
ggcgttcgat cgtttgacaa cacgccaaac tacagctaca acaccgtag cggaacgacc      420 accaccactt gcaatggagc cagtaatgta gggcccaatg gcattctatc tagtagtgaa     480
taccaagttc tcaacaccgc ttatcaaact atccaaaccg ctttaaacca aaaccaagga     540
ggcgggatgc ctgccttgaa tagctctaaa aatatggtag tcaatatcaa tcaaactttc     600
acaagaaacc ctacaacaga atacacttac cctaatggaa atggcaatta ttattcaggc     660
ggatcatcaa tcccaatcca gctaaaaatt agtagcgtca atgacgctga aaaccttttg     720
caacaagccg ctactatcat caatgtcctt accacccaaa acccgcatgt gaatggtggc     780
ggtggggcat gggggtttgt cggtcagact gggactgtga tggatatttt tggcgatagc     840
tttaacgcta ttaacgagat gattaaaaac gctcgaacag ccctagcaaa aacccaacag     900
cttaacgcta atgaaaacgc ccaaatcacg caaccagaca atttcaaccc ctacacttcc     960
aaagacaaag ggttcgctca agaaatgctc aacagagcta acgctcaagc agagatttta    1020
aatctagccc aacaagtagc ggacaatttc cacagcattc aagggcctat ccaacaagat    1080
ctagaagaat gcaccgcagg atcggctggt gtgattaacg acaacactta tggttcaggc    1140
tgcgcgtttg tgaaagagac tctcaattct ttagagcaac acaccgctta ttatggcaat    1200
caggtcaatc aggataggggc tttggctcaa accatttga atttttaaaga agcccttaac   1260 accctgaata aagactctac agcgattaat aatggtatct ctcacttgcc taacgctaag    1320
ccacttcaaa acatgacgca tgccactcaa acccctaatt ccccagaagg tttgctcact    1380
tattctttgg ataccaacaa atacaaccaa ctccaaacca tcacgcaaga attaggcaaa    1440
```

| | | | | |
|---|---|---|---|---|
| aaccccttta | ggcgcatcgg | cgtgattgac | tatcaaaaca | ataacggcgc | gatgaatggc | 1500 |
| atcggcgtgc | aagtgggcta | taagcaattc | tttggcaaaa | aaaggaattg | ggggttaagg | 1560 |
| tattatggct | tttttgatta | taaccatgct | tatatcaaat | ctaattttttt | taactcggct | 1620 |
| tctgatgtgt | ggacttatgg | ggtgggaatg | gacgctcttt | ataacttcat | taacgataaa | 1680 |
| aacaccaact | ttttaggcaa | gaataacaag | ctctctgtgg | ggcttttttgg | aggctttgcg | 1740 |
| ttagctggga | cttcgtggct | taattcccaa | caagtgaatt | tgaccatgat | gaatggcatt | 1800 |
| tataacgcta | atgtcagcac | ttctaacttc | caattttttgt | ttgatttagg | tttgagaatg | 1860 |
| aacctcgcta | ggcctaagaa | aaaagacagc | gatcatgccg | ctcagcatgg | cattgaacta | 1920 |
| ggttttaaaa | tccctacgat | caacacaagc | tactattctt | tcatgggcgc | taaactagaa | 1980 |
| taccgaagga | tgtatagcct | ttttctcaat | tatgtgtttg | cttactaa | | 2028 |

```
<210> SEQ ID NO 2
<211> LENGTH: 2063
<212> TYPE: DNA
<213> ORGANISM: Artificial Sequence
<220> FEATURE:
<223> OTHER INFORMATION: Synthetic

<400> SEQUENCE: 2
```

| | | | | | | |
|---|---|---|---|---|---|---|
| ccatggaaga | cgacggcttc | tacatgtccg | tgggctacca | gatcggcgaa | gcggtgcaga | 60 |
| aagtgaaaaa | caccgtggcg | ctgcagaacc | tggcggaccg | ttacgacaac | ctgtccaacc | 120 |
| tgctgaacca | gtacaactac | ctgaactccc | tggtgaacct | ggcgtccacc | ccgtccgcga | 180 |
| tcaccggcgc | gatcggcaac | ctgtcctcct | ccgcgatcaa | cctgacctcc | gcgaccacca | 240 |
| cctccccggc | gtaccaggcg | gtggcgctgg | cgctgaacgc | ggcggtgggc | atgtggcagg | 300 |
| tgatcgcgtt | cggcatctcc | tgcggtcctg | gtccgaacct | gggcccggaa | cacctggaaa | 360 |
| acggcggcgt | gcgttccttc | gacaacaccc | cgaactactc | ctacaacacc | cgttccggca | 420 |
| ccaccaccac | cacctgcaac | ggcgcgtcca | cgtgggccc | gaacggcatc | ctgtcctcct | 480 |
| ccgaatacca | ggtgctgaac | accgcgtacc | agaccatcca | gaccgcgctg | aaccagaacc | 540 |
| agggcggcgg | catgccggcg | ctgaactcct | ccaaaaacat | ggtggtgaac | atcaaccaga | 600 |
| ccttcacccg | taacccgacc | accgaataca | cctacccgaa | cggcaacggc | aactactact | 660 |
| ccggcggctc | ctccatcccg | atccagctga | aaatctcctc | cgtgaacgac | gcggaaaacc | 720 |
| tgctgcagca | ggcggcgacc | atcatcaacg | tgctgaccac | ccagaacccg | cacgtgaacg | 780 |
| gcggcggcgg | cgcgtgggc | ttcgtgggcc | agaccggcac | cgtgatggac | atcttcggcg | 840 |
| actccttcaa | cgcgatcaac | gaaatgatca | aaaacgcgcg | taccgcgctg | gcgaaaaccc | 900 |
| agcagctgaa | cgcgaacgaa | aacgcgcaga | tcacccagcc | ggacaacttc | aacccgtaca | 960 |
| cctccaaaga | caaaggcttc | gcgcaggaaa | tgctgaaccg | tgcgaacgcg | caggcggaaa | 1020 |
| tcctgaacct | ggcgcagcag | gtggcggaca | acttccactc | catccagggc | ccgatccagc | 1080 |
| aggacctgga | agaatgcacc | gcgggctccg | cgggcgtgat | caacgacaac | acctacggct | 1140 |
| ccggctgcgc | gttcgtgaaa | gaaaccctga | actccctgga | acagcacacc | gcgtactacg | 1200 |
| gcaaccaggt | gaaccaggac | cgtgcgctgg | cgcagaccat | cctgaacttc | aaagaagcgc | 1260 |
| tgaacacccct | gaacaaagac | tccaccgcga | tcaacaacgg | catctcccac | ctgccgaacg | 1320 |
| cgaaaccgct | gcagaacatg | acccacgcga | cccagaaccc | gaactccccg | gaaggcctgc | 1380 |
| tgacctactc | cctggacacc | aacaaataca | ccagctgca | gaccatcacc | caggaactgg | 1440 |
| gcaaaaaccc | gttccgtcgt | atcggcgtga | tcgactacca | gaacaacaac | ggcgcgatga | 1500 |

```
acggcatcgg cgtgcaggtg ggctacaaac agttcttcgg caaaaaacgt aactggggcc   1560
tgcgttacta cggcttcttc gactacaacc acgcgtacat caaatccaac ttcttcaact   1620
ccgcgtccga cgtgtggacc tacggcgtgg gcatggacgc gctgtacaac ttcatcaacg   1680
acaaaaacac caacttcctg ggcaaaaaca caaactgtc cgtgggcctg ttcggcggct   1740
tcgcgctggc gggcacctcc tggctgaact cccagcaggt gaacctgacc atgatgaacg   1800
gcatctacaa cgcgaacgtg tccacctcca acttccagtt cctgttcgac ctgggcctgc   1860
gtatgaacct ggcgcgtccg aaaaaaaaag actccgacca cgcggcgcag cacggcatcg   1920
aactgggctt caaatcccg accatcaaca cctcctacta ctccttcatg ggcgcgaaac   1980
tggaataccg tcgtatgtac tccctgttcc tgaactacgt gttcgcgtac caccaccacc   2040
accaccacta acccggggga tcc                                          2063
```

<210> SEQ ID NO 3
<211> LENGTH: 681
<212> TYPE: PRT
<213> ORGANISM: Artificial Sequence
<220> FEATURE:
<223> OTHER INFORMATION: Synthetic

<400> SEQUENCE: 3

```
Glu Asp Asp Gly Phe Tyr Met Ser Val Gly Tyr Gln Ile Gly Glu Ala
1               5                   10                  15

Val Gln Lys Val Lys Asn Thr Val Ala Leu Gln Asn Leu Ala Asp Arg
            20                  25                  30

Tyr Asp Asn Leu Ser Asn Leu Leu Asn Gln Tyr Asn Tyr Leu Asn Ser
        35                  40                  45

Leu Val Asn Leu Ala Ser Thr Pro Ser Ala Ile Thr Gly Ala Ile Gly
    50                  55                  60

Asn Leu Ser Ser Ser Ala Ile Asn Leu Thr Ser Ala Thr Thr Thr Ser
65                  70                  75                  80

Pro Ala Tyr Gln Ala Val Ala Leu Ala Leu Asn Ala Ala Val Gly Met
                85                  90                  95

Trp Gln Val Ile Ala Phe Gly Ile Ser Cys Gly Pro Gly Pro Asn Leu
            100                 105                 110

Gly Pro Glu His Leu Glu Asn Gly Gly Val Arg Ser Phe Asp Asn Thr
        115                 120                 125

Pro Asn Tyr Ser Tyr Asn Thr Arg Ser Gly Thr Thr Thr Thr Thr Cys
    130                 135                 140

Asn Gly Ala Ser Asn Val Gly Pro Asn Gly Ile Leu Ser Ser Ser Glu
145                 150                 155                 160

Tyr Gln Val Leu Asn Thr Ala Tyr Gln Thr Ile Gln Thr Ala Leu Asn
                165                 170                 175

Gln Asn Gln Gly Gly Gly Met Pro Ala Leu Asn Ser Ser Lys Asn Met
            180                 185                 190

Val Val Asn Ile Asn Gln Thr Phe Thr Arg Asn Pro Thr Thr Glu Tyr
        195                 200                 205

Thr Tyr Pro Asn Gly Asn Gly Asn Tyr Tyr Ser Gly Gly Ser Ser Ile
    210                 215                 220

Pro Ile Gln Leu Lys Ile Ser Ser Val Asn Asp Ala Glu Asn Leu Leu
225                 230                 235                 240

Gln Gln Ala Ala Thr Ile Ile Asn Val Leu Thr Thr Gln Asn Pro His
                245                 250                 255
```

-continued

Val Asn Gly Gly Gly Ala Trp Gly Phe Val Gly Gln Thr Gly Thr
            260             265             270

Val Met Asp Ile Phe Gly Asp Ser Phe Asn Ala Ile Asn Glu Met Ile
        275                 280                 285

Lys Asn Ala Arg Thr Ala Leu Ala Lys Thr Gln Gln Leu Asn Ala Asn
    290                 295                 300

Glu Asn Ala Gln Ile Thr Gln Pro Asp Asn Phe Asn Pro Tyr Thr Ser
305                 310                 315                 320

Lys Asp Lys Gly Phe Ala Gln Glu Met Leu Asn Arg Ala Asn Ala Gln
                325                 330                 335

Ala Glu Ile Leu Asn Leu Ala Gln Gln Val Ala Asp Asn Phe His Ser
            340                 345                 350

Ile Gln Gly Pro Ile Gln Gln Asp Leu Glu Glu Cys Thr Ala Gly Ser
        355                 360                 365

Ala Gly Val Ile Asn Asp Asn Thr Tyr Gly Ser Gly Cys Ala Phe Val
    370                 375                 380

Lys Glu Thr Leu Asn Ser Leu Glu Gln His Thr Ala Tyr Tyr Gly Asn
385                 390                 395                 400

Gln Val Asn Gln Asp Arg Ala Leu Ala Gln Thr Ile Leu Asn Phe Lys
                405                 410                 415

Glu Ala Leu Asn Thr Leu Asn Lys Asp Ser Thr Ala Ile Asn Asn Gly
            420                 425                 430

Ile Ser His Leu Pro Asn Ala Lys Pro Leu Gln Asn Met Thr His Ala
        435                 440                 445

Thr Gln Asn Pro Asn Ser Pro Glu Gly Leu Leu Thr Tyr Ser Leu Asp
450                 455                 460

Thr Asn Lys Tyr Asn Gln Leu Gln Thr Ile Thr Gln Glu Leu Gly Lys
465                 470                 475                 480

Asn Pro Phe Arg Arg Ile Gly Val Ile Asp Tyr Gln Asn Asn Asn Gly
                485                 490                 495

Ala Met Asn Gly Ile Gly Val Gln Val Gly Tyr Lys Gln Phe Phe Gly
            500                 505                 510

Lys Lys Arg Asn Trp Gly Leu Arg Tyr Tyr Gly Phe Phe Asp Tyr Asn
        515                 520                 525

His Ala Tyr Ile Lys Ser Asn Phe Phe Asn Ser Ala Ser Asp Val Trp
    530                 535                 540

Thr Tyr Gly Val Gly Met Asp Ala Leu Tyr Asn Phe Ile Asn Asp Lys
545                 550                 555                 560

Asn Thr Asn Phe Leu Gly Lys Asn Asn Lys Leu Ser Val Gly Leu Phe
                565                 570                 575

Gly Gly Phe Ala Leu Ala Gly Thr Ser Trp Leu Asn Ser Gln Gln Val
            580                 585                 590

Asn Leu Thr Met Met Asn Gly Ile Tyr Asn Ala Asn Val Ser Thr Ser
        595                 600                 605

Asn Phe Gln Phe Leu Phe Asp Leu Gly Leu Arg Met Asn Leu Ala Arg
    610                 615                 620

Pro Lys Lys Lys Asp Ser Asp His Ala Ala Gln His Gly Ile Glu Leu
625                 630                 635                 640

Gly Phe Lys Ile Pro Thr Ile Asn Thr Ser Tyr Tyr Ser Phe Met Gly
                645                 650                 655

Ala Lys Leu Glu Tyr Arg Arg Met Tyr Ser Leu Phe Leu Asn Tyr Val
            660                 665                 670

Phe Ala Tyr His His His His His His

<210> SEQ ID NO 4
<211> LENGTH: 63
<212> TYPE: DNA
<213> ORGANISM: Helicobacter pylori

<400> SEQUENCE: 4
atgaaaatca aaaatctctc ctttgctctc tctttctctc tcatggcttc attatcaagg    60
gct                                                                  63

<210> SEQ ID NO 5
<211> LENGTH: 678
<212> TYPE: DNA
<213> ORGANISM: Helicobacter pylori

<400> SEQUENCE: 5
gatggaatgc ctgcaaaaca gcagcacaat aatacgggcg agtcagtgga gttgcatttc    60
cactatccta ttaaaggcaa gcaagagcct aaaaacagcc atttagtcgt tttgatcgaa   120
cctaaaatag agatcaataa agttatccct gaaagttatc aaaaagagtt tgagaagtct   180
ttgtttctcc agttgagtag ttttttagag agaaaaggct atagcgtttc gcaatttaaa   240
gatgctagcg aaatccctca agacatcaaa gaaaaagcgt tgctcgtttt acgcatggat   300
gggaatgtgg ctatcttgga agatattgta gaagagagcg atgcgcttag cgaagaaaaa   360
gtgatagaca tgtcttcagg gtatttgaac ttgaattttg ttgagccaaa aagtgaagat   420
attatccata gttttggtat tgatgtttca aagattaagg ctgtgattga agagtggaa   480 ttgcggcgca ccaattctgg aggttttgtc cccaaaactt tgtgcatag gattaaggaa    540 accgatcatg atcaagccat tagaaaaatc atgaatcaag cctatcacaa agtgatggtg   600
catattacca aagagttaag caaaaaacac atggaacatt atgaaaaagt ttctagtgaa   660
atgaaaaaac gaaagtag                                                 678

<210> SEQ ID NO 6
<211> LENGTH: 713
<212> TYPE: DNA
<213> ORGANISM: Artificial Sequence
<220> FEATURE:
<223> OTHER INFORMATION: Synthetic

<400> SEQUENCE: 6
ccatggacgg catgccggcg aaacagcagc acaacaacac cggcgaatcc gtggaactgc    60
acttccacta cccgatcaaa ggcaaacagg aaccgaaaaa ctcccacctg gtggtgctga   120
tcgaaccgaa aatcgaaatc aacaaagtga tcccggaatc ctaccagaaa gaattcgaaa   180
aatccctgtt cctgcagctg tcctccttcc tggaacgtaa aggctactcc gtgtcccagt   240
tcaaagacgc gtccgaaatc ccgcaggaca tcaaagaaaa agcgctgctg gtgctgcgta   300
tggacggcaa cgtggcgatc ctggaagaca tcgtggaaga atccgacgcg ctgtccgaag   360
aaaaagtgat cgacatgtcc tccggctacc tgaacctgaa cttcgtggaa ccgaaatccg   420
aagacatcat ccactccttc ggcatcgacg tgtccaaaat caaagcggtg atcgaacgtg   480
tggaactgcg tcgtaccaac tccggcggct tcgtgccgaa aaccttcgtg caccgtatca   540
aagaaaccga ccacgaccag gcgatccgta aatcatgaa ccaggcgtac cacaaagtga   600
tggtgcacat caccaaagaa ctgtccaaaa acacatggaa cactacgaa aaagtgtcct   660 ccgaaatgaa aaaacgtaaa caccaccacc accaccacta cccgggggga tcc          713

<210> SEQ ID NO 7
<211> LENGTH: 232
<212> TYPE: PRT
<213> ORGANISM: Artificial Sequence
<220> FEATURE:
<223> OTHER INFORMATION: Synthetic

<400> SEQUENCE: 7

Met Asp Gly Met Pro Ala Lys Gln Gln His Asn Asn Thr Gly Glu Ser
1               5                   10                  15

Val Glu Leu His Phe His Tyr Pro Ile Lys Gly Lys Gln Glu Pro Lys
            20                  25                  30

Asn Ser His Leu Val Val Leu Ile Glu Pro Lys Ile Glu Ile Asn Lys
        35                  40                  45

Val Ile Pro Glu Ser Tyr Gln Lys Glu Phe Glu Lys Ser Leu Phe Leu
    50                  55                  60

Gln Leu Ser Ser Phe Leu Glu Arg Lys Gly Tyr Ser Val Ser Gln Phe
65                  70                  75                  80

Lys Asp Ala Ser Glu Ile Pro Gln Asp Ile Lys Glu Lys Ala Leu Leu
                85                  90                  95

Val Leu Arg Met Asp Gly Asn Val Ala Ile Leu Glu Asp Ile Val Glu
            100                 105                 110

Glu Ser Asp Ala Leu Ser Glu Glu Lys Val Ile Asp Met Ser Ser Gly
        115                 120                 125

Tyr Leu Asn Leu Asn Phe Val Glu Pro Lys Ser Glu Asp Ile Ile His
    130                 135                 140

Ser Phe Gly Ile Asp Val Ser Lys Ile Lys Ala Val Ile Glu Arg Val
145                 150                 155                 160

Glu Leu Arg Arg Thr Asn Ser Gly Gly Phe Val Pro Lys Thr Phe Val
                165                 170                 175

His Arg Ile Lys Glu Thr Asp His Asp Gln Ala Ile Arg Lys Ile Met
            180                 185                 190

Asn Gln Ala Tyr His Lys Val Met Val His Ile Thr Lys Glu Leu Ser
        195                 200                 205

Lys Lys His Met Glu His Tyr Glu Lys Val Ser Ser Glu Met Lys Lys
    210                 215                 220

Arg Lys His His His His His His
225                 230

<210> SEQ ID NO 8
<211> LENGTH: 72
<212> TYPE: DNA
<213> ORGANISM: Helicobacter pylori

<400> SEQUENCE: 8
atgaaaaaag gtagtttggc aatcgtttta ggatcgctat tagcgagtgg ggcgttttat    60
acggctctag ct                                                        72

<210> SEQ ID NO 9
<211> LENGTH: 717
<212> TYPE: DNA
<213> ORGANISM: Helicobacter pylori

<400> SEQUENCE: 9
atgaaactca ccccaaaaga gttagacaag ttgatgctcc actatgctgg agaattggct    60
aaaaaacgca agaaaaagg cattaagctt aactatgtag aagcggtagc tttgattagt    120

```
gcccatatta tggaagaagc gagagctggt aaaaagactg cggctgaatt gatgcaagaa    180
gggcgcactc ttttaaaacc ggatgatgtg atggatggcg tggcaagcat gatccatgaa    240
gtgggtattg aagcgatgtt cctgatggg acaaaactcg taaccgtgca taccccctatt    300 gaggccaatg gtaaattagt tcctggtgag ttgttcttaa aaatgaaga catcactatc    360 aacgaaggca aaaagccgt tagcgtgaaa gttaaaaatg ttggcgacag accggttcaa    420
atcggctcac acttccattt ctttgaagtg aatagatgct tagactttga cagagaaaaa    480
actttcggta aacgcttaga cattgcgagc gggacagcgg taaggtttga gcctggcgaa    540
gaaaaatccg tagaattgat tgacattggc ggtaacagaa gaatctttgg atttaacgcg    600
ttggttgata ggcaagcaga caacgaaagc aaaaaaattg ctttacacag agctaaagag    660
cgtggttttc atggcgctaa aagcgatgac aactatgtaa aaacaattaa ggagtaa      717
```

<210> SEQ ID NO 10  
<211> LENGTH: 750  
<212> TYPE: DNA  
<213> ORGANISM: Artificial Sequence  
<220> FEATURE:  
<223> OTHER INFORMATION: Synthetic

<400> SEQUENCE: 10

```
atggaactga ccccgaaaga actggacaaa ctgatgctgc actacgcggg cgaactggcg    60
aagaagcgta agaaaaagg catcaaactg aactacgtgg aagcggtggc gctgatctcc    120
gcgcacatca tggaagaagc gcgtgcgggc aagaagaccg cggcggaact gatgcaggaa    180
ggccgtaccc tgctgaaacc ggacgacgtg atggacggcg tggcgtccat gatccacgaa    240
gtgggcatcg aagcgatgtt cccggacggc accaaactgg tgaccgtgca caccccgatc    300
gaagcgaacg gcaaactggt gccgggcgaa ctgttcctga aaaacgaaga catcaccatc    360
aacgaaggca gaaggcggt gtccgtgaaa gtgaaaaacg tgggcgaccg tccggtgcag    420
atcggctccc acttccactt cttcgaagtg aaccgttgcc tggacttcga ccgtgagaag    480
actttcggca aacgtctgga catcgcgtcc ggcaccgcgg tgcgtttcga accgggcgaa    540
gaaaaatccg tggaactgat cgacatcggc ggcaaccgtc gtatcttcgg cttcaacgcg    600
ctggtggacc gtcaggcgga caacgaatcc aagaagatcg cgctgcaccg tgcgaaagaa    660
cgtggcttcc acggcgcgaa atccgacgac aactacgtga aaccatcaa agaacaccac    720 caccaccacc accactaacc cggggatcc                                       750
```

<210> SEQ ID NO 11  
<211> LENGTH: 245  
<212> TYPE: PRT  
<213> ORGANISM: Artificial Sequence  
<220> FEATURE:  
<223> OTHER INFORMATION: Synthetic

<400> SEQUENCE: 11

```
Met Glu Leu Thr Pro Lys Glu Leu Asp Lys Leu Met Leu His Tyr Ala
1               5                   10                  15

Gly Glu Leu Ala Lys Lys Arg Lys Glu Lys Gly Ile Lys Leu Asn Tyr
            20                  25                  30

Val Glu Ala Val Ala Leu Ile Ser Ala His Ile Met Glu Glu Ala Arg
        35                  40                  45

Ala Gly Lys Lys Thr Ala Ala Glu Leu Met Gln Glu Gly Arg Thr Leu
    50                  55                  60
```

| | | | | | | | | | | | | |
|---|---|---|---|---|---|---|---|---|---|---|---|---|
|Leu|Lys|Pro|Asp|Asp|Val|Met|Asp|Gly|Val|Ala|Ser|Met|Ile|His|Glu|
|65| | | |70| | | |75| | | |80|

Val Gly Ile Glu Ala Met Phe Pro Asp Gly Thr Lys Leu Val Thr Val
                85                  90                  95

His Thr Pro Ile Glu Ala Asn Gly Lys Leu Val Pro Gly Glu Leu Phe
            100                 105                 110

Leu Lys Asn Glu Asp Ile Thr Ile Asn Glu Gly Lys Lys Ala Val Ser
        115                 120                 125

Val Lys Val Lys Asn Val Gly Asp Arg Pro Val Gln Ile Gly Ser His
    130                 135                 140

Phe His Phe Phe Glu Val Asn Arg Cys Leu Asp Phe Asp Arg Glu Lys
145                 150                 155                 160

Thr Phe Gly Lys Arg Leu Asp Ile Ala Ser Gly Thr Ala Val Arg Phe
                165                 170                 175

Glu Pro Gly Glu Glu Lys Ser Val Glu Leu Ile Asp Ile Gly Gly Asn
            180                 185                 190

Arg Arg Ile Phe Gly Phe Asn Ala Leu Val Asp Arg Gln Ala Asp Asn
        195                 200                 205

Glu Ser Lys Lys Ile Ala Leu His Arg Ala Lys Glu Arg Gly Phe His
    210                 215                 220

Gly Ala Lys Ser Asp Asp Asn Tyr Val Lys Thr Ile Lys Glu His His
225                 230                 235                 240

His His His His His
            245

<210> SEQ ID NO 12
<211> LENGTH: 3522
<212> TYPE: DNA
<213> ORGANISM: Helicobacter pylori

<400> SEQUENCE: 12

```
atggctaacg aaaccattga tcaaacaaca acaccagatc aaacggattt tgttccgcaa      60
cgatttatca taatcttca  agtagctttt atcaaagttg ataacgctgt cgcttcattt     120
gatcccgatc aaaaaccaat cgttgataag aatgataggg ataataggca agcttttgag     180
aaaatctcgc aactaaggga agaatacgcc aataaagcga tcaaaaatcc tgccaaaaag     240
aatcagtatt tttcagactt tatcaataag agcaatgatt tgatcaacaa agacaatctc     300
attgctgtag attcttccgt agagagcttt cggaaatttg gggatcagcg ttaccaaatt     360
tttacgagtt gggtgtccct tcaaaaagat ccgtctaaaa tcaacaccca acaaatccga     420
aattttatgg aaaatgtcat acaaccccct atctctgatg ataaagaaaa agcggagttt     480
ttgaggtctg ccaaacaatc ttttgcagga attatcatag gaaccaaat  ccgatcggat     540
gaaaaattca tgggcgtgtt tgatgaatct ttgaaagcaa ggcaagaagc agaaaaaaat     600
gcagagcctg ctggtgggga ttggcttgat attttttat  catttgtatt taacaaaaaa     660
caatcttccg atctcaaaga aacgctcaat caagagccaa ggcctgattt tgaacaaaat     720
ttagccacta ccaccaccga catacaaggc ttaccgcctg aagctagaga tttgcttgat     780
gaaaggggta atttttttaa attcactctt ggtgatgtgg aaatgttgga tgttgaggga     840
gtcgctgaca aggatcctaa ttacaagttc aatcaattat tgatccacaa taacgttcta     900
tcttctgtgc taatggggg  tcatagtaac atagaacctg aaaaagtttc attattgtat     960
ggggataatg tggtcctga  agctaggcat gattggaacg ccaccgttgg ttataaaaac    1020
caacaaggta gcaatgtggc cacactcatt aatgcgcatc ttaataacgg cagtgggtta    1080
```

```
gtcatagcgg gtaatgagga tgggattaaa aaccctagct tctatctcta taaagaagat    1140
caactcacag gtttgaaaca agcgttgagt caagaagaga tccgaaacaa agtggatttc    1200
atggaatttc tcgcgcgaaa caatgctaaa ttagacaact tgagcgagaa agagaaagaa    1260
aaattccaaa ctgagattga agatttccaa aaagaccgta aggcttattt agacgcccta    1320
gggaatgatc acattgcttt tgtttctaaa aaagacccaa acatttagc tttggttact     1380 gagtttggta atggagaggt gagctatacc ctcaaagatt atgggaaaaa acaagataaa    1440
gctttagatg gggagacaaa aaccactctt caaggtagcc taaaatatga tggcgtgatg    1500
tttgtcaatt attccaattt caaatacacc aacgcctcca agagtcctaa taagggcgtg    1560
ggcgctacga atggcgcttc ccatttggaa gcaaattta gcaaggtagc tgtctttaat     1620
ttgcctaatt taaataatct cgctatcact aattatataa ggcgagattt agaagataaa    1680
ttgtgggcta aaggattgtc cccacaagaa gctaataagc tcatcaaaga cttttgaac     1740 agcaacaaag aattggttgg aaaagcttta aacttcaata aagctgtagc tgaagctaaa    1800
aacacaggca attatgatga agtgaaaaaa gctcagaaag atcttgaaaa atctctaagg    1860
aaacgagagc atttagagaa agaagtagcg aaaaaattgg agagcagaaa cgacaacaaa    1920
aatagaatgg aagcaaaagc tcaagctaac agccaaaaag ataagatttt tgcacttatc    1980
aatcaagagc tagtaaggaa gcaagagca gccgctttcg atccgagtct taaagatatc      2040
aggagcgaat tgtctgataa acttgaaaac atcaacaaga atttgaaaga ctttggcaaa    2100 tctttttgatg aactcaaaaa tggcaaaaat aatgatttca gcaaggcaga agaaacgcta   2160
aaagccctta aagactcggt gaaagattta ggtatcaatc cagaatggat ttcaaaaatt    2220
gaaaacctta atgcagcttt gaatgatttc aaaaatggca aaataagga tttcagcaag     2280 gtaacacaag caaaaagcga ccttgaaaat tccattaagg atgtgatcat taatcaaaag    2340
ataacggata aagttgacaa tctcaatcag gctgtatcag agactaaatt aacaggcgat    2400
ttcagtaagg tagagcaagc cctagccgaa ctcaaaagct tgtcattgga tcttggaaaa    2460
aattctgatc tacaaaaatc cgttaaaaat ggtgtaaatg aaccctagt cggtaatggg     2520 ttgtctaaaa cagaagccac aacgctcacc aaaaattttt cggacatcag gaagaattg     2580 aacgagaaat tatttggaaa ttccaataac aataataatg gactcaaaaa caacacagag    2640
cctatttatg ctcaagttaa taaaaagaaa gcaggacaag cagctagccc tgaagagcct    2700
atttatgctc aagttgctaa aaaggtgagt gcaaaaattg accaactcaa cgaagctaca    2760
tcagcaataa atagaaaaat tgaccggatt aacaaaattg catcagcagg taaaggagtg    2820
ggcggtttca gtggagcagg gcgatcagct agccctgaac ccatttacgc tacaattgat    2880
tttgatgagg taaatcaagc aggcttccct cttaggagat acgctggatt tgatgatctc    2940
agtaaagtag ggcttcaag ggaacaagaa ttgactcgta gaattggcga tctcaatcag     3000
gcggtatcag aagctaaaac aggtcatttt gacaacctag aacaaaagat agatgaactc    3060
aaagattcta cgaaaagaa tgctttgaag ttatggggtgg aaagcgcgaa acaagtgcct    3120
actagtttgt cagcgaaatt ggacaattac gctactaaca gccacacacg cattaatagc    3180
aatgtccaaa gtgaacaat caatgaaaaa gcgaccggca tgctgacgca aaaaaaccct     3240
gagtggctca agctcgtgaa taataagata gttgcacata atgtgggaag cgctcatttg    3300
tcagagtatg ataaaattgg attcaaccaa aagaatatga aagattattc tgattcgttc    3360
aagttttcca ccaagttgaa caacgccgta aaagacatta agtctagctt tgtgcaattt    3420
```

```
ttaaccaata catttctac aggatcttac agcttgatga aagcaaatgc ggaacatggc    3480
gtcaaaaata ctaatacaaa aggtggttc caaaaatctt aa                      3522
```

<210> SEQ ID NO 13
<211> LENGTH: 3554
<212> TYPE: DNA
<213> ORGANISM: Artificial Sequence
<220> FEATURE:
<223> OTHER INFORMATION: Synthetic

<400> SEQUENCE: 13

```
ccatggccaa cgaaaccatc gaccagacca ccaccccgga ccagaccgac ttcgtgccgc     60
agcgtttcat caacaacctg caggtggcgt tcatcaaagt ggacaacgcg gtggcgtcct    120
tcgacccgga ccagaaaccg atcgtggaca aaaacgaccg tgacaaccgt caggcgttcg    180
aaaaaatctc ccagctgcgt gaagaatacg cgaacaaagc gatcaaaaac ccggcgaaaa    240
aaaaccagta cttctccgac ttcatcaaca atccaacga cctgatcaac aaagacaacc    300
tgatcgcggt ggactcctcc gtggaatcct tccgtaaatt cggcgaccag cgttaccaga    360
tcttcacctc ctgggtgtcc ctgcagaaag acccgtccaa aatcaacacc cagcagatcc    420
gtaacttcat ggaaaacgtg atccagccgc cgatctccga cgacaaagaa aaagcggaat    480
tcctgcgttc cgcgaaacag tccttcgcgg gcatcatcat cggcaaccag atccgttccg    540
acgaaaaatt catgggcgtg ttcgacgaat ccctgaaagc gcgtcaggaa gcggaaaaaa    600
acgcggaacc ggcgggcggc gactggctgg acatcttcct gtccttcgtg ttcaacaaaa    660
aacagtcctc cgacctgaaa gaaacccctga ccaggaacc cgtccggac ttcgaacaga    720 acctggcgac caccaccacc gacatccagg gcctgccgcc ggaagcgcgt gacctgctgg    780
acgaacgtgg caacttcttc aaattcaccc tgggcgacgt ggaaatgctg gacgtggaag    840
gcgtggcgga caaagacccg aactacaaat caaccagct gctgatccac aacaacgtgc    900
tgtcctccgt gctgatgggc ggccactcca acatcgaacc ggaaaagtg tccctgctgt    960 acggcgacaa cggcggcccg gaagcgcgtc acgactggaa cgcgaccgtg ggctacaaaa   1020
accagcaggg ctccaacgtg gcgacccctga tcaacgcgca cctgaacaac ggctccggcc   1080
tggtgatcgc gggcaacgaa gacggcatca aaaacccgtc cttctacctg tacaaagaag   1140
accagctgac cggcctgaaa caggcgctgt cccaggaaga atccgtaac aaagtggact   1200 tcatggaatt cctggcgcgt aacaacgcga aactggacaa cctgtccgaa aagaaaaag   1260 aaaaattcca gaccgaaatc gaagacttcc agaaagaccg taaagcgtac ctggacgcgc   1320
tgggcaacga ccacatcgcg ttcgtgtcca aaaagaccc gaaacacctg cgctggtga    1380 ccgaattcgg caacgcgaa gtgtcctaca ccctgaaaga ctacggcaaa aacaggaca    1440 aagcgctgga cggcgaaacc aaaaccaccc tgcagggctc cctgaaatac gacggcgtga   1500
tgttcgtgaa ctactccaac ttcaaataca ccaacgcgtc caaatcccccg aacaaaggcg   1560 tgggcgcgac caacggcgcg tcccacctgg aagcgaactt ctccaaagtg gcggtgttca   1620
acctgccgaa cctgaacaac ctggcgatca ccaactacat ccgtcgtgac ctggaagaca   1680
aactgtgggc gaaaggcctg tccccgcagg aagcgaacaa actgatcaaa gacttcctga   1740
actccaacaa agaactggtg gcaaagcgc tgaacttcaa caaagcggtg cggaagcga   1800 aaaacaccgg caactacgac gaagtgaaa aagcgcagaa agacctggaa aaatccctgc   1860
gtaaacgtga cacctggaa aaagaagtgg cgaaaaact ggaatccgt aacgacaaca   1920 aaaccgtat ggaagcgaaa gcgcaggcga actcccagaa agacaaaatc ttcgcgctga   1980
```

```
tcaaccagga agcgtccaaa gaagcgcgtg cggcggcgtt cgacccgtcc ctgaaagaca    2040
tccgttccga actgtccgac aaactggaaa acatcaacaa aaacctgaaa gacttcggca    2100
aatccttcga cgaactgaaa aacggcaaaa caacgactt ctccaaagcg aagaaaccc     2160 tgaaagcgct gaaagactcc gtgaaagacc tgggcatcaa cccggaatgg atctccaaaa    2220
tcgaaaacct gaacgcggcg ctgaacgact tcaaaaacgg caaaaacaaa gacttctcca    2280
aagtgaccca ggcgaaatcc gacctggaaa actccatcaa agacgtgatc atcaaccaga    2340
aaatcaccga caaagtggac aacctgaacc aggcggtgtc cgaaaccaaa ctgaccggcg    2400
acttctccaa agtggaacag cgcgctggcgg aactgaaatc cctgtccctg acctgggca    2460 aaaactccga cctgcagaaa tccgtgaaaa acggcgtgaa cggcaccctg gtgggcaacg    2520
gcctgtccaa aaccgaagcg accaccctga ccaaaaactt ctccgacatc cgtaaagaac    2580
tgaacgaaaa actgttcggc aactccaaca acaacaacaa cggcctgaaa aacaacaccg    2640
aaccgatcta cgcgcaggtg aacaaaaaaa agcgggcca ggcggcgtcc ccggaagaac     2700
cgatctacgc gcaggtggcg aaaaaagtgt ccgcgaaaat cgaccagctg aacgaagcga    2760
cctccgcgat caaccgtaaa atcgaccgta tcaacaaaat cgcgtccgcg ggcaaaggcg    2820
tgggcggctt ctccggcgcg ggccgttccg cgtccccgga accgatctac gcgaccatcg    2880
acttcgacga agtgaaccag gcgggcttcc cgctgcgtcg ttacgcgggc ttcgacgacc    2940
tgtccaaagt gggcctgtcc cgtgaacagg aactgacccg tcgtatcggc gacctgaacc    3000
aggcggtgtc cgaagcgaaa accggccact cgacaacct ggaacagaaa atcgacgaac     3060
tgaaagactc caccaaaaaa acgcgctga actgtgggt ggaatccgcg aaacaggtgc      3120
cgacctccct gtccgcgaaa ctggacaact acgcgaccaa ctcccacacc cgtatcaact    3180
ccaacgtgca gtccggcacc atcaacgaaa agcgaccgg catgctgacc cagaaaaacc     3240
cggaatggct gaaactggtg aacaacaaaa tcgtggcgca acgtgggc ccgcgcacc       3300 tgtccgaata cgacaaaatc ggcttcaacc agaaaaacat gaaagactac tccgactcct    3360
tcaaattctc caccaaactg aacaacgcgg tgaaagacat caaatcctcc ttcgtgcagt    3420
tcctgaccaa caccttctcc accggctcct actccctgat gaaagcgaac gcggaacacg    3480
gcgtgaaaaa caccaacacc aaaggcggct ccagaaatc ccaccaccac caccacact      3540 aacccgggg atcc                                                      3554
```

<210> SEQ ID NO 14
<211> LENGTH: 1179
<212> TYPE: PRT
<213> ORGANISM: Artificial Sequence
<220> FEATURE:
<223> OTHER INFORMATION: Synthetic

<400> SEQUENCE: 14

Met Ala Asn Glu Thr Ile Asp Gln Thr Thr Pro Asp Gln Thr Asp
1               5                   10                  15

Phe Val Pro Gln Arg Phe Ile Asn Asn Leu Gln Val Ala Phe Ile Lys
                20                  25                  30

Val Asp Asn Ala Val Ala Ser Phe Asp Pro Asp Gln Lys Pro Ile Val
            35                  40                  45

Asp Lys Asn Asp Arg Asp Asn Arg Gln Ala Phe Glu Lys Ile Ser Gln
        50                  55                  60

Leu Arg Glu Glu Tyr Ala Asn Lys Ala Ile Lys Asn Pro Ala Lys Lys
65                  70                  75                  80

```
Asn Gln Tyr Phe Ser Asp Phe Ile Asn Lys Ser Asn Asp Leu Ile Asn
                85                  90                  95

Lys Asp Asn Leu Ile Ala Val Asp Ser Ser Val Glu Ser Phe Arg Lys
            100                 105                 110

Phe Gly Asp Gln Arg Tyr Gln Ile Phe Thr Ser Trp Val Ser Leu Gln
        115                 120                 125

Lys Asp Pro Ser Lys Ile Asn Thr Gln Gln Ile Arg Asn Phe Met Glu
    130                 135                 140

Asn Val Ile Gln Pro Pro Ile Ser Asp Asp Lys Glu Lys Ala Glu Phe
145                 150                 155                 160

Leu Arg Ser Ala Lys Gln Ser Phe Ala Gly Ile Ile Gly Asn Gln
                165                 170                 175

Ile Arg Ser Asp Glu Lys Phe Met Gly Val Phe Asp Glu Ser Leu Lys
                180                 185                 190

Ala Arg Gln Glu Ala Glu Lys Asn Ala Glu Pro Ala Gly Gly Asp Trp
        195                 200                 205

Leu Asp Ile Phe Leu Ser Phe Val Phe Asn Lys Lys Gln Ser Ser Asp
    210                 215                 220

Leu Lys Glu Thr Leu Asn Gln Glu Pro Arg Pro Asp Phe Glu Gln Asn
225                 230                 235                 240

Leu Ala Thr Thr Thr Thr Asp Ile Gln Gly Leu Pro Pro Glu Ala Arg
                245                 250                 255

Asp Leu Leu Asp Glu Arg Gly Asn Phe Phe Lys Phe Thr Leu Gly Asp
                260                 265                 270

Val Glu Met Leu Asp Val Glu Gly Val Ala Asp Lys Asp Pro Asn Tyr
            275                 280                 285

Lys Phe Asn Gln Leu Leu Ile His Asn Asn Val Leu Ser Ser Val Leu
        290                 295                 300

Met Gly Gly His Ser Asn Ile Glu Pro Glu Lys Val Ser Leu Leu Tyr
305                 310                 315                 320

Gly Asp Asn Gly Gly Pro Glu Ala Arg His Asp Trp Asn Ala Thr Val
                325                 330                 335

Gly Tyr Lys Asn Gln Gln Gly Ser Asn Val Ala Thr Leu Ile Asn Ala
            340                 345                 350

His Leu Asn Asn Gly Ser Gly Leu Val Ile Ala Gly Asn Glu Asp Gly
        355                 360                 365

Ile Lys Asn Pro Ser Phe Tyr Leu Tyr Lys Glu Asp Gln Leu Thr Gly
    370                 375                 380

Leu Lys Gln Ala Leu Ser Gln Glu Glu Ile Arg Asn Lys Val Asp Phe
385                 390                 395                 400

Met Glu Phe Leu Ala Arg Asn Asn Ala Lys Leu Asp Asn Leu Ser Glu
                405                 410                 415

Lys Glu Lys Glu Lys Phe Gln Thr Glu Ile Glu Asp Phe Gln Lys Asp
            420                 425                 430

Arg Lys Ala Tyr Leu Asp Ala Leu Gly Asn Asp His Ile Ala Phe Val
        435                 440                 445

Ser Lys Lys Asp Pro Lys His Leu Ala Leu Val Thr Glu Phe Gly Asn
    450                 455                 460

Gly Glu Val Ser Tyr Thr Leu Lys Asp Tyr Gly Lys Lys Gln Asp Lys
465                 470                 475                 480

Ala Leu Asp Gly Glu Thr Lys Thr Leu Gln Gly Ser Leu Lys Tyr
                485                 490                 495
```

-continued

```
Asp Gly Val Met Phe Val Asn Tyr Ser Asn Phe Lys Tyr Thr Asn Ala
            500                 505                 510
Ser Lys Ser Pro Asn Lys Gly Val Gly Ala Thr Asn Gly Ala Ser His
        515                 520                 525
Leu Glu Ala Asn Phe Ser Lys Val Ala Val Phe Asn Leu Pro Asn Leu
    530                 535                 540
Asn Asn Leu Ala Ile Thr Asn Tyr Ile Arg Arg Asp Leu Glu Asp Lys
545                 550                 555                 560
Leu Trp Ala Lys Gly Leu Ser Pro Gln Glu Ala Asn Lys Leu Ile Lys
                565                 570                 575
Asp Phe Leu Asn Ser Asn Lys Glu Leu Val Gly Lys Ala Leu Asn Phe
            580                 585                 590
Asn Lys Ala Val Ala Glu Ala Lys Asn Thr Gly Asn Tyr Asp Glu Val
        595                 600                 605
Lys Lys Ala Gln Lys Asp Leu Glu Lys Ser Leu Arg Lys Arg Glu His
    610                 615                 620
Leu Glu Lys Glu Val Ala Lys Leu Glu Ser Arg Asn Asp Asn Lys
625                 630                 635                 640
Asn Arg Met Glu Ala Lys Ala Gln Ala Asn Ser Gln Lys Asp Lys Ile
                645                 650                 655
Phe Ala Leu Ile Asn Gln Glu Ala Ser Lys Glu Ala Arg Ala Ala Ala
            660                 665                 670
Phe Asp Pro Ser Leu Lys Asp Ile Arg Ser Glu Leu Ser Asp Lys Leu
        675                 680                 685
Glu Asn Ile Asn Lys Asn Leu Lys Asp Phe Gly Lys Ser Phe Asp Glu
    690                 695                 700
Leu Lys Asn Gly Lys Asn Asn Asp Phe Ser Lys Ala Glu Glu Thr Leu
705                 710                 715                 720
Lys Ala Leu Lys Asp Ser Val Lys Asp Leu Gly Ile Asn Pro Glu Trp
                725                 730                 735
Ile Ser Lys Ile Glu Asn Leu Asn Ala Ala Leu Asn Asp Phe Lys Asn
            740                 745                 750
Gly Lys Asn Lys Asp Phe Ser Lys Val Thr Gln Ala Lys Ser Asp Leu
        755                 760                 765
Glu Asn Ser Ile Lys Asp Val Ile Asn Gln Lys Ile Thr Asp Lys
    770                 775                 780
Val Asp Asn Leu Asn Gln Ala Val Ser Glu Thr Lys Leu Thr Gly Asp
785                 790                 795                 800
Phe Ser Lys Val Glu Gln Ala Leu Ala Glu Leu Lys Ser Leu Ser Leu
                805                 810                 815
Asp Leu Gly Lys Asn Ser Asp Leu Gln Lys Ser Val Lys Asn Gly Val
            820                 825                 830
Asn Gly Thr Leu Val Gly Asn Gly Leu Ser Lys Thr Glu Ala Thr Thr
        835                 840                 845
Leu Thr Lys Asn Phe Ser Asp Ile Arg Lys Glu Leu Asn Glu Lys Leu
    850                 855                 860
Phe Gly Asn Ser Asn Asn Asn Asn Gly Leu Lys Asn Asn Thr Glu
865                 870                 875                 880
Pro Ile Tyr Ala Gln Val Asn Lys Lys Ala Gly Gln Ala Ala Ser
                885                 890                 895
Pro Glu Glu Pro Ile Tyr Ala Gln Val Ala Lys Lys Val Ser Ala Lys
            900                 905                 910
Ile Asp Gln Leu Asn Glu Ala Thr Ser Ala Ile Asn Arg Lys Ile Asp
```

```
                915                 920                 925
Arg Ile Asn Lys Ile Ala Ser Ala Gly Lys Gly Val Gly Gly Phe Ser
    930                 935                 940
Gly Ala Gly Arg Ser Ala Ser Pro Glu Pro Ile Tyr Ala Thr Ile Asp
945                 950                 955                 960
Phe Asp Glu Val Asn Gln Ala Gly Phe Pro Leu Arg Arg Tyr Ala Gly
                965                 970                 975
Phe Asp Asp Leu Ser Lys Val Gly Leu Ser Arg Glu Gln Glu Leu Thr
            980                 985                 990
Arg Arg Ile Gly Asp Leu Asn Gln  Ala Val Ser Glu Ala  Lys Thr Gly
        995                 1000                1005
His Phe  Asp Asn Leu Glu Gln  Lys Ile Asp Glu Leu  Lys Asp Ser
    1010                1015                1020
Thr Lys  Lys Asn Ala Leu Lys  Leu Trp Val Glu Ser  Ala Lys Gln
    1025                1030                1035
Val Pro  Thr Ser Leu Ser Ala  Lys Leu Asp Asn Tyr  Ala Thr Asn
    1040                1045                1050
Ser His  Thr Arg Ile Asn Ser  Asn Val Gln Ser Gly  Thr Ile Asn
    1055                1060                1065
Glu Lys  Ala Thr Gly Met Leu  Thr Gln Lys Asn Pro  Glu Trp Leu
    1070                1075                1080
Lys Leu  Val Asn Asn Lys Ile  Val Ala His Asn Val  Gly Ser Ala
    1085                1090                1095
His Leu  Ser Glu Tyr Asp Lys  Ile Gly Phe Asn Gln  Lys Asn Met
    1100                1105                1110
Lys Asp  Tyr Ser Asp Ser Phe  Lys Phe Ser Thr Lys  Leu Asn Asn
    1115                1120                1125
Ala Val  Lys Asp Ile Lys Ser  Ser Phe Val Gln Phe  Leu Thr Asn
    1130                1135                1140
Thr Phe  Ser Thr Gly Ser Tyr  Ser Leu Met Lys Ala  Asn Ala Glu
    1145                1150                1155
His Gly  Val Lys Asn Thr Asn  Thr Lys Gly Gly Phe  Gln Lys Ser
    1160                1165                1170
His His  His His His
    1175

<210> SEQ ID NO 15
<211> LENGTH: 3798
<212> TYPE: DNA
<213> ORGANISM: Helicobacter pylori

<400> SEQUENCE: 15
ccatggatgt tcttcaccac cgtgatcatc ccggcgatcg tgggcggcat cgcgaccggc      60
gcggcggtgg gcaccgtgtc cggcctgctg tcctggggcc tgaaacaggc ggaagaagcg     120
aacaaaaccc cggacaaacc ggacaaagtg tggcgtatcc aggcgggccg tggcttcaac     180
gaattcccga caaagaata cgacctgtac cagtccctgc tgtcctccaa aatcgacggc     240
ggctgggact gggcaacgc ggcgcgtcac tactgggtga aggcggcca gtggaacaaa      300 ctggaagtgg acatgaaaga cgcggtgggc acctacaaac tgtccggcct gcgtaacttc     360
accggcggcg acctggacgt gaacatgcag aaagcgaccc tgcgtctggg ccagttcaac     420
ggcaactcct tcacctccta caagactcc gcggaccgta ccacccgtgt gaacttcaac     480
gcgaaaaaca tctccatcga aaacttcgtg gaaatcaaca accgtgtggg ctccggcgcg     540
```

-continued

```
ggccgtaaag cgtcctccac cgtgctgacc ctgcaggcgt ccgaaggcat cacctcctcc    600
aaaaacgcgg aaatctccct gtacgacggc gcgaccctga acctggcgtc caactccgtg    660
aaactgaacg gcaacgtgtg gatgggccgt ctgcagtacg tgggcgcgta cctggcgccg    720
tcctactcca ccatcaacac ctccaaagtg cagggcgaag tggacttcaa ccacctgacc    780
gtgggcgacc agaacgcggc gcaggcgggc atcatcgcgt ccaacaaaac ccacatcggc    840
accctggacc tgtggcagtc cgcgggcctg aacatcatcg cgccgccgga aggcggctac    900
aaagacaaac cgaactccac cacctcccag tccggcacca aaaacgacaa acaggaaatc    960
tcccagaaca caactccaa caccgaagtg atcaacccgc cgaacaacac ccagaaaacc    1020
gaaaccgaac cgacccaggt gatcgacggc ccgttcgcgg gcggcaaaga caccgtggtg    1080
aacatcgacc gtatcaacac caaatccgac ggcaccatcc gtgtgggcgg cttcaaagcg    1140
tccctgacca ccaacgcggc gcacctgaac atcggcaaag gcggcgtgaa cctgtccaac    1200
caggcgtccg ccgttccct gctggtggaa aacctgaccg gcaacatcac cgtggacggc    1260
ccgctgcgtg tgaacaacca ggtgggcggc tacgcgctgg cgggctcctc cgcgaacttc    1320
gaattcaaag cgggcgtgga caccaaaaac ggcaccgcga ccttcaacaa cgacatctcc    1380
ctgggccgtt tcgtgaacct gaaagtggac gcgcacaccg cgaacttcaa aggcatcgac    1440
accggcaacg gcggcttcaa caccctggac ttctccggcg tgaccgacaa agtgaacatc    1500
aacaaactga tcaccgcgtc caccaacgtg gcggtgaaaa acttcaacat caacgaactg    1560
gtggtgaaaa ccaacggcgt gtccgtgggc gaatacaccc acttctccga agacatcggc    1620
tcccagtccc gtatcaacac cgtgcgtctg gaaaccggca cccgttccat cttctccggc    1680
ggcgtgaaat tcaaagcggg cgaaaaactg gtgatcgacg aattctacta ctccccgtgg    1740
aactacttcg acgcgcgtaa catcaaaaac gtggaaatca cccgtaaatt cgcgtcctcc    1800
accccggaaa accgtggggg cacctccaaa ctgatggcgt tcaacaacct gaccctgggc    1860
cagaacgcgg tgatggacta ctcccagttc tccaacctga ccatccaggg cgacttcatc    1920
aacaaccagg gcaccatcaa ctacctggtg cgtggcggca agtggcgac cctgtccgtg    1980
ggcaacgcgc cggcgatgat gttcaacaac gacatcgact ccgcgaccgg cttctacaaa    2040
ccgctgatca aaatcaactc cgcgcaggac ctgatcaaaa acaccgaaca cgtgctgctg    2100
aaagcgaaaa tcatcggcta cggcaacgtg tccaccggca ccaactccat ctccaacgtg    2160
aacctggaag aacagttcaa agaacgtctg cgcctgtaca caacaacaa ccgtatggac    2220
acctgcgtgg tgcgtaacac cgacgacatc aaagcgtgcg gcatgcgat cggcaaccag    2280
tctgttaaca cccggacaa ctacaaatac ctgatcggca aagcgtggaa aaacatcggc    2340
atctccaaaa ccgcgaacgg ctccaaaatc tccgtgtact acctgggcaa ctccaccccg    2400
accgaaaacg gcggcaacac caccaacctg ccgaccaaca ccaccaacaa cgcgcgttcc    2460
gcgaactacg cgctggtgaa aaacgcgccg ttcgcgcact ccgcgacccc gaacctggtg    2520
gcgatcaacc agcacgactt cggcaccatc gaatccgtgt cgaactggc gaaccgttcc    2580
aaagacatcg acaccctgta caccactcc ggcgcgcagg ccgtgacct gctgcagacc    2640
ctgctgatcg actcccacga cgcgggctac gcgcgtcaga tgatcgacaa cacctccacc    2700
ggcgaaatca ccaaacagct gaacgcggcg accgacgcgc tgaacaacgt ggcgtccctg    2760
gaacacaaac agtccggcct gcagaccctg tccctgtcca acgcgatgat cctgaactcc    2820
cgtctggtga acctgtcccg taaacacacc aaccacatca actccttcgc gcagcgtctg    2880
caggcgctga aaggccagcg tttcgcgtcc ctggaatccg cggcggaagt gctgtaccag    2940
```

-continued

```
ttcgcgccga aatacgaaaa accgaccaac gtgtgggcga acgcgatcgg cggcgcgtcc    3000
ctgaactccg gcggcaacgc gtccctgtac ggcacctccg cgggcgtgga cgcgtacctg    3060
aacggcgaag tggaagcgat cgtgggcggc ttcggctcct acggctactc ctccttctcc    3120
aaccaggcga actccctgaa ctccggcgcg aacaacgcga acttcggcgt gtactcccgt    3180
ttcttcgcga accagcacga attcgacttc gaagcgcagg gcgcgctggg ctccgaccag    3240
tcctccctga acttcaaatc cgcgctgctg caggacctga accagtccta caactacctg    3300
gcgtactccg cgaccgcgcg tgcgtcctac ggctacgact cgcgttcctt ccgtaacgcg    3360
ctggtgctga accgtccgt gggcgtgggc tacaaccacc tgggctccac caacttcaaa    3420
tccaactccc agtcccaggt ggcgctgaaa aacggcgcgt cctcccagca cctgttcaac    3480
gcgaacgcga acgtggaagc gcgttactac tacggcgaca cctcctactt ctacctgcac    3540
gcgggcgtgc tgcaggaatt cgcgcacttc ggctccaacg acgtggcgtc cctgaacacc    3600
ttcaaaatca acgcggcgcg ttccccgctg tccacctacg cgcgtgcgat gatgggcggc    3660
gaactgcagc tggcgaaaga agtgttcctg aacctgggcg tggtgtacct gcacaacctg    3720
atctccaacg cgtcccactt cgcgtccaac ctgggcatgc gttactcctt ccaccaccac    3780
caccaccact aacccggg                                                  3798
```

<210> SEQ ID NO 16
<211> LENGTH: 1265
<212> TYPE: PRT
<213> ORGANISM: Artificial Sequence
<220> FEATURE:
<223> OTHER INFORMATION: Synthetic

<400> SEQUENCE: 16

```
Pro Trp Met Phe Phe Thr Thr Val Ile Ile Pro Ala Ile Val Gly Gly
1               5                   10                  15

Ile Ala Thr Gly Ala Ala Val Gly Thr Val Ser Gly Leu Leu Ser Trp
            20                  25                  30

Gly Leu Lys Gln Ala Glu Glu Ala Asn Lys Thr Pro Asp Lys Pro Asp
        35                  40                  45

Lys Val Trp Arg Ile Gln Ala Gly Arg Gly Phe Asn Glu Phe Pro Asn
    50                  55                  60

Lys Glu Tyr Asp Leu Tyr Gln Ser Leu Leu Ser Ser Lys Ile Asp Gly
65                  70                  75                  80

Gly Trp Asp Trp Gly Asn Ala Ala Arg His Tyr Trp Val Lys Gly Gly
                85                  90                  95

Gln Trp Asn Lys Leu Glu Val Asp Met Lys Asp Ala Val Gly Thr Tyr
            100                 105                 110

Lys Leu Ser Gly Leu Arg Asn Phe Thr Gly Gly Asp Leu Asp Val Asn
        115                 120                 125

Met Gln Lys Ala Thr Leu Arg Leu Gly Gln Phe Asn Gly Asn Ser Phe
    130                 135                 140

Thr Ser Tyr Lys Asp Ser Ala Asp Arg Thr Thr Arg Val Asn Phe Asn
145                 150                 155                 160

Ala Lys Asn Ile Ser Ile Glu Asn Phe Val Glu Ile Asn Asn Arg Val
                165                 170                 175

Gly Ser Gly Ala Gly Arg Lys Ala Ser Ser Thr Val Leu Thr Leu Gln
            180                 185                 190

Ala Ser Glu Gly Ile Thr Ser Ser Lys Asn Ala Glu Ile Ser Leu Tyr
        195                 200                 205
```

-continued

```
Asp Gly Ala Thr Leu Asn Leu Ala Ser Asn Ser Val Lys Leu Asn Gly
    210                 215                 220
Asn Val Trp Met Gly Arg Leu Gln Tyr Val Gly Ala Tyr Leu Ala Pro
225                 230                 235                 240
Ser Tyr Ser Thr Ile Asn Thr Ser Lys Val Gln Gly Glu Val Asp Phe
                245                 250                 255
Asn His Leu Thr Val Gly Asp Gln Asn Ala Ala Gln Ala Gly Ile Ile
                260                 265                 270
Ala Ser Asn Lys Thr His Ile Gly Thr Leu Asp Leu Trp Gln Ser Ala
        275                 280                 285
Gly Leu Asn Ile Ile Ala Pro Pro Glu Gly Gly Tyr Lys Asp Lys Pro
290                 295                 300
Asn Ser Thr Thr Ser Gln Ser Gly Thr Lys Asn Asp Lys Gln Glu Ile
305                 310                 315                 320
Ser Gln Asn Asn Asn Ser Asn Thr Glu Val Ile Asn Pro Pro Asn Asn
                325                 330                 335
Thr Gln Lys Thr Glu Thr Glu Pro Thr Gln Val Ile Asp Gly Pro Phe
                340                 345                 350
Ala Gly Gly Lys Asp Thr Val Val Asn Ile Asp Arg Ile Asn Thr Lys
                355                 360                 365
Ser Asp Gly Thr Ile Arg Val Gly Gly Phe Lys Ala Ser Leu Thr Thr
370                 375                 380
Asn Ala Ala His Leu Asn Ile Gly Lys Gly Gly Val Asn Leu Ser Asn
385                 390                 395                 400
Gln Ala Ser Gly Arg Ser Leu Leu Val Glu Asn Leu Thr Gly Asn Ile
                405                 410                 415
Thr Val Asp Gly Pro Leu Arg Val Asn Asn Gln Val Gly Gly Tyr Ala
                420                 425                 430
Leu Ala Gly Ser Ser Ala Asn Phe Glu Phe Lys Ala Gly Val Asp Thr
                435                 440                 445
Lys Asn Gly Thr Ala Thr Phe Asn Asn Asp Ile Ser Leu Gly Arg Phe
        450                 455                 460
Val Asn Leu Lys Val Asp Ala His Thr Ala Asn Phe Lys Gly Ile Asp
465                 470                 475                 480
Thr Gly Asn Gly Gly Phe Asn Thr Leu Asp Phe Ser Gly Val Thr Asp
                485                 490                 495
Lys Val Asn Ile Asn Lys Leu Ile Thr Ala Ser Thr Asn Val Ala Val
                500                 505                 510
Lys Asn Phe Asn Ile Asn Glu Leu Val Lys Thr Asn Gly Val Ser
        515                 520                 525
Val Gly Glu Tyr Thr His Phe Ser Glu Asp Ile Gly Ser Gln Ser Arg
        530                 535                 540
Ile Asn Thr Val Arg Leu Glu Thr Gly Thr Arg Ser Ile Phe Ser Gly
545                 550                 555                 560
Gly Val Lys Phe Lys Ala Gly Glu Lys Leu Val Ile Asp Glu Phe Tyr
                565                 570                 575
Tyr Ser Pro Trp Asn Tyr Phe Asp Ala Arg Asn Ile Lys Asn Val Glu
                580                 585                 590
Ile Thr Arg Lys Phe Ala Ser Ser Thr Pro Glu Asn Pro Trp Gly Thr
        595                 600                 605
Ser Lys Leu Met Ala Phe Asn Asn Leu Thr Leu Gly Gln Asn Ala Val
        610                 615                 620
```

-continued

```
Met Asp Tyr Ser Gln Phe Ser Asn Leu Thr Ile Gln Gly Asp Phe Ile
625                 630                 635                 640

Asn Asn Gln Gly Thr Ile Asn Tyr Leu Val Arg Gly Lys Val Ala
            645                 650                 655

Thr Leu Ser Val Gly Asn Ala Ala Met Met Phe Asn Asn Asp Ile
            660                 665                 670

Asp Ser Ala Thr Gly Phe Tyr Lys Pro Leu Ile Lys Ile Asn Ser Ala
            675                 680                 685

Gln Asp Leu Ile Lys Asn Thr Glu His Val Leu Leu Lys Ala Lys Ile
690                 695                 700

Ile Gly Tyr Gly Asn Val Ser Thr Gly Thr Asn Ser Ile Ser Asn Val
705                 710                 715                 720

Asn Leu Glu Glu Gln Phe Lys Glu Arg Leu Ala Leu Tyr Asn Asn Asn
            725                 730                 735

Asn Arg Met Asp Thr Cys Val Val Arg Asn Thr Asp Asp Ile Lys Ala
            740                 745                 750

Cys Gly Met Ala Ile Gly Asn Gln Ser Val Asn Pro Asp Asn Tyr
            755                 760                 765

Lys Tyr Leu Ile Gly Lys Ala Trp Lys Asn Ile Gly Ile Ser Lys Thr
770                 775                 780

Ala Asn Gly Ser Lys Ile Ser Val Tyr Tyr Leu Gly Asn Ser Thr Pro
785                 790                 795                 800

Thr Glu Asn Gly Gly Asn Thr Thr Asn Leu Pro Thr Asn Thr Thr Asn
            805                 810                 815

Asn Ala Arg Ser Ala Asn Tyr Ala Leu Val Lys Asn Ala Pro Phe Ala
            820                 825                 830

His Ser Ala Thr Pro Asn Leu Val Ala Ile Asn Gln His Asp Phe Gly
            835                 840                 845

Thr Ile Glu Ser Val Phe Glu Leu Ala Asn Arg Ser Lys Asp Ile Asp
850                 855                 860

Thr Leu Tyr Thr His Ser Gly Ala Gln Gly Arg Asp Leu Leu Gln Thr
865                 870                 875                 880

Leu Leu Ile Asp Ser His Asp Ala Gly Tyr Ala Arg Gln Met Ile Asp
            885                 890                 895

Asn Thr Ser Thr Gly Glu Ile Thr Lys Gln Leu Asn Ala Ala Thr Asp
            900                 905                 910

Ala Leu Asn Asn Val Ala Ser Leu Glu His Lys Gln Ser Gly Leu Gln
            915                 920                 925

Thr Leu Ser Leu Ser Asn Ala Met Ile Leu Asn Ser Arg Leu Val Asn
930                 935                 940

Leu Ser Arg Lys His Thr Asn His Ile Asn Ser Phe Ala Gln Arg Leu
945                 950                 955                 960

Gln Ala Leu Lys Gly Gln Arg Phe Ala Ser Leu Glu Ser Ala Ala Glu
            965                 970                 975

Val Leu Tyr Gln Phe Ala Pro Lys Tyr Glu Lys Pro Thr Asn Val Trp
            980                 985                 990

Ala Asn Ala Ile Gly Gly Ala Ser Leu Asn Ser Gly Gly Asn Ala Ser
            995                 1000                1005

Leu Tyr Gly Thr Ser Ala Gly Val Asp Ala Tyr Leu Asn Gly Glu
        1010                1015                1020

Val Glu Ala Ile Val Gly Gly Phe Gly Ser Tyr Gly Tyr Ser Ser
        1025                1030                1035

Phe Ser Asn Gln Ala Asn Ser Leu Asn Ser Gly Ala Asn Asn Ala
```

```
                1040                1045                1050
Asn Phe Gly Val Tyr Ser Arg Phe Phe Ala Asn Gln His Glu Phe
    1055                1060                1065

Asp Phe Glu Ala Gln Gly Ala Leu Gly Ser Asp Gln Ser Ser Leu
1070                1075                1080

Asn Phe Lys Ser Ala Leu Leu Gln Asp Leu Asn Gln Ser Tyr Asn
    1085                1090                1095

Tyr Leu Ala Tyr Ser Ala Thr Ala Arg Ala Ser Tyr Gly Tyr Asp
1100                1105                1110

Phe Ala Phe Phe Arg Asn Ala Leu Val Leu Lys Pro Ser Val Gly
    1115                1120                1125

Val Gly Tyr Asn His Leu Gly Ser Thr Asn Phe Lys Ser Asn Ser
1130                1135                1140

Gln Ser Gln Val Ala Leu Lys Asn Gly Ala Ser Ser Gln His Leu
    1145                1150                1155

Phe Asn Ala Asn Ala Asn Val Glu Ala Arg Tyr Tyr Tyr Gly Asp
1160                1165                1170

Thr Ser Tyr Phe Tyr Leu His Ala Gly Val Leu Gln Glu Phe Ala
    1175                1180                1185

His Phe Gly Ser Asn Asp Val Ala Ser Leu Asn Thr Phe Lys Ile
1190                1195                1200

Asn Ala Ala Arg Ser Pro Leu Ser Thr Tyr Ala Arg Ala Met Met
    1205                1210                1215

Gly Gly Glu Leu Gln Leu Ala Lys Glu Val Phe Leu Asn Leu Gly
1220                1225                1230

Val Val Tyr Leu His Asn Leu Ile Ser Asn Ala Ser His Phe Ala
    1235                1240                1245

Ser Asn Leu Gly Met Arg Tyr Ser Phe His His His His His His
1250                1255                1260

Pro Gly
    1265

<210> SEQ ID NO 17
<211> LENGTH: 2208
<212> TYPE: DNA
<213> ORGANISM: Artificial Sequence
<220> FEATURE:
<223> OTHER INFORMATION: Synthetic

<400> SEQUENCE: 17
ccatggatgg aagacgacgg cttctacacc tccgtgggct accagatcgg cgaagcggcg      60
cagatggtga ccaacaccaa aggcatccag gaactgtccg acaactacga aaaactgaac     120
aacctgctga caactactc cacccctgaac accctgatca aactgtccgc ggacccgtcc     180
gcggtgaacg cggcgcgtga aacctgggc gcgtccgcga aaacctgat cggcgacacc     240 aaaaactccc cggcgtacca ggcggtgctg ctggcgatca cgcggcggt gggcttctgg     300 aacgtggtgg gctacgtgac ccagtgcggc ggcaacgcga acggccagac ctccacctcc     360
tccaccacca tcttcaacaa cgaaccgggc taccgttcca cctccatcac ctgctccctg     420
aacggctaca ctcctggtta ctacggcccg atgtccatcg aaaacttcaa aaaactgaac     480
gaagcgtacc agatcctgca gaccgcgctg aaacagggcc tgccggcgct gaaagaaaac     540
aacggcaccg tgtccgtgac ctacacctac acctgctccg gcaaaggcaa cgacaactgc     600
tccccgcaga ccaccggcgt gaaccagcag aacgacggca ccaaaaccga aacccagacc     660
```

```
atcgacggca aacaggtgaa caccaccatc tcctccaaag tggtggactc caaagcgtcc    720
ggcaacacct cccacgtgtc ctacaccgaa atcaccaaca aactggaagg cgtgccggac    780
aacgcgcagt tcctgctggc gcaggcgtcc accctgatca acaccatcaa caccgcgtgc    840
ccgttcttcc acgcgaacaa ctcctccgaa gcgaacgcgc cgaaattctc caccaccacc    900
ggcaaaatct gcggcgcgtt ctccgaagaa atctccgcga tccagaaaat gatcaccgac    960
gcgcaggacc tggtgaacca gacctccgtg atcaacgaac acgaacagtc caccccggtg   1020
ggcaacaaca acggcaaacc gttcaacccg ttcaccgacg cgtccttcgc cagggcatg    1080
ctggcgaacg cgtccgcgca ggcgaaaatg ctgaacctgg cgcaccaggt gggccagacc   1140
ctgaacccgg aaaacctgac cggcaccttc aaaaacttcg tgaccgactt cctggcgacc   1200
tgcaacaaca atccaccgc gggcaccggc ggcacccagg ctccccgcc gggcaccgtg     1260
accacccaga ccttcgcgtc cggctgcgcg tacgtggaac agaccatcac caacctggaa   1320
aactccatcg cgcacttcgg cacccaggaa cagcagatcc agcaggcgga aaacatcgcg   1380
gacaccctgg tgaacttcaa atcccgttac tccgaactgg caacaccta caactccatc    1440
accaccgcgc tgtccaaagt gccgaacgcg cagtccctgc agaacgtggt gtccaaaaaa   1500
aacaacccgt actccccgca gggcatcgaa accaactact acctgaacca gaactcctac   1560
aaccagatcc agaccatcaa ccaggaactg gccgtaacc cgttccgtaa agtgggcatc    1620
gtgtcctccc agaccaacaa cggcgcgatg aacggcatcg catccaggt gggctacaaa    1680
cagttcttcg ccagaaacg taatggggc gcgcgttact acggcttctt cgactacaac     1740
cacgcgttca tcaaatcctc cttcttcaac tccgcgtccg acgtgtggac ctacggcttc   1800
ggcgcggacg cgctgtacaa cttcatcaac gacaaagcga ccaacttcct gggcaaaaac   1860
aacaaactgt ccgtgggcct gttcggcggc atcgcgctgg cgggcacctc ctggctgaac   1920
tccgaatacg tgaacctggc gaccgtgaac aacgtgtaca cgcgaaaat gaacgtggcg    1980
aacttccagt cctgttcaa catgggcgtg cgtatgaacc tggcgcgttc caaaaaaaaa   2040
ggctccgacc acgtggcgca gcacggcatc gaactgggcc tgaaaatccc gaccatcaac   2100
accaactact actccttcat gggcgcggaa ctgaaatacc gtcgtctgta ctccgtgtac   2160
ctgaactacg tgttcgcgta ccaccaccac caccaccact aacccggg               2208
```

<210> SEQ ID NO 18
<211> LENGTH: 735
<212> TYPE: PRT
<213> ORGANISM: Artificial Sequence
<220> FEATURE:
<223> OTHER INFORMATION: Synthetic

<400> SEQUENCE: 18

Pro Trp Met Glu Asp Asp Gly Phe Tyr Thr Ser Val Gly Tyr Gln Ile
1               5                   10                  15

Gly Glu Ala Ala Gln Met Val Thr Asn Thr Lys Gly Ile Gln Glu Leu
            20                  25                  30

Ser Asp Asn Tyr Glu Lys Leu Asn Asn Leu Asn Asn Tyr Ser Thr
        35                  40                  45

Leu Asn Thr Leu Ile Lys Leu Ser Ala Asp Pro Ser Ala Val Asn Ala
    50                  55                  60

Ala Arg Glu Asn Leu Gly Ala Ser Ala Lys Asn Leu Ile Gly Asp Thr
65                  70                  75                  80

Lys Asn Ser Pro Ala Tyr Gln Ala Val Leu Leu Ala Ile Asn Ala Ala
                85                  90                  95

```
Val Gly Phe Trp Asn Val Val Gly Tyr Val Thr Gln Cys Gly Gly Asn
            100                 105                 110

Ala Asn Gly Gln Thr Ser Thr Ser Thr Thr Ile Phe Asn Asn Glu
            115                 120                 125

Pro Gly Tyr Arg Ser Thr Ser Ile Thr Cys Ser Leu Asn Gly Tyr Thr
            130                 135                 140

Pro Gly Tyr Tyr Gly Pro Met Ser Ile Glu Asn Phe Lys Lys Leu Asn
145                 150                 155                 160

Glu Ala Tyr Gln Ile Leu Gln Thr Ala Leu Lys Gln Gly Leu Pro Ala
                    165                 170                 175

Leu Lys Glu Asn Asn Gly Thr Val Ser Val Thr Tyr Thr Tyr Thr Cys
                    180                 185                 190

Ser Gly Lys Gly Asn Asp Asn Cys Ser Pro Gln Thr Thr Gly Val Asn
            195                 200                 205

Gln Gln Asn Asp Gly Thr Lys Thr Glu Thr Gln Thr Ile Asp Gly Lys
            210                 215                 220

Gln Val Asn Thr Thr Ile Ser Ser Lys Val Val Asp Ser Lys Ala Ser
225                 230                 235                 240

Gly Asn Thr Ser His Val Ser Tyr Thr Glu Ile Thr Asn Lys Leu Glu
                    245                 250                 255

Gly Val Pro Asp Asn Ala Gln Phe Leu Leu Ala Gln Ala Ser Thr Leu
            260                 265                 270

Ile Asn Thr Ile Asn Thr Ala Cys Pro Phe Phe His Ala Asn Asn Ser
            275                 280                 285

Ser Glu Ala Asn Ala Pro Lys Phe Ser Thr Thr Thr Gly Lys Ile Cys
            290                 295                 300

Gly Ala Phe Ser Glu Glu Ile Ser Ala Ile Gln Lys Met Ile Thr Asp
305                 310                 315                 320

Ala Gln Asp Leu Val Asn Gln Thr Ser Val Ile Asn Glu His Glu Gln
                    325                 330                 335

Ser Thr Pro Val Gly Asn Asn Asn Gly Lys Pro Phe Asn Pro Phe Thr
            340                 345                 350

Asp Ala Ser Phe Ala Gln Gly Met Leu Ala Asn Ala Ser Ala Gln Ala
            355                 360                 365

Lys Met Leu Asn Leu Ala His Gln Val Gly Gln Thr Leu Asn Pro Glu
            370                 375                 380

Asn Leu Thr Gly Thr Phe Lys Asn Phe Val Thr Asp Phe Leu Ala Thr
385                 390                 395                 400

Cys Asn Asn Lys Ser Thr Ala Gly Thr Gly Thr Gln Gly Ser Pro
                    405                 410                 415

Pro Gly Thr Val Thr Thr Gln Thr Phe Ala Ser Gly Cys Ala Tyr Val
            420                 425                 430

Glu Gln Thr Ile Thr Asn Leu Glu Asn Ser Ile Ala His Phe Gly Thr
            435                 440                 445

Gln Glu Gln Gln Ile Gln Gln Ala Glu Asn Ile Ala Asp Thr Leu Val
            450                 455                 460

Asn Phe Lys Ser Arg Tyr Ser Glu Leu Gly Asn Thr Tyr Asn Ser Ile
465                 470                 475                 480

Thr Thr Ala Leu Ser Lys Val Pro Asn Ala Gln Ser Leu Gln Asn Val
                    485                 490                 495

Val Ser Lys Lys Asn Asn Pro Tyr Ser Pro Gln Gly Ile Glu Thr Asn
            500                 505                 510
```

Tyr Tyr Leu Asn Gln Asn Ser Tyr Asn Gln Ile Gln Thr Ile Asn Gln
            515                 520                 525

Glu Leu Gly Arg Asn Pro Phe Arg Lys Val Gly Ile Val Ser Ser Gln
        530                 535                 540

Thr Asn Asn Gly Ala Met Asn Gly Ile Gly Ile Gln Val Gly Tyr Lys
545                 550                 555                 560

Gln Phe Phe Gly Gln Lys Arg Lys Trp Gly Ala Arg Tyr Tyr Gly Phe
                565                 570                 575

Phe Asp Tyr Asn His Ala Phe Ile Lys Ser Ser Phe Asn Ser Ala
            580                 585                 590

Ser Asp Val Trp Thr Tyr Gly Phe Gly Ala Asp Ala Leu Tyr Asn Phe
        595                 600                 605

Ile Asn Asp Lys Ala Thr Asn Phe Leu Gly Lys Asn Asn Lys Leu Ser
        610                 615                 620

Val Gly Leu Phe Gly Gly Ile Ala Leu Ala Gly Thr Ser Trp Leu Asn
625                 630                 635                 640

Ser Glu Tyr Val Asn Leu Ala Thr Val Asn Asn Val Tyr Asn Ala Lys
                645                 650                 655

Met Asn Val Ala Asn Phe Gln Phe Leu Phe Asn Met Gly Val Arg Met
            660                 665                 670

Asn Leu Ala Arg Ser Lys Lys Lys Gly Ser Asp His Val Ala Gln His
        675                 680                 685

Gly Ile Glu Leu Gly Leu Lys Ile Pro Thr Ile Asn Thr Asn Tyr Tyr
        690                 695                 700

Ser Phe Met Gly Ala Glu Leu Lys Tyr Arg Arg Leu Tyr Ser Val Tyr
705                 710                 715                 720

Leu Asn Tyr Val Phe Ala Tyr His His His His His Pro Gly
                725                 730                 735

<210> SEQ ID NO 19
<211> LENGTH: 465
<212> TYPE: DNA
<213> ORGANISM: Helicobacter pylori

<400> SEQUENCE: 19
ccatggatga aaaccttcga atcctgaaaa cacctgcagg cggacgcgat cgtgctgttc      60
atgaaagtgc acaacttcca ctggaacgtg aaaggcaccg acttcttcaa cgtgcacaaa     120
gcgaccgaag aaatctacga aggcttcgcg acatgttcg acgacctggc ggaacgtatc      180
gtgcagctgg ccaccacccc gctggtgacc ctgtccgaag cgctgaaact gacccgtgtg     240
aaagaagaaa ccaaaaccct cttccactcc aaagacatct tcaaagaaat cctggaagac     300
tacaaacacc tggaaaaaga attcaaagaa ctgtccaaca ccgcggaaaa agaaggcgac     360
aaagtgaccg tgacctacgc ggacgaccag ctggcgaaac tgcagaaatc catctggatg     420
ctgcaggcgc acctggcgca ccaccaccac caccactaac ccggg                    465

<210> SEQ ID NO 20
<211> LENGTH: 154
<212> TYPE: PRT
<213> ORGANISM: Artificial Sequence
<220> FEATURE:
<223> OTHER INFORMATION: Synthetic

<400> SEQUENCE: 20

Pro Trp Met Lys Thr Phe Glu Ile Leu Lys His Leu Gln Ala Asp Ala
1               5                   10                  15

Ile Val Leu Phe Met Lys Val His Asn Phe His Trp Asn Val Lys Gly
             20                  25                  30

Thr Asp Phe Phe Asn Val His Lys Ala Thr Glu Glu Ile Tyr Glu Gly
         35                  40                  45

Phe Ala Asp Met Phe Asp Asp Leu Ala Glu Arg Ile Val Gln Leu Gly
     50                  55                  60

His His Pro Leu Val Thr Leu Ser Glu Ala Leu Lys Leu Thr Arg Val
 65                  70                  75                  80

Lys Glu Glu Thr Lys Thr Ser Phe His Ser Lys Asp Ile Phe Lys Glu
                 85                  90                  95

Ile Leu Glu Asp Tyr Lys His Leu Glu Lys Glu Phe Lys Glu Leu Ser
             100                 105                 110

Asn Thr Ala Glu Lys Glu Gly Asp Lys Val Thr Val Thr Tyr Ala Asp
         115                 120                 125

Asp Gln Leu Ala Lys Leu Gln Lys Ser Ile Trp Met Leu Gln Ala His
     130                 135                 140

Leu Ala His His His His His His Pro Gly
145                 150

<210> SEQ ID NO 21
<211> LENGTH: 2523
<212> TYPE: DNA
<213> ORGANISM: Artificial Sequence
<220> FEATURE:
<223> OTHER INFORMATION: Synthetic

<400> SEQUENCE: 21

```
ccatggatgg cgatcggctc cctgtcctcc ctgggcctgg gctccaaagt gctgaactac      60
gacgtgatcg acaaactgaa agacgcggac gaaaaagcgc tgatcgcgcc gctggacaaa     120
aaaatggaac agaacgtgga aaaacagaaa gcgctggtgg aaatcaaaac cctgctgtcc     180
gcgctgaaag cccggtgaa acccctgtcc gactactcca cctacatctc ccgtaaatcc     240
aacgtgaccg cgacgcgct gtccgcgtcc gtgggcgcgg cgtgccgat ccaggacatc      300
aaagtgacg tgcagaacct ggcgcagggc gacatcaacg aactgggcgc gaaattctcc     360
tcccgtgacg acatcttctc ccaggtggac accaccctga attctacac ccagaacaaa     420
gactacgcgg tgaacatcaa agcgggcatg accctgggcg acgtggcgca gtccatcacc     480
gacgcgacca acggcgaagt gatgggcatc gtgatgaaaa ccggcggcaa cgacccgtac     540
cagctgatgg tgaacaccaa aaacaccggc gaagacaacc gtatctactt cggctcccac     600
ctgcagtcca ccctgaccaa caaaacgcg ctgtccctgg gcgtggacgg ctccggcaaa     660
tccgaagtgt ccctgaacct gaaggcgcg gacggcaaca tgcacgaagt gccgatcatg     720
ctggaactgc cggaatccgc gtccatcaaa cagaaaaaca ccgcgatcca aagagcgatg    780
gaacaggcgc tggaaaacga cccgaacttc aaagacctga tcgcgaaccg tgacatctcc    840
atcgacaccc tgcacggcgg cgactccctg atcatcaacg accgtcgtgg cggcaacatc    900
gaaatcaaag ctccaaagc gaaagaactg ggcttcctgc agaccaccac ccaggaatcc    960
gacctgctga atcctcccg taccatcaaa gaaggcaaac tggaaggcgt gatctccctg   1020
aacgccaga aactggacct gaaagcgctg accaagaag gcaacacctc gaagaaaac    1080
accgacgcga tcgtgcaggc gatcaacgcg aaagaaggcc tgaacgcgtt caaaaacgcg   1140
gaaggcaaac tggtgatcaa ctccaaaacc ggcatgctga ccatcaaagg cgaagacgcg   1200
ctgggcaaag cgtccctgaa agacctgggc ctgtccgcgg cacatgca gtcctacgaa  1260
```

```
gcgtcccaga acaccctgtt catgtccaaa aacctgcaga aagcgtccga ctccgaattc    1320
acctacaacg gcgtgtccat cacccgtccg accaacgaaa tcaacgacgt gatctccggc    1380
gtgaacatca ccctggaaca gaccaccgaa ccgaacaaac cggcgatcat ctccgtgaac    1440
cgtgacaacc aggcgatcat cgactccctg accgaattcg tgaaagcgta caacgaactg    1500
atcccgaaac tggacgaaga cacccgttac gacgcggaca ccaaaatcgc gggcatcttc    1560
aacggcgtgg cgacatccg taccatccgt tcctccctga caacgtgtt ctcctactcc    1620
gtgcacaccg acaacggcgt ggaatccctg atgaaatacg cctgtccct ggacgacaaa    1680
ggcgtgatgt ccctggacga agcgaaactg tcctccgcgc tgaactccaa cccgaaagcg    1740
acccaggact tcttctacgg ctccgactcc aaagacatgg gcggccgtga atccaccag    1800
gaaggcggcg gcgcggcgctc cggcggcggc ggctccgacg tgcagttcgc ggactcccgt    1860
atccgtccgc agaccatcgc ggcggaagac accctgcacg acatgggcat cttctccatc    1920
acctcctccg actcccaggc gatgggccgt gtgggcgaag tgatcacccg tacctggcag    1980
accgcggaca aaaacaaaaa agaattcggc ggcggcggc gctcctacaa cctggtgggc    2040
gtgcagggcg cgtcctacga caacatctcc gcgtccaaca ccaacctgca ggaccagttc    2100
aaagaacgtc tggcgctgta caacaacaac aaccgtatgg acatctgcgt ggtgcgtaaa    2160
aacaacaccg acgacatcaa agcgtgcggc atggcgatcg caaccagtc cggcggcggc    2220
ggctccgaac cggtgccgca cgtgcagccg gacatcgcga ccaccaccac ccacatccag    2280
ggcctgccgc cggaatcccg tgacctgctg gacgaacgtg caacttctc caaattcacc    2340
ctgggcgaca tggaaatgct ggacgtgaa ggcgtggcgg acatcgaccc gaactacaaa    2400
ttcaaccagc tgctgatcca caacaacgcg ctgtcctccg tgctgatggg ctcccacaac    2460
ggcatcgaac cggaaaaagt gtccctgctg ttcgcgcacc accaccacca ccactaaccc    2520
ggg                                                                  2523
```

<210> SEQ ID NO 22
<211> LENGTH: 840
<212> TYPE: PRT
<213> ORGANISM: Artificial Sequence
<220> FEATURE:
<223> OTHER INFORMATION: Synthetic

<400> SEQUENCE: 22

```
Pro Trp Met Ala Ile Gly Ser Leu Ser Ser Leu Gly Leu Gly Ser Lys
1               5                   10                  15

Val Leu Asn Tyr Asp Val Ile Asp Lys Leu Lys Asp Ala Asp Glu Lys
            20                  25                  30

Ala Leu Ile Ala Pro Leu Asp Lys Lys Met Glu Gln Asn Val Glu Lys
        35                  40                  45

Gln Lys Ala Leu Val Glu Ile Lys Thr Leu Leu Ser Ala Leu Lys Gly
    50                  55                  60

Pro Val Lys Thr Leu Ser Asp Tyr Ser Thr Tyr Ile Ser Arg Lys Ser
65                  70                  75                  80

Asn Val Thr Gly Asp Ala Leu Ser Ala Ser Val Gly Ala Gly Val Pro
                85                  90                  95

Ile Gln Asp Ile Lys Val Asp Val Gln Asn Leu Ala Gln Gly Asp Ile
            100                 105                 110

Asn Glu Leu Gly Ala Lys Phe Ser Ser Arg Asp Asp Ile Phe Ser Gln
        115                 120                 125

Val Asp Thr Thr Leu Lys Phe Tyr Thr Gln Asn Lys Asp Tyr Ala Val
```

```
              130                 135                 140
Asn Ile Lys Ala Gly Met Thr Leu Gly Asp Val Ala Gln Ser Ile Thr
145                 150                 155                 160
Asp Ala Thr Asn Gly Glu Val Met Gly Ile Val Met Lys Thr Gly Gly
                165                 170                 175
Asn Asp Pro Tyr Gln Leu Met Val Asn Thr Lys Asn Thr Gly Glu Asp
                180                 185                 190
Asn Arg Ile Tyr Phe Gly Ser His Leu Gln Ser Thr Leu Thr Asn Lys
                195                 200                 205
Asn Ala Leu Ser Leu Gly Val Asp Gly Ser Gly Lys Ser Glu Val Ser
                210                 215                 220
Leu Asn Leu Lys Gly Ala Asp Gly Asn Met His Glu Val Pro Ile Met
225                 230                 235                 240
Leu Glu Leu Pro Glu Ser Ala Ser Ile Lys Gln Lys Asn Thr Ala Ile
                245                 250                 255
Gln Lys Ala Met Glu Gln Ala Leu Glu Asn Asp Pro Asn Phe Lys Asp
                260                 265                 270
Leu Ile Ala Asn Arg Asp Ile Ser Ile Asp Thr Leu His Gly Gly Asp
                275                 280                 285
Ser Leu Ile Ile Asn Asp Arg Arg Gly Gly Asn Ile Glu Ile Lys Gly
                290                 295                 300
Ser Lys Ala Lys Glu Leu Gly Phe Leu Gln Thr Thr Thr Gln Glu Ser
305                 310                 315                 320
Asp Leu Leu Lys Ser Ser Arg Thr Ile Lys Glu Gly Lys Leu Glu Gly
                325                 330                 335
Val Ile Ser Leu Asn Gly Gln Lys Leu Asp Leu Lys Ala Leu Thr Lys
                340                 345                 350
Glu Gly Asn Thr Ser Glu Glu Asn Thr Asp Ala Ile Val Gln Ala Ile
                355                 360                 365
Asn Ala Lys Glu Gly Leu Asn Ala Phe Lys Asn Ala Glu Gly Lys Leu
                370                 375                 380
Val Ile Asn Ser Lys Thr Gly Met Leu Thr Ile Lys Gly Glu Asp Ala
385                 390                 395                 400
Leu Gly Lys Ala Ser Leu Lys Asp Leu Gly Leu Ser Ala Gly Ile Met
                405                 410                 415
Gln Ser Tyr Glu Ala Ser Gln Asn Thr Leu Phe Met Ser Lys Asn Leu
                420                 425                 430
Gln Lys Ala Ser Asp Ser Glu Phe Thr Tyr Asn Gly Val Ser Ile Thr
                435                 440                 445
Arg Pro Thr Asn Glu Ile Asn Asp Val Ile Ser Gly Val Asn Ile Thr
                450                 455                 460
Leu Glu Gln Thr Thr Glu Pro Asn Lys Pro Ala Ile Ile Ser Val Asn
465                 470                 475                 480
Arg Asp Asn Gln Ala Ile Ile Asp Ser Leu Thr Glu Phe Val Lys Ala
                485                 490                 495
Tyr Asn Glu Leu Ile Pro Lys Leu Asp Glu Asp Thr Arg Tyr Asp Ala
                500                 505                 510
Asp Thr Lys Ile Ala Gly Ile Phe Asn Gly Val Gly Asp Ile Arg Thr
                515                 520                 525
Ile Arg Ser Ser Leu Asn Asn Val Phe Ser Tyr Ser Val His Thr Asp
                530                 535                 540
Asn Gly Val Glu Ser Leu Met Lys Tyr Gly Leu Ser Leu Asp Asp Lys
545                 550                 555                 560
```

```
Gly Val Met Ser Leu Asp Glu Ala Lys Leu Ser Ser Ala Leu Asn Ser
            565                 570                 575

Asn Pro Lys Ala Thr Gln Asp Phe Phe Tyr Gly Ser Asp Ser Lys Asp
            580                 585                 590

Met Gly Gly Arg Glu Ile His Gln Glu Gly Gly Gly Gly Ser Gly
            595                 600                 605

Gly Gly Gly Ser Asp Val Gln Phe Ala Asp Ser Arg Ile Arg Pro Gln
            610                 615                 620

Thr Ile Ala Ala Glu Asp Thr Leu His Asp Met Gly Ile Phe Ser Ile
625                 630                 635                 640

Thr Ser Ser Asp Ser Gln Ala Met Gly Arg Val Gly Glu Val Ile Thr
            645                 650                 655

Arg Thr Trp Gln Thr Ala Asp Lys Asn Lys Lys Glu Phe Gly Gly Gly
            660                 665                 670

Gly Gly Ser Tyr Asn Leu Val Gly Val Gln Gly Ala Ser Tyr Asp Asn
            675                 680                 685

Ile Ser Ala Ser Asn Thr Asn Leu Gln Asp Gln Phe Lys Glu Arg Leu
            690                 695                 700

Ala Leu Tyr Asn Asn Asn Arg Met Asp Ile Cys Val Val Arg Lys
705                 710                 715                 720

Asn Asn Thr Asp Asp Ile Lys Ala Cys Gly Met Ala Ile Gly Asn Gln
            725                 730                 735

Ser Gly Gly Gly Gly Ser Glu Pro Val Pro His Val Gln Pro Asp Ile
            740                 745                 750

Ala Thr Thr Thr Thr His Ile Gln Gly Leu Pro Pro Glu Ser Arg Asp
            755                 760                 765

Leu Leu Asp Glu Arg Gly Asn Phe Ser Lys Phe Thr Leu Gly Asp Met
770                 775                 780

Glu Met Leu Asp Val Glu Gly Val Ala Asp Ile Asp Pro Asn Tyr Lys
785                 790                 795                 800

Phe Asn Gln Leu Leu Ile His Asn Asn Ala Leu Ser Ser Val Leu Met
            805                 810                 815

Gly Ser His Asn Gly Ile Glu Pro Glu Lys Val Ser Leu Leu Phe Ala
            820                 825                 830

His His His His His His Pro Gly
            835                 840

<210> SEQ ID NO 23
<211> LENGTH: 1701
<212> TYPE: DNA
<213> ORGANISM: Helicobacter pylori

<400> SEQUENCE: 23
atgaaaaaga ttagcagaaa agaatatgtt tctatgtatg gccctactac aggcgataaa      60
gtgagattgg gcgatacaga cttgatcgct gaagtagaac atgactacac catttatggc     120
gaagagctta aattcggtgg cggtaaaacc ctgagagaag gcatgagcca atccaacaac     180
cctagcaaag aagaattgga tctaatcatc actaacgctt taatcgtgga ttacaccggt     240
atttataaag cggatattgg tattaaagat ggcaaaatcg ctggcattgg taaaggcggt     300
aacaaagaca tgcaagatgg cgttaaaaac aatcttagcg taggtcctgc tactgaagcc     360
ttagccggtg aaggtttgat cgtaactgct ggtggtattg acacacacat ccacttcatt     420
tcaccccaac aaatccctac agcttttgca agcggtgtaa caaccatgat tggtggcgga     480
```

```
actggtcctg ctgatggcac taatgcgact actatcactc caggcagaag aaatttaaaa      540
ctgcgtgcgg cagaagaata ttccatgaac ctgggcttag gtttcaaagg taacgcttct      600
aacgacgcga gcttagccga tcaaatcgaa gctggtgcga ttggctttaa aatccacgaa      660
gactggggca ccactccttc tgcaatcaat catgcgttag atgttgcaga caaatacgat      720
gtgcaagtcg ctatccacac agacactttg aatgaagccg gttgcgtgga agacactgca      780
gctattgccg gacgcactat gcacactttc cacactgaag gtgctggcgg cggacacgct      840
cctgatatta ttaaagtagc tggtgaacac aacattcttc ccgcttccac taaccccact      900
atccctttca ctgtgaatac agaagcagaa cacatggaca tgcttatggt gtgccaccac      960
ttggataaaa gcattaaaga agatgttcag ttcgctgatt caaggatccg ccctcaaacc     1020
attgcggctg aagacacttt tgcatgacatg gggattttct caatcaccag ctctgactct     1080
caagctatgg gtcgtgtggg tgaagttatc actagaactt ggcaaacagc tgacaaaaac     1140
aaaaaagaat ttggccgctt gaaagaagaa aaggcgata acgacaactt caggatcaaa     1200
cgctacttgt ctaaatacac cattaaccca gcgatcgctc atgggattag cgagtatgta     1260
ggttctgtag aagtgggcaa agtggctgac ttggtattgt ggagtcccgc attctttggc     1320
gtaaaaccca acatgatcat caaaggcggg ttcattgcgt tgagtcaaat gggtgacgcg     1380
aacgcttcta tccctacccc acaaccagtt tattacagag aaatgttcgc tcatcatggt     1440
aaagccaaat acgatgcaaa catcactttt gtgtctcaag cggcttatga caaaggcatt     1500
aaagaagaat tagggcttga agacaagtg ttgccggtaa aaattgcag aaacatcact     1560 aaaaagaca tgcaattcaa cgacactacc gctcacattg aagtcaatcc tgaaacttac     1620
catgtgttcg tggatggcaa agaagtaact tctaaaccag ccaataaagt gagcttggcg     1680
caactcttta gcatttcta g                                              1701

<210> SEQ ID NO 24
<211> LENGTH: 1733
<212> TYPE: DNA
<213> ORGANISM: Artificial Sequence
<220> FEATURE:
<223> OTHER INFORMATION: Synthetic

<400> SEQUENCE: 24
ccatggagaa gatctcccgt aaagaatacg tgtccatgta cggcccgacc accggcgaca       60
aagtgcgtct gggcgacacc gacctgatcg cggaagtgga acacgactac accatctacg      120
gcgaagaact gaaattcggc ggcggcaaaa ccctgcgtga aggcatgtcc cagtccaaca      180
acccgtccaa agaagaactg gacctgatca tcaccaacgc gctgatcgtg gactacaccg      240
gcatctacaa agcggacatc ggcatcaaag acggcaaaat cgcgggcatc ggcaaaggcg      300
gcaacaaaga catgcaggac ggcgtgaaaa caacctgtc cgtgggcccg cgaccgaag      360 cgctggcggg cgaaggcctg atcgtgaccg cgggcggcat cgacacccac atccacttca      420
tctccccgca gcagatcccg accgcgttcg cgtccggcgt gaccaccatg atcggcggcg      480
gcaccggccc ggcggacggc accaacgcga ccaccatcac tcctggtcgt cgtaacctga      540
agctgcgtgc ggcggaagaa tactccatga acctgggctt cctggcgaaa ggcaacgcgt      600
ccaacgacgc gtccctggcg gaccagatcg aagcgggcgc gatcggcttc aaaatccacg      660
aagactgggg caccaccccg tccgcgatca accacgcgct ggacgtggcg acaaatacg      720 acgtgcaggt ggcgatccac accgacaccc tgaacgaagc gggctgcgtg aagacactg      780 ctgcgatcgc gggccgtacc atgcacacct tccacaccga aggcgcgggc ggcggccacg      840
```

```
cgccggacat catcaaagtg gcgggcgaac acaacatcct gccggcgtcc accaacccga    900
ccatcccgtt caccgtgaac accgaagcgg aacacatgga catgctgatg gtgtgccacc    960
acctggacaa atccatcaaa gaagacgtgc agttcgcgga ctcccgtatc cgtccgcaga   1020
ccatcgcggc ggaagacacc ctgcacgaca tgggcatctt ctccatcacc tcctccgact   1080
cccaggcgat gggccgtgtg ggcgaagtga tcacccgtac ctggcagacc gcggacaaaa   1140
acaagaagga attcggccgt ctgaaagaag aaaaaggcga caacgacaac ttccgtatca   1200
aacgttacct gtccaaatac accatcaacc ggcgatcgc gcacggcatc tccgaatacg   1260
tgggctccgt ggaagtgggc aaagtggcgg acctggtgct gtggtccccg gcgttcttcg   1320
gcgtgaaacc gaacatgatc atcaaggcg gcttcatcgc gctgtcccag atgggcgacg   1380
cgaacgcgtc catcccgacc ccgcagccgg tgtactaccg tgaaatgttc gcgcaccacg   1440
gcaaagcgaa atacgacgcg aacatcacct tcgtgtccca ggcggcgtac gacaaaggca   1500
tcaaagaaga actgggcctg aacgtcagg tgctgccggt gaaaaactgc cgtaacatca   1560
ccaagaagga catgcagttc aacgacacca ccgcgcacat cgaagtgaac ccggaaacct   1620
accacgtgtt cgtggacggc aaagaagtga cctccaaacc ggcgaacaaa gtgtccctgg   1680
cgcagctgtt ctccatcttc caccaccacc accaccacta acccggggga tcc          1733
```

<210> SEQ ID NO 25
<211> LENGTH: 572
<212> TYPE: PRT
<213> ORGANISM: Artificial Sequence
<220> FEATURE:
<223> OTHER INFORMATION: Synthetic

<400> SEQUENCE: 25

```
Met Glu Lys Ile Ser Arg Lys Glu Tyr Val Ser Met Tyr Gly Pro Thr
1               5                   10                  15

Thr Gly Asp Lys Val Arg Leu Gly Asp Thr Asp Leu Ile Ala Glu Val
            20                  25                  30

Glu His Asp Tyr Thr Ile Tyr Gly Glu Glu Leu Lys Phe Gly Gly Gly
        35                  40                  45

Lys Thr Leu Arg Glu Gly Met Ser Gln Ser Asn Asn Pro Ser Lys Glu
    50                  55                  60

Glu Leu Asp Leu Ile Ile Thr Asn Ala Leu Ile Val Asp Tyr Thr Gly
65                  70                  75                  80

Ile Tyr Lys Ala Glu Glu Leu Asp Leu Ile Ile Thr Asn Ala Leu Ile
                85                  90                  95

Val Asp Tyr Thr Gly Ile Tyr Lys Ala Asp Gly Val Lys Asn Asn Leu
            100                 105                 110

Ser Val Gly Pro Ala Thr Glu Ala Leu Ala Gly Glu Gly Leu Ile Val
        115                 120                 125

Thr Ala Gly Gly Ile Asp Thr His Ile His Phe Ile Ser Pro Gln Gln
    130                 135                 140

Ile Pro Thr Ala Phe Ala Ser Gly Val Thr Thr Met Ile Gly Gly Gly
145                 150                 155                 160

Thr Gly Pro Ala Asp Gly Thr Asn Ala Thr Thr Ile Thr Pro Gly Arg
                165                 170                 175

Arg Asn Leu Lys Leu Arg Ala Ala Glu Glu Tyr Ser Met Asn Leu Gly
            180                 185                 190

Phe Leu Ala Lys Gly Asn Ala Ser Asn Asp Ala Ser Leu Ala Asp Gln
        195                 200                 205
```

Ile Glu Ala Gly Ala Ile Gly Phe Lys Ile His Glu Asp Trp Gly Thr
210                 215                 220

Thr Pro Ser Ala Ile Asn His Ala Leu Asp Val Ala Asp Lys Tyr Asp
225                 230                 235                 240

Val Gln Val Ala Ile His Thr Asp Thr Leu Asn Glu Ala Gly Cys Val
            245                 250                 255

Glu Asp Thr Ala Ala Ile Ala Gly Arg Thr Met His Thr Phe His Thr
            260                 265                 270

Glu Gly Ala Gly Gly His Ala Pro Asp Ile Ile Lys Val Ala Gly
        275                 280                 285

Glu His Asn Ile Leu Pro Ala Ser Thr Asn Pro Thr Ile Pro Phe Thr
290                 295                 300

Val Asn Thr Glu Ala Glu His Met Asp Met Leu Met Val Cys His His
305                 310                 315                 320

Leu Asp Lys Ser Ile Lys Glu Asp Val Gln Phe Ala Asp Ser Arg Ile
            325                 330                 335

Arg Pro Gln Thr Ile Ala Ala Glu Asp Thr Leu His Asp Met Gly Ile
            340                 345                 350

Phe Ser Ile Thr Ser Ser Asp Ser Gln Ala Met Gly Arg Val Gly Glu
        355                 360                 365

Val Ile Thr Arg Thr Trp Gln Thr Ala Asp Lys Asn Lys Lys Glu Phe
370                 375                 380

Gly Arg Leu Lys Glu Glu Lys Gly Asp Asn Asp Asn Phe Arg Ile Lys
385                 390                 395                 400

Arg Tyr Leu Ser Lys Tyr Thr Ile Asn Pro Ala Ile Ala His Gly Ile
            405                 410                 415

Ser Glu Tyr Val Gly Ser Val Glu Val Gly Lys Val Ala Asp Leu Val
            420                 425                 430

Leu Trp Ser Pro Ala Phe Phe Gly Val Lys Pro Asn Met Ile Ile Lys
        435                 440                 445

Gly Gly Phe Ile Ala Leu Ser Gln Met Gly Asp Ala Asn Ala Ser Ile
        450                 455                 460

Pro Thr Pro Gln Pro Val Tyr Tyr Arg Glu Met Phe Ala His His Gly
465                 470                 475                 480

Lys Ala Lys Tyr Asp Ala Asn Ile Thr Phe Val Ser Gln Ala Ala Tyr
            485                 490                 495

Asp Lys Gly Ile Lys Glu Glu Leu Gly Leu Glu Arg Gln Val Leu Pro
            500                 505                 510

Val Lys Asn Cys Arg Asn Ile Thr Lys Lys Asp Met Gln Phe Asn Asp
        515                 520                 525

Thr Thr Ala His Ile Glu Val Asn Pro Glu Thr Tyr His Val Phe Val
530                 535                 540

Asp Gly Lys Glu Val Thr Ser Lys Pro Ala Asn Lys Val Ser Leu Ala
545                 550                 555                 560

Gln Leu Phe Ser Ile Phe His His His His His His
            565                 570

<210> SEQ ID NO 26
<211> LENGTH: 566
<212> TYPE: PRT
<213> ORGANISM: Artificial Sequence
<220> FEATURE:
<223> OTHER INFORMATION: Synthetic

<400> SEQUENCE: 26

```
Met Glu Lys Ile Ser Arg Lys Glu Tyr Val Ser Met Tyr Gly Pro Thr
1               5                   10                  15

Thr Gly Asp Lys Val Arg Leu Gly Asp Thr Asp Leu Ile Ala Glu Val
            20                  25                  30

Glu His Asp Tyr Thr Ile Tyr Gly Glu Leu Lys Phe Gly Gly Gly
        35                  40                  45

Lys Thr Leu Arg Glu Gly Met Ser Gln Ser Asn Asn Pro Ser Lys Glu
    50                  55                  60

Glu Leu Asp Leu Ile Ile Thr Asn Ala Leu Ile Val Asp Tyr Thr Gly
65                  70                  75                  80

Ile Tyr Lys Ala Asp Ile Gly Ile Lys Asp Gly Lys Ile Ala Gly Ile
            85                  90                  95

Gly Lys Gly Gly Asn Lys Asp Met Gln Asp Gly Val Lys Asn Asn Leu
            100                 105                 110

Ser Val Gly Pro Ala Thr Glu Ala Leu Ala Gly Glu Gly Leu Ile Val
        115                 120                 125

Thr Ala Gly Gly Ile Asp Thr His Ile His Phe Ile Ser Pro Gln Gln
130                 135                 140

Ile Pro Thr Ala Phe Ala Ser Gly Val Thr Thr Met Ile Gly Gly Gly
145                 150                 155                 160

Thr Gly Pro Ala Asp Gly Thr Asn Ala Thr Thr Ile Thr Pro Gly Arg
            165                 170                 175

Arg Asn Leu Lys Leu Arg Ala Ala Glu Glu Tyr Ser Met Asn Leu Gly
            180                 185                 190

Phe Leu Ala Lys Gly Asn Ala Ser Asn Asp Ala Ser Leu Ala Asp Gln
        195                 200                 205

Ile Glu Ala Gly Ala Ile Gly Phe Lys Ile His Glu Asp Trp Gly Thr
210                 215                 220

Thr Pro Ser Ala Ile Asn His Ala Leu Asp Val Ala Asp Lys Tyr Asp
225                 230                 235                 240

Val Gln Val Ala Ile His Thr Asp Thr Leu Asn Glu Ala Gly Cys Val
            245                 250                 255

Glu Asp Thr Ala Ala Ile Ala Gly Arg Thr Met His Thr Phe His Thr
            260                 265                 270

Glu Gly Ala Gly Gly Gly His Ala Pro Asp Ile Ile Lys Val Ala Gly
        275                 280                 285

Glu His Asn Ile Leu Pro Ala Ser Thr Asn Pro Thr Ile Pro Phe Thr
        290                 295                 300

Val Asn Thr Glu Ala Glu His Met Asp Met Leu Met Val Cys His His
305                 310                 315                 320

Leu Asp Lys Ser Ile Lys Glu Asp Val Gln Phe Ala Asp Ser Arg Ile
            325                 330                 335

Arg Pro Gln Thr Ile Ala Ala Glu Asp Thr Leu His Asp Met Gly Ile
            340                 345                 350

Phe Ser Ile Thr Ser Ser Asp Ser Gln Ala Met Gly Arg Val Gly Glu
            355                 360                 365

Val Ile Thr Arg Thr Trp Gln Thr Ala Asp Lys Asn Lys Lys Glu Phe
370                 375                 380

Gly Arg Leu Lys Glu Glu Lys Gly Asp Asn Asp Asn Phe Arg Ile Lys
385                 390                 395                 400

Arg Tyr Leu Ser Lys Tyr Thr Ile Asn Pro Ala Ile Ala His Gly Ile
            405                 410                 415
```

-continued

```
Ser Glu Tyr Val Gly Ser Val Glu Val Gly Lys Val Ala Asp Leu Val
            420             425             430

Leu Trp Ser Pro Ala Phe Phe Gly Val Lys Pro Asn Met Ile Ile Lys
        435             440             445

Gly Gly Phe Ile Ala Leu Ser Gln Met Gly Asp Ala Asn Ala Ser Ile
    450             455             460

Pro Thr Pro Gln Pro Val Tyr Arg Glu Met Phe Ala His His Gly
465             470             475             480

Lys Ala Lys Tyr Asp Ala Asn Ile Thr Phe Val Ser Gln Ala Ala Tyr
            485             490             495

Asp Lys Gly Ile Lys Glu Glu Leu Gly Leu Glu Arg Gln Val Leu Pro
            500             505             510

Val Lys Asn Cys Arg Asn Ile Thr Lys Lys Asp Met Gln Phe Asn Asp
        515             520             525

Thr Thr Ala His Ile Glu Val Asn Pro Glu Thr Tyr His Val Phe Val
        530             535             540

Asp Gly Lys Glu Val Thr Ser Lys Pro Ala Asn Lys Val Ser Leu Ala
545             550             555             560

Gln Leu Phe Ser Ile Phe
                565
```